United States Patent
Arkenau-Marić et al.

(10) Patent No.: US 10,675,278 B2
(45) Date of Patent: *Jun. 9, 2020

(54) CRUSH RESISTANT DELAYED-RELEASE DOSAGE FORMS

(71) Applicant: GRÜNENTHAL GMBH, Aachen (DE)

(72) Inventors: Elisabeth Arkenau-Marić, Köln (DE); Johannes Bartholomäus, Aachen (DE); Heinrich Kugelmann, Aachen (DE)

(73) Assignee: GRÜNENTHAL GMBH, Aachen (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/061,252

(22) Filed: Mar. 4, 2016

(65) Prior Publication Data

US 2016/0184297 A1 Jun. 30, 2016

Related U.S. Application Data

(60) Continuation of application No. 14/749,939, filed on Jun. 25, 2015, now abandoned, which is a continuation of application No. 14/141,793, filed on Dec. 27, 2013, now abandoned, which is a continuation of application No. 12/640,915, filed on Dec. 17, 2009, now abandoned, which is a division of application No. 11/348,295, filed on Feb. 6, 2006, now abandoned.

(30) Foreign Application Priority Data

Feb. 4, 2005 (DE) .................. 10 2005 005 446

(51) Int. Cl.

| | |
|---|---|
| A61K 9/20 | (2006.01) |
| A61K 31/485 | (2006.01) |
| B29C 48/00 | (2019.01) |
| B29C 48/21 | (2019.01) |
| B29C 48/14 | (2019.01) |
| A61K 31/135 | (2006.01) |
| A61K 31/277 | (2006.01) |
| A61K 31/4418 | (2006.01) |
| A61K 31/55 | (2006.01) |
| A61K 31/554 | (2006.01) |
| A61J 3/00 | (2006.01) |
| A61K 9/48 | (2006.01) |
| A61J 3/10 | (2006.01) |
| A61K 9/28 | (2006.01) |
| A61K 31/4422 | (2006.01) |
| B29B 7/00 | (2006.01) |
| B29B 9/02 | (2006.01) |
| B29B 9/12 | (2006.01) |
| B29C 43/02 | (2006.01) |
| A61J 3/06 | (2006.01) |
| A61K 9/00 | (2006.01) |

(Continued)

(52) U.S. Cl.
CPC ............ *A61K 31/485* (2013.01); *A61J 3/005* (2013.01); *A61J 3/06* (2013.01); *A61J 3/10* (2013.01); *A61K 9/205* (2013.01); *A61K 9/2009* (2013.01); *A61K 9/2013* (2013.01); *A61K 9/2031* (2013.01); *A61K 9/2054* (2013.01); *A61K 9/2068* (2013.01); *A61K 9/2072* (2013.01); *A61K 9/2086* (2013.01); *A61K 9/2095* (2013.01); *A61K 9/2893* (2013.01); *A61K 9/4808* (2013.01); *A61K 31/135* (2013.01); *A61K 31/277* (2013.01); *A61K 31/4418* (2013.01); *A61K 31/4422* (2013.01); *A61K 31/55* (2013.01); *A61K 31/554* (2013.01); *B29B 7/002* (2013.01); *B29B 9/02* (2013.01); *B29B 9/12* (2013.01); *B29C 43/02* (2013.01); *B29C 48/0011* (2019.02); *B29C 48/0022* (2019.02); *B29C 48/022* (2019.02); *B29C 48/146* (2019.02); *B29C 48/21* (2019.02); *A61K 9/0053* (2013.01); *A61K 9/20* (2013.01); *B29C 35/0261* (2013.01); *B29C 45/0001* (2013.01); *B29C 2793/009* (2013.01); *B29K 2105/0035* (2013.01); *B29K 2105/0044* (2013.01); *B29K 2105/251* (2013.01); *B29K 2995/0056* (2013.01); *B29L 2031/753* (2013.01); *B29L 2031/772* (2013.01)

(58) Field of Classification Search
None
See application file for complete search history.

(56) References Cited

U.S. PATENT DOCUMENTS

| | | | |
|---|---|---|---|
| 2,524,855 A | 10/1950 | Schnider et al. | |
| 2,806,033 A | 9/1957 | Lewenstein et al. | |

(Continued)

FOREIGN PATENT DOCUMENTS

| | | |
|---|---|---|
| AR | 046994 A1 | 12/2004 |
| AR | 045353 A1 | 10/2005 |

(Continued)

OTHER PUBLICATIONS

Alekseeva et al, Chemical-Pharmaceutical Journal, vol. 41, No. 9, 2007, 49-52. (Full translation attached.).

(Continued)

*Primary Examiner* — Susan T Tran
(74) *Attorney, Agent, or Firm* — Norris McLaughlin, P.A.

(57) ABSTRACT

The invention relates to a dosage form comprising a physiologically effective amount of a physiologically active substance (A), a synthetic, semi-synthetic or natural polymer (C), optionally one or more physiologically acceptable auxiliary substances (B) and optionally a synthetic, semi-synthetic or natural wax (D), wherein the dosage form exhibits a resistance to crushing of at least 400 N and wherein under physiological conditions the release of the physiologically active substance (A) from the dosage form is at least partially delayed.

40 Claims, 4 Drawing Sheets

(51) Int. Cl.
  *B29K 105/00* (2006.01)
  *B29C 35/02* (2006.01)
  *B29C 45/00* (2006.01)
  *B29L 31/00* (2006.01)

(56) References Cited

U.S. PATENT DOCUMENTS

| | | |
|---|---|---|
| 2,987,445 A | 6/1961 | Levesque |
| 3,332,950 A | 7/1967 | Blumberg et al. |
| 3,370,035 A | 2/1968 | Ogura et al. |
| 3,652,589 A | 3/1972 | Flick et al. |
| 3,658,259 A | 4/1972 | Ledergerber et al. |
| 3,806,603 A | 4/1974 | Gaunt et al. |
| 3,865,108 A | 2/1975 | Hartop |
| 3,941,865 A | 3/1976 | Miller et al. |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers et al. |
| 4,343,789 A | 8/1982 | Kawata et al. |
| 4,353,877 A | 10/1982 | Hess et al. |
| 4,353,887 A | 10/1982 | Hess et al. |
| 4,404,183 A | 9/1983 | Kawata et al. |
| 4,427,681 A | 1/1984 | Munshi |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,599,342 A | 7/1986 | La Hann |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura |
| 4,711,894 A | 12/1987 | Wenzel et al. |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,954,346 A | 9/1990 | Sparta et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinty |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,194 A | 4/1993 | Edgren et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | McGinity et al. |
| 5,229,164 A | 7/1993 | Pins et al. |
| 5,273,758 A | 12/1993 | Royce |
| 5,326,852 A | 7/1994 | Fujikake et al. |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,601,842 A | 2/1997 | Bartholomaeus |
| 5,620,697 A | 4/1997 | Tormala et al. |
| 5,679,685 A | 10/1997 | Cincotta et al. |
| 5,681,517 A | 10/1997 | Metzger |
| 5,593,694 A | 11/1997 | Hayashida et al. |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Graudums et al. |
| 5,811,126 A | 9/1998 | Krishnamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,914,132 A | 6/1999 | Kelm et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,235,825 B1 | 2/2001 | Yoshida et al. |
| 6,228,863 B1 | 5/2001 | Palermo et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,251,430 B1 | 6/2001 | Zhang et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,322,811 B1 | 11/2001 | Verma et al. |
| 6,322,819 B1 | 11/2001 | Burnside et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |

(56) References Cited

U.S. PATENT DOCUMENTS

| | | |
|---|---|---|
| 6,375,963 B1 | 4/2002 | Repka et al. |
| 6,384,020 B1 | 5/2002 | Flanner et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,455,052 B1 | 9/2002 | Marcussen et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breithenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,946,146 B2 | 9/2005 | Mulye |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 1,674,790 A1 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,932,258 B2 | 4/2011 | Petereit et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric |
| 8,101,630 B2 | 1/2012 | Kumar et al. |
| 8,114,383 B2 | 2/2012 | Bartholomaus et al. |
| 8,114,384 B2 * | 2/2012 | Arkenau ............ A61K 9/2095 424/10.1 |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomaus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Maric |
| 8,858,963 B1 | 10/2014 | Devarakonda et al. |
| 8,901,113 B2 | 12/2014 | Leech et al. |
| 9,044,758 B2 | 6/2015 | Niwa et al. |
| 9,192,578 B2 | 11/2015 | McGinity et al. |
| 9,463,165 B2 | 10/2016 | Shimatani et al. |
| 9,629,807 B2 | 4/2017 | Arkenau-Maric et al. |
| 9,675,610 B2 | 6/2017 | Bartholomaeus et al. |
| 9,737,490 B2 | 8/2017 | Barnscheid et al. |
| 9,750,701 B2 | 9/2017 | Jans et al. |
| 9,884,022 B2 | 2/2018 | Deshmukh et al. |
| 9,925,146 B2 | 3/2018 | Barnscheid et al. |
| 10,130,591 B2 | 11/2018 | Bartholomäus et al. |
| 10,154,966 B2 | 12/2018 | Barnscheidt et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0187192 A1 | 2/2002 | Joshi et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0059397 A1 | 3/2003 | Hughes |
| 2003/0064099 A1 | 4/2003 | Oshlack et al. |
| 2003/0068276 A1 | 4/2003 | Hughes et al. |
| 2003/0068370 A1 | 4/2003 | Sackler |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chem et al. |
| 2003/0077327 A1 | 4/2003 | Durig et al. |
| 2003/0091630 A1 | 5/2003 | Louie-Helm et al. |
| 2003/0092724 A1 | 5/2003 | Huaihung et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0158265 A1 | 8/2003 | Radhakrishnan et al. |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0224051 A1 | 12/2003 | Fink et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0049079 A1 | 3/2004 | Murray et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0170680 A1 | 9/2004 | Oshlack et al. |
| 2004/0185105 A1 | 9/2004 | Berner et al. |
| 2004/0213845 A1 | 10/2004 | Sugihara |
| 2004/0213848 A1 | 10/2004 | Li et al. |
| 2004/0253310 A1 | 12/2004 | Fischer et al. |
| 2005/0015730 A1 | 1/2005 | Gunturi et al. |
| 2005/0031546 A1 | 2/2005 | Bartholomaeus et al. |
| 2005/0058706 A1 | 3/2005 | Bartholomaeus et al. |
| 2005/0063214 A1 | 3/2005 | Takashima |
| 2005/0079138 A1 | 4/2005 | Chickering, III et al. |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |

(56) References Cited

U.S. PATENT DOCUMENTS

| | | |
|---|---|---|
| 2005/0152843 A1 | 7/2005 | Bartholomaeus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaeus et al. |
| 2005/0191352 A1 | 9/2005 | Hayes |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogman et al. |
| 2005/0266084 A1 | 12/2005 | Li et al. |
| 2005/0271594 A1 | 12/2005 | Groenewoud |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedman et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaus et al. |
| 2006/0193914 A1 | 8/2006 | Ashworth et al. |
| 2006/0194759 A1 | 8/2006 | Eidelson |
| 2006/0194826 A1 | 8/2006 | Oshlack et al. |
| 2006/0204575 A1 | 9/2006 | Feng et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0048373 A1 | 3/2007 | Chastain et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264326 A1 | 11/2007 | Guimberteau et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0014228 A1 | 1/2008 | Darmuzey et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |
| 2008/0081290 A1 | 3/2008 | Wada et al. |
| 2008/0085304 A1 | 4/2008 | Baichwal et al. |
| 2008/0131503 A1 | 6/2008 | Holm et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0207757 A1 | 8/2008 | Mickle |
| 2008/0220079 A1 | 9/2008 | Chen et al. |
| 2008/0233178 A1 | 9/2008 | Reidenberg et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0260836 A1 | 10/2008 | Boyd |
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0087486 A1 | 4/2009 | Krumme |
| 2009/0117191 A1 | 5/2009 | Brown Miller et al. |
| 2009/0143478 A1 | 6/2009 | Richardson et al. |
| 2009/0155357 A1 | 6/2009 | Muhuri |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0258066 A1 | 10/2009 | Venkatesh et al. |
| 2009/0317355 A1 | 12/2009 | Roth et al. |
| 2009/0318395 A1 | 12/2009 | Schramm et al. |
| 2010/0015223 A1 | 1/2010 | Cailly-Dufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0239667 A1 | 9/2010 | Hemmingsen et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2010/0316712 A1 | 12/2010 | Nangia et al. |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0077238 A1 | 3/2011 | Leech et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0129535 A1 | 6/2011 | Mantelle |
| 2011/0135731 A1 | 6/2011 | Kao et al. |
| 2011/0159100 A1 | 6/2011 | Anderson et al. |
| 2011/0187017 A1 | 8/2011 | Haupts |
| 2011/0223244 A1 | 9/2011 | Liversidge et al. |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0277319 A1 | 11/2012 | Steigerwald et al. |
| 2012/0321716 A1 | 12/2012 | Vachon et al. |
| 2013/0017262 A1 | 1/2013 | Mullen et al. |
| 2013/0022654 A1 | 1/2013 | Deshmukh et al. |
| 2013/0028970 A1 | 1/2013 | Schwier et al. |
| 2013/0028972 A1 | 1/2013 | Schwier et al. |
| 2013/0059010 A1 | 3/2013 | Herry et al. |
| 2013/0090349 A1 | 4/2013 | Geiler et al. |
| 2013/0129825 A1 | 5/2013 | Billoet et al. |

(56) References Cited

U.S. PATENT DOCUMENTS

| | | |
|---|---|---|
| 2013/0129826 A1 | 5/2013 | Geiler et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomäus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0034885 A1 | 2/2014 | Leech |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau-Maric et al. |
| 2014/0112989 A1 | 4/2014 | Bartholomäus et al. |
| 2014/0170079 A1 | 6/2014 | Arkenau Maric et al. |
| 2014/0186440 A1 | 7/2014 | Han et al. |
| 2014/0271848 A1 | 9/2014 | Guido et al. |
| 2014/0275143 A1 | 9/2014 | Devarakonda et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wening et al. |
| 2015/0030677 A1 | 1/2015 | Adjei et al. |
| 2015/0064250 A1 | 3/2015 | Ghebre-Sellassie et al. |
| 2015/0079150 A1 | 3/2015 | Fischer et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0190348 A1 | 7/2015 | Haksar et al. |
| 2015/0313850 A1 | 11/2015 | Krishnamurti et al. |
| 2015/0374630 A1 | 12/2015 | Arkenau Maric et al. |
| 2016/0089439 A1 | 3/2016 | Rajagopalan |
| 2016/0175256 A1 | 6/2016 | Bartholomaeus et al. |
| 2016/0184297 A1 | 6/2016 | Arkenau-Maric et al. |
| 2016/0256456 A1 | 9/2016 | Caruso et al. |
| 2016/0263037 A1 | 9/2016 | Arkenau-Maric et al. |
| 2016/0346274 A1 | 12/2016 | Vaka et al. |
| 2016/0361308 A1 | 12/2016 | Bartholomaeus et al. |
| 2016/0367549 A1 | 12/2016 | Bartholomaeus et al. |
| 2017/0027886 A1 | 2/2017 | Bartholomaeus et al. |
| 2017/0112766 A1 | 4/2017 | Wenig et al. |

FOREIGN PATENT DOCUMENTS

| | | |
|---|---|---|
| AR | 049562 A1 | 8/2006 |
| AR | 049839 A1 | 9/2006 |
| AR | 053304 A1 | 5/2007 |
| AR | 054222 A1 | 6/2007 |
| AR | 054328 A1 | 6/2007 |
| AU | 769807 B2 | 3/2001 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 A1 | 8/2006 |
| AU | 2006210145 B2 | 8/2006 |
| AU | 2009207796 A1 | 7/2009 |
| AU | 2009243681 A1 | 11/2009 |
| AU | 2009299810 B2 | 4/2010 |
| AU | 2006311116 B2 | 1/2013 |
| BR | PI0413318 A | 10/2006 |
| BR | PI0413361 A | 10/2006 |
| BR | PI0513300 A | 5/2008 |
| BR | PI0606145 A2 | 2/2009 |
| CA | 0722109 A | 11/1965 |
| CA | 2082573 C | 5/1993 |
| CA | 2577233 A1 | 10/1997 |
| CA | 2650637 A1 | 10/1997 |
| CA | 2229621 A1 | 3/1998 |
| CA | 2317747 A1 | 7/1999 |
| CA | 2343234 A1 | 3/2000 |
| CA | 2352874 A1 | 6/2000 |
| CA | 2414349 A1 | 1/2002 |
| CA | 2456322 A1 | 2/2003 |
| CA | 2502965 A1 | 5/2004 |
| CA | 2503155 A1 | 5/2004 |
| CA | 2534925 A1 | 2/2005 |
| CA | 2534932 A1 | 2/2005 |
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 1473562 A | 2/2004 |
| CN | 1980643 A | 4/2005 |
| CN | 101010071 A | 6/2005 |
| CN | 1671475 A | 9/2005 |
| CN | 101022787 A | 1/2006 |
| CN | 1863513 A | 11/2006 |
| CN | 1863514 A | 11/2006 |
| CN | 1917862 A | 2/2007 |
| CN | 1942174 A | 4/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 | 12/2007 |
| CN | 101111232 A | 1/2008 |
| CN | 101175482 A | 2/2008 |
| CN | 101370485 A | 2/2009 |
| CN | 101394839 A | 3/2009 |
| CN | 101578096 A | 11/2009 |
| CN | 101652128 A | 2/2010 |
| CN | 102413835 A | 4/2012 |
| CN | 102821757 A | 12/2012 |
| DE | 2530563 A1 | 1/1977 |
| DE | 4229085 A1 | 3/1994 |
| DE | 4309528 A1 | 9/1994 |
| DE | 4446470 A1 | 6/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 A1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |
| DE | 19856147 A1 | 6/2000 |
| DE | 19949740 A1 | 3/2001 |
| DE | 19960494 A1 | 6/2001 |
| DE | 10036400 A1 | 6/2002 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 10336400 A1 | 3/2005 |
| DE | 10361596 A1 | 9/2005 |

(56) References Cited

FOREIGN PATENT DOCUMENTS

| | | |
|---|---|---|
| DE | 102004019916 A1 | 11/2005 |
| DE | 102004020220 A1 | 11/2005 |
| DE | 102004032049 A1 | 1/2006 |
| DE | 102004032051 A1 | 1/2006 |
| DE | 102004032103 A1 | 1/2006 |
| DE | 102005005446 A1 | 8/2006 |
| DE | 102005005449 A1 | 8/2006 |
| DE | 102007011485 A1 | 9/2008 |
| DK | 1658055 T3 | 7/2007 |
| DK | 1658054 T3 | 10/2007 |
| DK | 1515702 T3 | 1/2009 |
| EC | SP066345 A | 8/2006 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0228417 A1 | 7/1987 |
| EP | 0229652 A2 | 7/1987 |
| EP | 0232877 A2 | 8/1987 |
| EP | 0239973 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0358105 A1 | 3/1990 |
| EP | 0228417 B1 | 9/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 A1 | 7/1995 |
| EP | 0675710 A1 | 10/1995 |
| EP | 0682945 A2 | 11/1995 |
| EP | 0693475 A1 | 1/1996 |
| EP | 0820693 A1 | 1/1996 |
| EP | 0696598 A1 | 2/1996 |
| EP | 0216453 B1 | 3/1996 |
| EP | 0583726 B1 | 11/1996 |
| EP | 0756480 A1 | 2/1997 |
| EP | 0760654 A1 | 3/1997 |
| EP | 0761211 A1 | 3/1997 |
| EP | 0780369 A1 | 6/1997 |
| EP | 0785775 A1 | 7/1997 |
| EP | 0809488 A1 | 12/1997 |
| EP | 0820698 A1 | 1/1998 |
| EP | 0820753 A2 | 1/1998 |
| EP | 0857062 A2 | 8/1998 |
| EP | 0864324 A1 | 9/1998 |
| EP | 0864326 A2 | 9/1998 |
| EP | 0598606 B1 | 6/1999 |
| EP | 0675710 B1 | 8/1999 |
| EP | 0980894 A1 | 2/2000 |
| EP | 0988106 A1 | 3/2000 |
| EP | 1014941 A1 | 7/2000 |
| EP | 1070504 A1 | 1/2001 |
| EP | 1127871 A1 | 8/2001 |
| EP | 1138321 A2 | 10/2001 |
| EP | 1152026 A1 | 11/2001 |
| EP | 1138321 A3 | 1/2002 |
| EP | 1166776 A2 | 1/2002 |
| EP | 1201233 A1 | 5/2002 |
| EP | 0661045 B1 | 7/2002 |
| EP | 1250045 A2 | 10/2002 |
| EP | 1251120 A1 | 10/2002 |
| EP | 1293127 A2 | 3/2003 |
| EP | 1293195 A1 | 3/2003 |
| EP | 1293196 A2 | 3/2003 |
| EP | 1127871 B1 | 9/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658054 A1 | 2/2005 |
| EP | 1658055 A1 | 2/2005 |
| EP | 1515702 B1 | 3/2005 |
| EP | 1527775 A1 | 4/2005 |
| EP | 1558221 A1 | 8/2005 |
| EP | 1558257 A1 | 8/2005 |
| EP | 1560585 B1 | 8/2005 |
| EP | 1611880 A2 | 1/2006 |
| EP | 1658054 B1 | 5/2006 |
| EP | 1138321 B1 | 1/2007 |
| EP | 1740161 A2 | 1/2007 |
| EP | 1658055 B1 | 3/2007 |
| EP | 1765303 A1 | 3/2007 |
| EP | 1786403 A1 | 5/2007 |
| EP | 1558221 B1 | 6/2007 |
| EP | 1813276 A1 | 8/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 11/2010 |
| EP | 2249811 A1 | 11/2010 |
| EP | 2273983 A1 | 1/2011 |
| EP | 2402004 A2 | 1/2012 |
| ES | 2336571 T3 | 12/2004 |
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |
| GB | 2047095 A | 11/1980 |
| GB | 2057878 A | 4/1981 |
| GB | 2238478 A | 6/1991 |
| HR | 20070456 T3 | 6/2007 |
| HR | 20070272 T3 | 11/2007 |
| JP | S36022895 | 11/1961 |
| JP | S55162714 A | 12/1980 |
| JP | S5659708 A | 5/1981 |
| JP | S56169622 A | 12/1981 |
| JP | S62240061 A | 10/1987 |
| JP | H0249719 A | 2/1990 |
| JP | 03-501737 A | 4/1991 |
| JP | H0517566 A | 1/1993 |
| JP | H06507645 A | 9/1994 |
| JP | 08053331 A | 2/1996 |
| JP | 8-505076 A | 6/1996 |
| JP | H09508410 A | 8/1997 |
| JP | H1057450 A | 3/1998 |
| JP | H10251149 A | 9/1998 |
| JP | 2000513333 A | 10/2000 |
| JP | 2002524150 A | 8/2002 |
| JP | 2002-275175 A | 9/2002 |
| JP | 2003113119 A | 4/2003 |
| JP | 2003125706 A | 5/2003 |
| JP | 2003526598 A | 9/2003 |
| JP | 2004143071 A | 5/2004 |
| JP | 2004530676 A | 10/2004 |
| JP | 2005506965 A | 3/2005 |
| JP | 2005515152 A | 5/2005 |
| JP | 2005534664 A | 11/2005 |
| JP | 2006506374 A | 2/2006 |
| JP | 2007501201 A | 1/2007 |
| JP | 2007501202 A | 1/2007 |

(56) References Cited

FOREIGN PATENT DOCUMENTS

| | | |
|---|---|---|
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 20095238833 A | 6/2009 |
| JP | 2009524626 A | 7/2009 |
| JP | 2009531453 A | 9/2009 |
| JP | 2009536927 A | 10/2009 |
| JP | 2009537456 A | 10/2009 |
| JP | 2010505949 A | 2/2010 |
| JP | 2010527285 A | 8/2010 |
| JP | 2010534204 A | 11/2010 |
| JP | 2011504455 A | 2/2011 |
| JP | 2011506493 A | 3/2011 |
| JP | 2011510034 A | 3/2011 |
| JP | WO 2011/059074 A1 | 5/2011 |
| JP | 2012515735 A | 7/2012 |
| JP | 2012828845 A | 11/2012 |
| JP | 2013523804 A | 6/2013 |
| JP | 2013155124 A | 8/2013 |
| JP | 2013536810 A | 9/2013 |
| JP | 2014505736 A | 3/2014 |
| JP | 2014528437 A | 10/2014 |
| JP | 6085307 B2 | 2/2017 |
| JP | 2013523780 A | 6/2017 |
| KR | 1020060069832 A | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 A | 8/2010 |
| MX | 2010012039 A | 11/2010 |
| NO | 20061054 A | 3/2006 |
| NO | 20070578 A | 1/2007 |
| NO | 20074412 A | 11/2007 |
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RU | 2131244 C1 | 6/1999 |
| RU | 2198197 C2 | 2/2003 |
| RU | 2220715 C2 | 1/2004 |
| RU | 2328275 C2 | 5/2004 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| RU | 2567723 C2 | 11/2015 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | 1254634 B | 5/2006 |
| WO | WO 1980/000841 A1 | 5/1980 |
| WO | WO 1989/005624 A1 | 6/1989 |
| WO | WO 1990/003776 A1 | 4/1990 |
| WO | WO 1993/006723 A1 | 4/1993 |
| WO | WO 93/10765 A1 | 6/1993 |
| WO | WO 1993/010758 A1 | 6/1993 |
| WO | WO 1993/011749 A1 | 6/1993 |
| WO | WO 1993/023017 A1 | 11/1993 |
| WO | WO 1994/006414 A1 | 3/1994 |
| WO | WO 1994/008567 A1 | 4/1994 |
| WO | WO 1995/017174 A1 | 6/1995 |
| WO | WO 1995/020947 A1 | 8/1995 |
| WO | WO 1995/022319 A1 | 8/1995 |
| WO | WO 1995/030422 A1 | 11/1995 |
| WO | WO 1996/000066 A1 | 1/1996 |
| WO | WO 1996/003979 A1 | 2/1996 |
| WO | WO 1996/014058 A1 | 5/1996 |
| WO | WO 1997/000673 A1 | 1/1997 |
| WO | WO 1997/033566 | 9/1997 |
| WO | WO 1997/049384 A1 | 12/1997 |
| WO | WO 1998/035655 A3 | 2/1998 |
| WO | WO 1998/020073 A2 | 5/1998 |
| WO | WO 1998/028698 A1 | 7/1998 |
| WO | WO 1998/035655 A2 | 8/1998 |
| WO | WO 1998/051758 A1 | 11/1998 |
| WO | WO 1999/012864 A1 | 3/1999 |
| WO | WO 1999/032120 A1 | 7/1999 |
| WO | WO 1999/044591 A1 | 9/1999 |
| WO | WO 1999/045887 A2 | 9/1999 |
| WO | WO 1999/048481 A1 | 9/1999 |
| WO | WO 00/15261 A1 | 3/2000 |
| WO | WO 2000/013647 A1 | 3/2000 |
| WO | WO 2000/033835 A1 | 6/2000 |
| WO | WO 2000/040205 A2 | 7/2000 |
| WO | WO 2001/008661 A2 | 2/2001 |
| WO | WO 2001/012230 A1 | 2/2001 |
| WO | WO 2001/015667 A1 | 3/2001 |
| WO | WO 2001/052651 A2 | 7/2001 |
| WO | WO 2001/058451 A1 | 8/2001 |
| WO | WO 2001/097783 A1 | 12/2001 |
| WO | WO 2002/026061 A1 | 4/2002 |
| WO | WO 2002/026262 A2 | 4/2002 |
| WO | WO 2002/026928 A1 | 4/2002 |
| WO | WO 2002/035991 A2 | 5/2002 |
| WO | WO 2002/071860 A1 | 9/2002 |
| WO | WO 2002/088217 A1 | 11/2002 |
| WO | WO 2002/094254 A2 | 11/2002 |
| WO | WO 2003/006723 A1 | 1/2003 |
| WO | WO 2003/007802 A2 | 1/2003 |
| WO | WO 2003/013433 A2 | 2/2003 |
| WO | WO 2003/013476 A1 | 2/2003 |
| WO | WO 2003/013479 A1 | 2/2003 |
| WO | WO 2003/013538 A1 | 2/2003 |
| WO | WO 2003/015531 A2 | 2/2003 |
| WO | WO 2003/018015 A1 | 3/2003 |
| WO | WO 2003/024426 A1 | 3/2003 |
| WO | WO 2003/024430 A1 | 3/2003 |
| WO | WO 2003/026624 A1 | 4/2003 |
| WO | WO 2003/026743 A2 | 4/2003 |
| WO | WO 2003/028698 A1 | 4/2003 |
| WO | WO 2003/028990 A1 | 4/2003 |
| WO | WO 2003/031546 A1 | 4/2003 |
| WO | WO 2003/035029 A1 | 5/2003 |
| WO | WO 2003/035053 A1 | 5/2003 |
| WO | WO 2003/035054 A1 | 5/2003 |
| WO | WO 2003/035177 A2 | 5/2003 |
| WO | WO 2003/039561 A1 | 5/2003 |
| WO | WO 2003/049689 A2 | 6/2003 |
| WO | WO 2003/053417 A2 | 7/2003 |
| WO | WO 2003/068392 A1 | 8/2003 |
| WO | WO 2003/070191 A1 | 8/2003 |
| WO | WO 2003/092648 A1 | 11/2003 |
| WO | WO 2003/094812 A1 | 11/2003 |
| WO | WO 2003/105808 A1 | 12/2003 |
| WO | WO 2004/004693 A1 | 1/2004 |
| WO | WO 2004/043967 A1 | 2/2004 |
| WO | WO 2004/026262 A2 | 4/2004 |
| WO | WO 2004/026263 A2 | 4/2004 |
| WO | WO 2004/026280 A2 | 4/2004 |
| WO | WO 2004/037222 A1 | 5/2004 |
| WO | WO 2004/037230 A1 | 5/2004 |
| WO | WO 2004/037259 A1 | 5/2004 |
| WO | WO 2004/037260 A1 | 5/2004 |
| WO | WO 2004/043449 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093801 A2 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/002553 A2 | 1/2005 |

(56) References Cited

FOREIGN PATENT DOCUMENTS

| | | |
|---|---|---|
| WO | WO 2005/016313 A1 | 2/2005 |
| WO | WO 2005/016314 A1 | 2/2005 |
| WO | WO 2005/032524 A2 | 4/2005 |
| WO | WO 2005/041968 A2 | 5/2005 |
| WO | WO 2005/053587 A1 | 6/2005 |
| WO | WO 2005/053656 A1 | 6/2005 |
| WO | WO 2005/055981 A2 | 6/2005 |
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/002884 B1 | 3/2006 |
| WO | WO 2006/024881 A2 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/128471 A2 | 12/2006 |
| WO | WO 2007/005716 A2 | 1/2007 |
| WO | WO 2007/008752 A2 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/093642 A2 | 8/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |
| WO | WO 2007/131357 A1 | 11/2007 |
| WO | WO 2007/138466 A2 | 12/2007 |
| WO | WO 2007/149438 A2 | 12/2007 |
| WO | WO 2008/023261 A1 | 2/2008 |
| WO | WO 2008/033523 A1 | 3/2008 |
| WO | WO 2008/045060 A1 | 4/2008 |
| WO | WO 2008/069941 A2 | 6/2008 |
| WO | WO 2008/086804 A2 | 7/2008 |
| WO | WO 2008/107149 A2 | 9/2008 |
| WO | WO 2008/107149 A3 | 9/2008 |
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A | 9/2009 |
| WO | WO 2009/135680 A1 | 11/2009 |
| WO | WO 2010/022193 A2 | 2/2010 |
| WO | WO 2010/037854 A2 | 4/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/095314 A2 | 8/2011 |
| WO | WO 2011/095314 A3 | 8/2011 |
| WO | WO 2011/124953 A2 | 10/2011 |
| WO | WO 2011/124953 A3 | 10/2011 |
| WO | WO 2011/128630 A2 | 10/2011 |
| WO | WO 2011/141241 A1 | 11/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/085657 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/025449 A1 | 3/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/158810 A1 | 10/2013 |
| WO | WO 2013/167735 A1 | 11/2013 |
| WO | WO 2014/032741 A1 | 3/2014 |
| WO | WO 2014/059512 A1 | 4/2014 |
| WO | WO 2014/140231 A1 | 9/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/023675 A2 | 2/2015 |
| WO | WO 2015/048597 A1 | 4/2015 |
| WO | WO 2015/103379 A1 | 7/2015 |
| WO | WO 2015/120201 A1 | 8/2015 |
| WO | WO 2017/178658 A1 | 10/2017 |

OTHER PUBLICATIONS 2.9 Methoden der pharmazeutischen Technologie, European Pharmacopeia, 143-144, 1997. (Full English translation attached).

Albertini, B. "New spray congealing atomizer for the microencapsulation of highly concentrated solid and liquid substances" European Journal of Pharmaceutics and Biopharmaceutics 69 (2008) 348-357.

Almeida, A. et al., Ethylene vinyl acetate as matrix for oral sustained release dosage forms produced via hot-melt extrusion, European Journal of Pharmaceutics and Biopharmaceutics 77 (2011) 297-305.

Almeida, A. et al., Sustained release from hot-melt extruded matrices based on ethylene vinyl acetate and polyethylene oxide, European Journal of Pharmaceutics and Biopharmaceutics 82 (2012) 526-533.

Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.

Apicella A.et al., Biomaterials, vol. 14, No. 2, pp. 83-90,1993.

Application of a modelling system in the formulation of extended release hydrophilic matrices, Reprinted from Pharmaceutical Technology Europe, Jul. 2006.

Application of Opadry II, complete film coating system, on metformin HCI extended release matrices containing Polyox water soluble resin, Coloron Apr. 2009.

(56) References Cited

OTHER PUBLICATIONS

Arnold C., "Teen Abuse of Painkiller OxyContin on the Rise," www.npr.org, Dec. 19, 2005.
Augustine, R.L., Catalytic Hydrogenation of a, B-Unsaturated Ketones. III The Effect of Quantity and Type of Catalysts, J. Org Chem. 28(1), pp. 152-155, Abstract 1963.
Avis, Kenneth, Parenteral Preparations. Chapter 85. pp. 1518-1541In Remington's Pharmaceutical Sciences, 17th Ed, 1985.
Bailey, F.E., et al., "Some properties of polyethylene oxide) in aqueous solution," Journal of Applied Polymer Science, vol. 1, Issue No. 1, pp. 56-62, 1959.
Bauer et al. Lehrbuch der Pharmazeutischen Technologie. Eight Edition 2006. Stuttgart, pp. 343-352.
Bauer et al. Lehrbuch der Pharmazeutischen Technologie. Sixth Edition 1999. Stuttgart, pp. IX-XV, Table of contents. (Full English translation attached).
Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers. (Preface, Table of Content, List of Abbreviations, Explanation of Terms only).
Baum et al.,"The impact of the addition of naloxone on the use and abuse of pentazocine", Public Health Reports, Jul.-Aug. 1987, vol. 102, No. 4, p. 426-429.
Bingwen et al, 2008, p. 367. (full translation attached).
Block, Lawrence. Medicated Applications. Chapter 88. In Remington's Pharmaceutical Sciences, 17th Ed, 1985.
Braun, et al. A study of Bite Force. Part 2: Relationship to Various cephalometric Measurements. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.
Bruce et al, Properties of hot-melt extuded tablet formulations for the colonic delivery of 5-aminosalicyclic acid, European Journal of Pharmaceutics and Biopharmaceutics, 59 (2005) 85-97.
Caraballo, Journal of Controlled Release, vol. 69, pp. 345-355, 2000.
Cawello, "Parameters for Compartment-free Pharmacokinetics—Standardization of Study Design, Data Analysis and Reporting" 1999, pp. XI-XIII (table of contents).
Committee for Proprietary Medicinal Products. Note for Guidance on the Investigation of Bioavailability and Bioequivalence. 2001. pp. 1-18.
Coppens et al., "Hypromellose, Ethylcellulose, and Polyethylene Oxide Use in Hot Melt Extrusion"; Pharmaceutical Technology, 62-70, Jan. 2005.
Cornish, P. "Avoid the Crush": hazards of medication administration in patients with dysphagia or a feeding tube, CMA Media Inc., CMAJ. 172(7), pp. 871-872, 2005.
Costa et al. "Modeling and comparison of dissolution profiles"; European Journal of Pharmaceutical Scieneces 13 (2001) 123-33.
Crowley M.M. et al., "Stability of polyethylene oxide in matrix tablets prepared by hot-melt extrusion," Biomaterials 23, 2002, pp. 4241-4248.
Crowley MM, Drug Dev Ind Pharm. Sep. 2007; 33(9):909-26. (Abstract only).
Cuesov, 1999, pp. 351-352.
Dachille, P. et al., "High-Pressure Phase Transformation in Laboratory Mechanical Mixers and Mortars", Nature, vol. 186, Apr. 2, 1960, pp. 34-71.
Dachille, F. et al., "High-Pressure Phase Transformation in Laboratory Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000 (Publisher description dated Oct. 22, 2010).
Deighan, C.J. et al., Rhabdomyolysis and acute renal failure resulting from alcohol and drug buse, Q.J. Med, vol. 93, 2000, pp. 29-33.
Dejong (Pharmaceutisch Weekblad Scientific Edition) 1987, p. 24-28.
Dexheimer, Terahertz Spectroscopy: Principles and Applications (Optical Science and Engineering Series), CRC; 1 edition 2007. (Table of content only).
Dierickx et al., "Co-extrusion as manufacturing technique for fixed-dose combination mini-matrices," European Journal of Pharmaceutics and Biopharmareutics 81 (2012), 683-689.
Disanto, Anthony. Bioavailability and Bioequivalency Testing. Chapter 77. In Remington's Pharmaceutical Sciences, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly. Water Soluble-Resin 2004, pp. 1-2.
DOW Technical Data, POLYOX WSR Solid Dosage Formulation via Melt Extrusion, Feb. 2003, pp. 1-3.
Efentakis M et al. "Evaluation of High Molecular Weight Poly(Oxyethylene) (Polyox) Polymer: Studies of Row Properties and Release Rates of Furosemide and Captopril from controlled-Release hard Gelatin Capsules", Pharmaceutical Development and Technology, 5 (3), pp. 339-346, 2000.
El-Egakey, Adel et al, "Hot extruded dosage forms Part I Technology and dissolution kinetics of polymeric matrices" Pharmacerutica Acta Helvetiae, vol. 46, pp. 31-53,Mar. 19, 1970.
El-Sherbiny I.M. et al "Preparation, characterization, swelling and in vitro drug release behaviour of poly[N-acryloylglycine-chitosan] interplymeric pH and thermally-resposive hydrogels", European Polymer Journal, vol. 41, pp. 2584-2591, 2005.
Encyclopedia of Pharmaceutical Technology, Third Edition, vol. 1, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 3 edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 6, edited by James Swarbrick PharmaceuTech, Inc., Pinehurst, North Carolinia, USA (Table of Contents only), Oct. 25, 2006.
Encyclopedia of Pharmacological Technology, Informa Healthcare, 1st Ed., 1996, vol. 14 (Table of Content only).
Erskine, Jr., Clyde, Quality Assurance and Control, Chapter 83. pp. 1487-1491 in Remington's Pharmaceutical Sciences, 17th Ed, 1985.
Eudragit NE40D web page from Evonik website; downloaded Feb. 24, 2015.
Eudragit RS PO web page from Evonik website; downloaded Feb. 24, 2015.
European Pharmacopeia 5.0; Glyceryl behenate monograph; dated Jan. 2005; downloaded Feb. 24, 2015.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition, Council of Europe, Strasbourg, 1997, pp. 127-152.
European Search Report and Opinion Application No. 12002708. 1-1219, dated Sep. 24, 2012.
European Search Report and Opinion Application No. 14176277. 3-1460, dated Dec. 15, 2014.
European Search Report and Opinion, Application No. 11006253. 6-2112, dated Dec. 16, 2011.

(56) References Cited

OTHER PUBLICATIONS

European Search Report and Opinion, Application No. 11006254.4-2112, dated Dec. 16, 2011.
European Search Report and Opinion, Application No. 11008131.2-1219, dated Feb. 24, 2012.
European Search Report and Opinion, Application No. 11009129.5-2112, dated Apr. 10, 2012.
European Search Report and Opinion, Application No. 12001296.8-1219, dated Jun. 26, 2012.
European Search Report and Opinion, Application No. 12001301.6-1219, dated Jun. 26, 2012.
European Search Report and Opinion, Application No. 12003743.7-1219, dated Sep. 24, 2012.
European Search Report and Written Opinion for EP Application No. 13169658.5, dated Aug. 6, 2013.
European Search Report and Written Opinion for EP Application No. 13169659.3, dated Aug. 6, 2013.
European Search Report and Written Opinion for EP Application No. 13176309.9-1460, dated Oct. 9, 2013.
European Search Report and Written Opinion for EP Application No. 14169801.9-1455 dated Oct. 20, 2014.
Evaluation of Verapamil HCI (240 mg) Extended Release Matrix Formulation Using USP Apparatus III in Biorelevant Dissolution Media, Jul. 2009.
Evonik Industries, Eudragit Appiication Guidelines, 10th Edition, 2008, (Table of Contents only).
Extended European Search Report and Opinion for Application No. EP 15153679.4-1455, dated Jun 30, 2015.
Extended European Search Report and Opinion for Application No. EP 15165064.5-1455, dated Oct. 16, 2015.
Extended European Search Report and Opinion for Application No. EP 15165065.2-1455, dated Nov. 2, 2015.
Extended European Search Report and Opinion for Application No. EP 15165067.8-1455, dated Nov. 2, 2015.
Extended European Search Report and Opinion for Application No. EP 15165069.4-1455, dated Nov. 2, 2015.
Extended European Search Report and Opinion for Application No. EP 15165070.2-1455, dated Nov. 2, 2015.
Fell J.T., et al, "Determination of Tablet Strength by the Diametral-Compression Test" Journal of Pharmaceutical Sciences, vol. 59, No. 5, May 1970, pp. 688-691.
Follonier N. et al., "Evaluation of hot-melt extrusion as a new technique for the production of polymer-based pellets for sustained release capsules containing high loadings of freely soluble drugs," Drug Development and Industrial Pharmacy, 20(8), pp. 1323-1339, 1994.
Follonier N. et al., "Various ways of modulating the release of dltiazem hydrochloride from hot-melt extruded sustained release pellets prepared using polymeric materials" Journal of Controlled Release 36, pp. 243-250, 1995.
Formulation of Polyox ER Matrices for a Highly Soluble Active, Colorcon Jul. 2009.
Foye, W., Principles of Medicinal Chemistry; Analgesics pp. 241-242, at 241 (1989).
Foye, W., Principles of Medicinal Chemistry; Structural Features and Pharmacologic Activity, pp. 63-66 at 65 (1989).
Freed et al., "pH Control of Nucleophilic/electrophilic oxidation", International Journal of Pharmaceutics, vol. 357, pp. 180-188 (2008).
Giles R. et al. Plastic Packaging Materials. Chapter 81. pp. 1473-1477 In Remington's Pharmaceutical Sciences, 17th Ed, 1985.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Graham N.B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Guidance for Industry—Statistical Approaches to Establishing Bioequivalence, FDA, BP, Jan. 2001.
Handbook of Pharmaceutical Excipients, 1986, American Pharmaceutical Association, Washington, DC and London (Table of Content Only).
Handbuch der Kunststoff-Extrusionstechnik 1, "Grundlagen" in Chapter 1.2 "Klassifizierung von Extrudern", pp. 3-7, 1989. (Full english translation attached).
Hanning C.D.et al. "The Morphone Hydrogel Suppository. A New Sustained release Rectal Preparation", British Journal of Anaesthesia, 61, pp. 221-227, 1988.
Hartauer, Kerry J. "Influence of Peroxide Impurities in Povidone and Crospovidone on the Stability of Raloxife" Pharma. Dev. & Tech, 5 (3) 303-310 (2000).
Henriest D. et al. In vitro and in vivo evaluation of starch-based hot stage extruded double matrix systems. Journal of Controlled Release. 2001, vol. 75, pp. 391-400.
Hoepfner et al, Fiedler Encyclopedia of Excipients. Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int .J. Pharmacol. 2008, vol. 356, pp. 121-129.
Inert gas—Wikipedia. Dec. 2009, pp. 1-3.
Investigation of a Directly Compressible Metformin HCI 500mg Extended Release Formulation Based on Hypromelilose, Colorcon Jul. 2009.
James, A. "The legal and clinical implications of crushing tablet medication", Nurse Times 100(50), 28-33, 2004.
Janicki S. et al. "Slow-Release Microballs: Method of Preparation", Acta Pharm. Technol. 33 (3) 154-155, 1987.
Kalant et al., Death in Amphetamine Users: Caues and Rates, CMA Journal, vol. 112 (Feb. 8, 1975): 299-304.
Katz N. et al. "Challenges in the development of prescription opioid abuse-deterrent formulations", Clin. J. Pain, 23(8): 648-660 (Oct. 2007).
Kim C.-J. "Drug Release from Compressed Hydrophilic Polyox-WSR Tablets" J Pharm. Sciences 1995, 84(3): 303-306.
Kim N et al. "Preparation and Evaluation of Eudragit Gels. V. Rectal Gel Preparations for Sustained Release and Avoidance of First-Pass Metabolism of Lidocaine", Chem. Pharm Bull. 1992, 40(10), 2800-2804.
King et al. Oral Solid Dosage Forms. Chapter 90. pp. 163-1632 In Remington's Pharmaceutical Sciences, 17th Ed, 1985.
King, R, "Tablets, Capsules, and Pills" Remington's Pharmaceutical Sciences, pp. 1553-1593, Ch. 89, 1980, $16^{th}$ Edition.
King, Remington's Pharmaceutical Sciences 17th ed., Chapter 78, p. 1418 (1985).
Knevel, Adelbert. Separation. Chapter 78. pp. 1432-1442 In Remington's Pharmaceutical Sciences, 17th Ed, 1985.
Lee, Y.-S. et al., Principles of Terahertz Science and Technology (Lecture Notes in Physics), Springer; 1 edition 2008. (Table of Contents Only).
Levina et al., "The Effect of Ultrasonic Vibration on the Compaction Characteristics of Ibuprofen" Drug Develoroent and Industrial Pharmacy, vol. 28, No. 5, pp. 495-514, 2002.
Levina M. et al "The Effect of Ultrasonic Vibration on the Compaction Characteristics of Paracetamol" Journal of Pharmaceutical Sciences, vol. 89, No. 6, pp. 705-723, Jun. 2000.
Lieberman, Herbert A., Pharmaceutical Dosage Forms, Tablets, Second Edition, Revised and Expanded, 1990. vol. 2 (Cover and Table of Content only).
Lintner, Carl. Stability of Pharmaceutical Products. Chapter 82. pp. 1478-1486 In Remington's Pharmaceutical Sciences, 17th Ed, 1985.

(56) References Cited

OTHER PUBLICATIONS

Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Pharmaceuticals and Health Care Products"; Blackie Academic & Professional; First Edition 1996. (Table of contents only).
Longer et al. Sustained-Release Drug Delivery Systems. Chapter 92. pp. 1611-1661 In Remington's Pharmaceutical Sciences, 17th Ed, 1985.
Madorsky S.L. "Thermal degradation of Polyethylene Oxide and Polypropylene Oxide", Journal of Polymer Science, pp. 183-194 vol. 36, No. 3, Mar. 1959.
Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Maggi, C., Therapeutic Potential of Capsaicin-like Molecules, Life Sciences, vol. 51, pp. 1777-1781, 1992.
Mank R. et al., "Darstellung wirkstoffhaltiger Extrusionsormlinge auf der Basis von Thermoplasten. Teil 1: Untersuchung zur Wirkstoffliberation" Pharmazie 44, H. 11, pp. 773-776, 1989. English language translation of relevant paragraph provided.
Mank R., "Darstellung wirkstoffhaltiger Extrusionsformlinge auf der Basis von Thermoplasten, Teil 2: Unersuchungen zur Optimierung der Wirkstofffreigabe" Pharmazie 45, H. 8, pp. 592-593 1990. English language translation of relevant paragraph provided.
Marques, Tablet breaking force, 2008.
Matos, Dr. Rick, Ph.D—Letter Jan. 6, 2011.
McGary, C,W.. Jr. "Degradation of Poly(ethylene Oxide)", Journal of Polymer Science vol. XLVI,1960, pp. 51-57.
McGinity et al., Hot-Melt Extrusion as a Pharmaceutical Process, American Pharmaceutical Review, vol. 4 (2), pp. 25-36, 2001.
McGinity, J.W.—Letter of Jan. 26, 2009, pp. 1-4.
McNeill M. et al. Properties controlling the diffusion and release of water-soluble solutes from poly(ethylene oxide) hydrogels, 4. Extended constant rate release from partly-coated spheres. Journal Biomat. Sci. Polymer. Ed. 1996, Ed. 1996, vol. 7, pp. 953-963.
Mesiha M.S. et al "A Screening Study of Lubricants in Wet Powder Passes Suitable for extrusio-spheronization", Drug Development and Industrial Pharmacy, 19(8), pp. 943-959, 1993.
Metformin Hydrochloride 1000 mg Extended Release Tablets, Lubrizol Advanced Materials, Inc., Nov. 20, 2009, Previous Edition Dec. 19, 2008.
Metformin Hydrochloride 750 mg Extended Release Tablets, Lubrizol Advanced Materials, Inc., Sep. 2010.
Miles, R.E. et al., Terahertz Frequency Detection and Identification of Materials and Objects (NATO Science for Peace and Security Series B: Physics and Biophysics), Springer; 1 edition 2007, (Table of contents).
Miller "To crush or not to crush? What to consider before giving medications to a patient with a tube or who has trouble swallowing", Nursing, pp. 50-52, Feb. 2000.
Mises à jour cumulatives, Vidal, Jan./Oct. 2002 (full translation attached).
Mitchell, "Oral Dosage Forms That Should Not Be Crushed: 2000 Update" Hospital Pharmacy 35(5), 553-557, 2000.
Monolithic: retrieved from internet: http:/merriam-webster.com/dictionary/monolithic. Retrieved on Sep. 2, 2015.
Moorman-Li, R. et al, "A Review of Abuse-Deterrent Opioids for Chronic Nonmalignant Pain." Pharmacy and Therapeutics, vol. 37 No. 7, Jul. 2012, pp. 412-421.
Moroni A. et al, "Application of Poly(Oxyethylene) Homopolymers in Sustained release Solid formulations" Drug Development and Industrial Pharmacy, 21(12) pp. 1411-1428, 1995.
Mullins, John. Ophthalmic Preparations. Chapter 87. pp. 1553-1563; In Remington's Pharmaceutical Sciences, 17th Ed, 1985.
Munjal M. et al., "Polymeric Systems for Amorphous Delta$^\wedge$9—Tetrahydrocannabinol Produced by a Hot-Melt Method, Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Nairn, J.G., Solutions, Emulsion, Suspensions and Extractives. Chapter 84. pp. 1492-1517, In Remington's Pharmaceutical Sciences, 17th Ed, 1985.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/1401/98).
Ohnishi N. et al., Effect of the Molecular Weight of Polyethylene Glycol on the Bioavailability of Indomethacin Sustained-Release suppoositories Prepared with Solid Dispersion, Chem. Pharm. Bull, 35(8), pp. 3511-3515, 1987.
Oliveira et al., "Production and characterization of laminar coextrudates at room temperature in the absence of solvents," AAPS Annual Meeting and Exposition, Oct. 14-18, 2012, Chicago, USA.
Oxycodon (Oxygesic): Missbrauch, Abhaengigkeit und toedliche Folgen durch Injection zerstossener Retardtabletten, Deutsches Ärzteblatt, vol. 36, A2326-A2326, Sep. 5, 2003.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.
Ozeki T. et al. "Controlled Release From Solid Dispersion Composed of Polyethylene oxide)-Carbopol Interpolymer Complex With Various Cross-Linking Degrees of Carbopol", Journal of Controlled Release. 63, 2000. pp. 287-295.
Ozeki T. et al., "Control of medicine release from solid dispersion composed of the poly(ethylene oxide)-carboxyviylpolymer interpolymer complex by varying molecular wight of poly(ethylene oxide)" Journal of Controlled Release 58, pp. 87-95, 1999.
PCT International Search Report and Written Opinion for PCT Application No. PCT/EP2010/004459 dated Dec. 1, 2010.
PCT International Search Report and Written Opinion for PCT Appication No. PCT/EP2009/003290 dated Jul. 9, 2009.
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2013/059728 dated Aug. 6, 2013.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 21, 2015.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hyrdrophilic furosemide matrices, International Journal of Pharmaceutics, 67 (1991) 113-121.
Pharm. Research, Official Journal of the American Association of Pharmaceutical Scientists, Sep. 1989, 6(9), S-98.
Pharm. Research, Official Journal of the American Association of Pharmaceutical Scientists, Oct. 1991, 8(10), S-192.
Phillips, G. Briggs. Sterilization, Chapter 79. pp. 1443-1454, In Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives from a simple monolithic system. Journal of Controlled Release. 2000, vol. 67, pp. 67-78.
Pinto, Joao F. et al.,"Evaluation of the Potential Use of Polyethylene oxide) as Tablet- and Extrudate-Forming Material," AAPS PharmSci, 2004; 6 (2), Article 15, pp. 1-10, (http://www.aapspharmsci.org).

(56) References Cited

OTHER PUBLICATIONS

Prininger, O.G.and A.L. Baner, Plastic Packaging: Interactions with Food and Pharmaceuticals, Wiley VCH, 2nd Completely Revised Edition Feb. 13, 2008. (Table of Contents only).
Polyox water soluble resins 2003. http://www.dow.com/webapps/lit/litorder.asp?filepath=polyox/pdfs/noreg/326-00002.pdf.
Polyox water-soluble resins (DOW Mar. 2002); see http://msdssearch.dow.com/PublishedLiteratureDOWCOM/dh_0031/0901b80380031a4a.pdf?filepath=/326-00001.pdf&fromPage=GetDoc.
Porter, S. Coating of Pharmaceutical Dosage Forms. Chapter 91. pp. 1633-1643 In Remington's Pharmaceutical Sciences, 17th Ed, 1985.
Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. et al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain Medications; FDA Cites Patient Needs as First Priority; New Drug Application Delayed," www.headaches.about.com, Jun. 18, 2002, pp. 1-6.
Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Radko S.et al., Applied ad Theoretical Electrophoresis 5, pp. 79-88, 1995.
Ravin, L. Preformulation. Chapter 76, pp. 1409-1423, In Remington's Pharmaceutical Sciences, 17th Ed, 1985.
Remington, The Science and Practice of Pharmacy, 19th ed., vol. II, p. 1457 (1995) (providing a table of DFA-approved commercially marketed salts).
Repka M. et al., Bioadhesive Properties of Hydroxypropylcellulose Topical Films Produced by Hot-Melt Extrusion, Journal of Controlled Release, 70 (2001), pp. 341-351.
Repka MA, Drug Dev Ind Pharm. Oct. 2007; 33(10):1043. (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58, No. 4, pp. 428-431, Apr. 1969.
Rippe, E. Powders, Chapter 89, pp. 1585-1602, In Remington's Pharmaceutical Sciences, 17th Ed, 1985.
Ritschel et al. Die Tablette: Handbuch der Entwicklung, Herstellung und Qualitatssicherung. 2nd Edition, 2002, Ch 6, pp. 515-519. (Full English translation attached).
Ritschel et al. Die Tablette: Handbuch der Entwicklung, Herstellung und Qualitatssicherung, 2nd Edition, 2002, Ch 6, pp. 69-82 and 115-136.
Ritschel et al. Die Tablette: Handbuch der Entwicklung, Herstellung und Qualitatssicherung. 2nd Edition, 2002, Table of content.
Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2013), pp. 1250-1258.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Salomies et al., "Determination of Oxycodone Hydrochloride in Oral Solutions by High-Performance Thin-Layer Chromatography/Densitometry," Journal of AOAC International, 83: 1497-1501 (2000).
Sax et al., Hawley's Condensed Chemical Dictionary, 11th ed., 1987, p. 1233, definition of "wax".

Scheirs J., et al."Characterizing the Solid-State Thermal Oxidation of Poly (ethylene oxide) Powder", pp. 2014-2019, Polymer, vol. 32, No. 11, 1991.
Schier et al. "Fatality from Administration of Labetalol and Crushed Extended-Release Nifedipine" The Annals of Pharmacotherpay vol. 37, 1420-1423, Oct. 2003.
Schroeder J., et al. Granulierung hydrophober Wirkstoffe im Planetwalzenextruder, Pharm. Ind. 2003, vol. 65, No. 4, 367-372. (Full English translation attached).
Sciarra et al. Aerosols. Chapter 93., pp. 1662-1677, In Remington's Pharmaceutical Sciences, 17th Ed, 1985.
Search result conducted on http://www.unitconversion.org/force/newtons-to-kiloponds-convresion.html, on Jul. 5, 2011 (Conversion of 18.8 kiloponds to newtons).
Shivanand P et al., "Factors Affecting Release of KCl From Melt extruded Polyethylene Disks", Pharmaceutical Research, Oct. 1991, vol. 8, No. 10, p. S-192.
Sidhu et al., "Watch for nonpsychotropics causing psychiatric side effects," Current Psychiatry, vol. 7, No. 4, 2008, 61-74.
Siegel, P. Tonicity, Osmoticity, Osmolality, and Osmolarity. Chapter 80. pp. 1454-1472 In Remington's Pharmaceutical Sciences, 17th Ed, 1985.
Spassov et al., Stereochemistry of Diastereomeric 3-Dialkylaminopropanols and O-Derivatives, J.f. prakt. Chemie, 323:5, 793-800 (1981).
Sprockel O.L et al. "Permeability of Cellulose Polymers: Water Vapour Transmission Rates"., J. Pharma Pharmacol. 42, pp. 152-157, 1990.
Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Stafford J., überzogene feste Formen, 1991, 347-68, (English translation attached).
Strang, Abuse of buprenorphie (Temgesic) by snorting, Letter to the editor, British Med. J., 302: 969 (1991).
Stringer J.L., et al "Diffusion of small molecular weight drugs in radiation-crosslinked poly(ethylene oxide) hydrogels", Journal of Controlled Release 42, pp. 195-202, 1996.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.

(56) References Cited

OTHER PUBLICATIONS

Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Tablet, www.docstoc.com (2011).
Third Party Observations filed with EPO for Patent EP658055B1, Feb. 2, 2009, pp. 1-8.
Thoma V.K. et al. "Bestimmung der In-vitro-Freigabe von schwach basischen Wirkstoffen aus Ratardarzneiformen", pp. 299-301, Pharm. Ind. 51, Nr. 3, 1989.
Tikhonov, A. et al, Biopharmacy. The Manual for Students of Pharmaceutical Universities and Departments, 2003, pp. 40-41, Kharkov, Ukraine (Full English translation attached).
Tipler, et al, Physics for Scientists and Engineers, vol. I, 6th Edition, pp. 234-235, 2003.
Tompkins et al., "Human abuse liability assessment of oxycodone combined with ultra-low-dose natrexone," Psychopharma., 210: 471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures. Chapter 86. pp. 1542-1552, In Remington's Pharmaceutical Sciences, 17th Ed, 1985.
US Pharmacopoeia, Chapter 1217, Aug. 12, 2008.
Varma et al, Factors Affecting Mechanism and Kinetics of Drug Release from Matrix-Based Oral Controlled Drug Delivery Systems, Am. J. Drug Deliv. 2004: 2 (1): 43-57.
Verhoeven et al., "Influence of polyethylene glycol/polyethylene oxide on the release characteristics of sustained-release ethylcellulose mini-matrices produced by hot-melt extrusion; in vitro and in vivo evaluations," European Journal of Pharmaceutics and Biopharmaceutics 72 (2009) 463-470.
Vippagunta et al., 2006, 3-26.
Vynckier et al.,"Hot-melt co-extrusion for the production of fixed-dose combination products with a controlled release ethylcellulose matrix core," International Journal of Pharmaceutics 464 (2014), 65-74.
Wade and Weller, "Handbook of Pharmaceutical Excipients: 2nd Edition", The American Pharmaceutical Association and the Pharmaceutical Press, Washington and London, Table of Contents pp. v-vi, 1994.
Wagner, Pharmazeutisch Biologie—Drogen und ihre Inhaltsstoffe—Scharfstoffdrogen, 2nd., revised edition, Gustav Fischer Verlag, Stuttgart-N.Y., 1982, pp. 82-92 (Full English Translation attached).
Wagner, Pharmazeutische Biologie—Drogen und ihre Inhaltsstoffe—Scharfstoffdrogen, 2nd., revised edition, Gustav Fischer Verlag, Stuttgart-N.Y., 1982,Table of Content.
Waltimo, et al, "A novel bite force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", Acta Odontol Scand 53 (1995): 254-258.
Waterman et al., "Stabilization of Pharmaceuticals to Oxidative Degradation", Pharmaceutical Development and Technology, vol. 7(1), pp. 1-32, (2002).
Waters et al., "Intravenous Quetiapine-Cocaine Use ("Q-Ball")", Letter to the Editor, Am. J. Psychiatry, 164(1): pp. 173-174 (2007).
Weiss, U., "Derivatives of Morphine, | 14-Dihydroxydihydromorphinone," J. Am. Chem. Soc. 77, pp. 5891-5892, Nov. 20, 1955.
West, Anthony R., Solid state chemistry and its applications, Wiley, New York, 1988, pp. 358 and 365.
Woodburn, K.R. et al., Vascular complications of injecting drug misuse, Br. J. of Surgery, vol. 83, 1996, pp. 1329-1334.

Wu N, et al. Mathematical modeling and in vitro study of controlled drug release via a highly swellable and dissoluble polymer matrix: polyethylene oxide with high molecular weights, J Control Release. Feb. 16, 2005;102(3):569-581.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Yarbrough et al, Letters to Nature "Extraordinary effects of mortar-and-pestle grinding on microstructure of sintered alumina gel", Nature 322, pp. 347-349 (Abstract only) (Jul. 24, 1986).
Yeh et al., Stability of Morphine in Aqueous Solution III: Kinetics of Morphine Degradation in Aqueous Solution, Wiley Subscription Services, Inc., Journal of Pharmaceutical Sciences, 50(1):35-42 (1961).
Zeeshan, F and N. Bukhari, "Development and Evaluation of a Novel Modified-Release Pellet-Based Tablet System for the Delivery of Loratadine and Pseudophedrine Hydrochloride as Model Drugs," AAPS PharmaSciTech 11(2); 910-916 (available on-line May 22, 2010).
Zhang et al., "Properties of Sustained-Release Tablets Prepared by Hot-Melt Extrusion" Pharmaceutical Development and Technology, 1999, 4(2), 241-250.
Carbopol 71G, retrieved Mar. 10, 2014 from http://www.lubrizol.com/LifeScience/Products/Carbopol71G-NF.html.
Eggleston, "The seat of the emetic action of various drugs," J. Pharmacol. Exp. Ther. 7, 225-253 (1915).
European Search Report and Written Opinion for EP Application No. 13197503.9-1460, dated Feb. 18, 2014.
European Search Report and Written Opinion for EP Application No. 13425151.1-1460, dated Mar. 11, 2014.
Evonik Rohm GmbH product brochure: EUDRAGIT acrylic polymers for solid oral dosage forms (2009).
Gryczke et al, "Development and evaluation of orally disintegrating tablets (ODTs) containing Ibuprofen granules prepared by hot melt extrusion", Colloids and surfaces., B, Biointerfaces, Elsevier, Amsteram, NL, vol. 86, No. 2, Apr. 5, 2011, pp. 275-284.
Jannetto, P. et al, "Oxycodone: Recognition and Pharmacogenomics," Toxicology News, Mar. 2003, 1-7.
Kolter, K., "Compression Behaviour of Koffidon SR," APV/ APGI 2002, Florence, Apr. 11, 2002.
Kondrat, T. , "Technology dosage forms" Moscow 1991, p. 96.
Lenindzer, A., "The molecular basis of the structure and functions of cells" Moscow 1974, p. 68.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Morissette et al. Advanced Drug Delivery Review 26 (2004), 275-300.
Oxicotin: Balancing Risks and Benefits, United States Senate, Hearing, Feb. 12, 2002.
PCT International Search Report and Written Opinion for PCT Application No. PCT/EP2014/064830 dated Aug. 6, 2014.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Polyox WSR-303, retrieved Mar. 10, 2014 from URL http://www.dow.com/dowwolff/en/industrial_solutions/polymers/polyethylene.
Polyox, Colorcon, Application Data (Apr. 2009) downloaded from http://www.colorcon.com/literature/marketing/mr/Extended%20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.
Silver, J. "Painkiller OxyContin most commonly abused prescription drug on the streets of Western Pennsylvania", Pittsburg Post-Gazette, Apr. 8, 2001.

(56) References Cited

OTHER PUBLICATIONS

Vippagunta et al. Crystalline Solids, Advanced Drug Delivery Review 48 (2001), 3-26.
Wikipedia-Dextromethorphan Aug. 12, 2013 (and attached related English-language entry dated Dec. 11, 2013).
Borquist et al., "Simulation of the release from a multiparticulate system validated by single pellet and dose release experiements," J. Controlled Release, 97: 453-465 (2004).
Chibuzor et al. "Formulation Development and Evaluation of Drug Release Kinetics from Colon-Targeted Ibuprofen Tablets Based on Eudragit RL 100-Chitosan Interpolyelectrolyte Complexes," Hindawi Publ. Corporation ISRN Pharmaceutics, vol. 2013, Article ID 838403.
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Verhoeven, et al. "Xanthan gum to tailor drug release of sustained-release ethylcellulose mini-matrices prepared via hotmelt extrusion: in vitro and in vivo evaluation," European Journal of Pharmaceutics and Biopharmaceutics, 63 (2006) 320-330.
USP Expert Council, US Pharmacopoeia, Chapter 1092, 2007, 1-15.
Dabbagh, et al. "Release of Propranolol Hydrochloride from Matrix Tablets Containing Sodium Carboxymethylcellulose and Hydroxypropylmethylcellulose"; 1999; Pharmaceutical Development and Technology, 4(3), 313-324.
Baxter, J.L. et al., "Hydrodynamics-induced variability in the USP apparatus II dissolution test," International Journal of Pharmaceutics 292 (2005) 17-28.
Bellmann et al., "Development of an advanced in vitro model of the stomach and its evaluation versus human gastric psychology." Food Research International 88 (2016) 191-198.
Koziolek, M. et al., "Development of a bio-relevant dissolution test device simulating mechanical aspects present in the fed stomach," European Journal of Pharmaceutical Sciences 57 (2014) 250-256.
Remington, Chapter 45, pp. 996-1035. (Full Translation Attached).
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.
M. Xu et al., "Evaluation of the coat quality of sustained release pellets by individual pellet dissolution methodology," Int. J. Pharm. 478 (2015) 318-327.
Fathima, N. et al. "Drug-excipient interaction and its importance in dosage form development," Journal of Applied Pharmaceutical Science 01 (06); 2011, pp. 66-71.
Starch 1500, Partially Pregelatinized Maize Starch, technical data from Colorcon, Februa 2016, 6 pages.
Remington, Chapter 45, pp. 996-1035.
Extended European Search Report for Application No. EP 16183922. 0-1460, Oct. 31, 2016.
Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.
Schilling, et al., "Novel application of hot-melt extrusion for the preparation of monolithic matrices containing enteric-coated particles," International Journal of Pharmaceutics 400 (2010) 34-31.
Starch 1500, Partially Pregelatinized Maize Starch, technical data from Colorcon, Feb. 2016, 6 pages.
Decision of the United States District Court for the Southern District of New York, in in re *Endo Pharmaceuticals Inc. and Grünenthal GmbH* v. *Amneal Pharmaceuticals, LLC et al.*, Findings of Fact and Conclusions of Law, District Judge Thomas P. Griesa, New York, New York, Jan. 14, 2015.
Decision of the United States District Court for the Southern District of New York, in in re Oxycontin Antitrust Litigation, *Purdue Pharma LP* v. *Teva Pharmaceuticals*, Findings of Fact and Conclusions of Law, District Judge Sidney H. Stein, New York, New York, Jan. 14, 2014.
U.S. Court of Appeals, Federal Circuit, *Purdue Pharma L.P.* v. *Epic Pharma, LLC*, 117 USPQ2d 1733 (Fed. Cir. 2016).

Al-Angari, A. et al. "The compaction properties of polyethylene glycols," J Pharm. Pharmacol. (1985) 37:151-153.
Al-Nasassrah et al., "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 28:2944-54 (1995).
Back, D.M. et al., "Ethylene Oxide Polymers", in Kirk-Othmer Encyclopedia of Chemical Technology. 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.
Balogh, E., "Tastes in and Tastes of Paprika," in Taste: Proceedings of the Oxford Symposium on Food and Cookery 28 (Tom Jaine Ed.) 1988, pp. 25-40.
Baumann, T., "Pain Management," Pharmacotherapy: A Pathophysiologic Approach (J.T. DiPiro et al. eds., McGraw-Hill 4th ed. 1999), Ch. 56, 1014-1026.
Baumrucker, S.J., "OxyContin, the Media, and Law Enforcement", American Journal of Hospice & Palliative Care, 18:3 (May/Jun. 2001), 154-156.
Choi, S., et al., "Development of a Directly Compressible Poly(Ethylene Oxide) Matrix or the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with Polyethylene Oxide by Direct Compression," Proceedings of the $29^{th}$ Annual Meeting of the Controlled Release Society, in collaboration with the Korea Society for Biomaterials, Minneapolis, $1^{st}$ Edition, 2002, 984-985.
Ciccone, P. E., "Attempted Abuse of Concerta," Letters to the Editor, J. Am. Acad. Child Adolesc. Psychiatry, 41:7 (Jul. 2002).
Controversies in ADHD: A Breakfast Symposium—Concerta.
Crowley, M. et al., Pharmaceutical Applications of Hot-Melt Extrusion: Part I. Drug Dev. & Indus. Pharmacy (2007) 33:909-926.
Crowley, M. et al., "Properties of Hot-Melt Extruded CPM Tablets Using Hydrophilic Polymers," poster presentation, (2000).
Crowley, M., "Physicochemical and Mechanical Characterization of Hot-Melt Extruded Dosage Forms." Dissertation presented to the Faculty of the Graduate School of the University of Texas at Austin. (May 2003).
Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).
CROWLEY0000001—CROWLEY0000127.
Davies, N. "Sustained Release and Enteric Coated NSAIDs: Are They Really GI Safe?" J. Pharm. & Pharmaceut. Sci., 2(1):5-14, 1999.
Declaration of Dr. James W. McGinity, dated Oct. 28, 2009; online, retrieved from: http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l J Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun. 2002, 28 & 30.
Dow, "Material Safety Data Sheet: POLYOX(TM) WSR 30" (effective date: Sep. 18, 2001).
Dow, "POLYOX Water-Soluble Resins: Degradation of Water-Soluble Resins," Technical Data (Oct. 2002).
Drug Bank "Oxymorphone," 2015; online, available at: www.dmgbank.ca/chugs/db01192 printed Jul. 1, 2015.
*Endo Pharmaceuticals Inc.* v. *Teva Pharmaceuticals USA, Inc.* (S.D.N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.

(56) References Cited

OTHER PUBLICATIONS

FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.
Final Draft Labeling for Concerta Extended-Release Tablets Attachment to Approval Letter (2000); available at: http://www.accessdata.fda.gov/drugsatfda_docs/label/2000/21121lbl.pdf.
Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.
Huang, H. et al., "Preparation of Controlled Release Oral Dosage Forms by Low Temperature Melt Extrusion," AAPS PharmSci. 2000 2(S1).
Jaffe, S.L., "Failed Attempts at Intranasal Abuse of Concerta," Letters to the Editor, J. Am. Acad. Child Adolesc. Psychiatry, 41:1 (Jan. 2002).
Jannsen Pharmaceuticals, Inc. Concerta Labeling Revisioins, Dec. 12, 2013; online, retrieved from: http://www.accessdata.fda.gov/dmgsatfda_docs/labeV2013/021121s032lbl.pdf.
Joint Claim Construction and Prehearing Statement, dated Jul. 11, 2014. *Janssen Pharmaceuticals, Inc. and Grünenthal GMBH* v. *Actavis Elizabeth LLC and Alkem Laboratories Limited*, Civil Action No. 2:13-cv-04507 CCC-MF (D.N.J.), *Janssen Pharmaceuticals, Inc. and Grünenthal GMBH* v. *Roxane Laboratories, Inc.*, Civil Action No. 2:13-cv-06929 CCC-MF (D.N.J.), and *Janssen Pharmaceuticals, Inc. and Grünenthal GMBH* v. *Alkem Laboratories Limited*, Civil Action No. 2:13-cv-07803 CCC-MF (D.N.J.).
Kibbe, Coloring Agents, in Handbook of Pharmaceutical Excipients (3d ed. 2000).
Kidokoro, M. et al.,"Properties of Tablets Containing Granulations of Ibuprofen and Acrylic Copolymers Prepared by Thermal Processes," Pharm Dev. and Tech. , 6:263-275 (2001).
Kinjo, N. et al, "Antiplasticization in the Slightly Plasticized Poly(vinyl chloride)," Polymer Journal 4(2):143-153 (1973).
Larhib, H. et al., "Compressing polyethyelene glycols: the effect of compression pressure and speed," Int 'l J Pharmaceutics (1997) 147: 199-205.
Lieberman, H., et al., Pharmaceutical Dosage Forms: Tablets, vol. 2, Ch. 5: Granulation Technology and Tablet Characterization (1990), Table of contents and 245-348.
Lyons et al., "Twitch Interpolation in the Assessment of the Maximum Force-Generating Capacity of the Jaw-Closing Muscles in Man," Arch. Oral. Biol. 41:12, 1161-1168 (1996).
Makki, A, et. al., Eds., A Dictionary of American Idioms, 4th Ed. Barron's, New York (2004), 342-343.
Markovitz, H., et al. "Calculations of Entanglement Coupling Spacings in Linear Polymers." Journal of Physical Chemistry, 1962. 66(8): 1567-1568.
McCrum, N., et al., Principles of Polymer Engineering. 2nd ed., New York: Oxford University Press. 447(1997), Chapter 7, 296-351.
McGinity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chapter 10, 183-208.
McQuay, H. et a. "Methods of Therapeutic Trials," Textbook of Pain 1125-1138 (P.D. Wall & R. Melzack eds., Elsevier 4th ed. 1999), Table of Contents and 1125-1138.
Miura et al., "Comparison of Maximum Bite Force and Dentate Status Between Healthy and Frail Elderly Persons," J. Oral Rehabilitation, vol. 28 (2001), pp. 592-595.
Miyagawa, Y. et al., "Controlled-release of diclofenac sodium from wax matrix granulate," Int 'l J. Pharmaceutics (1996) 138:215-224.
National Drug Intelligence Center Information Bulletin "OxyContin Diversion and Abuse" Jan. 2001.
Payne, H. et al., Denatonium Benzoate as a Bitter Aversive Additive in Ethylene Glycol and Methanol-Based Automotive Products, SAE Technical Paper 930589, abstract (1993).
Pilpel, N., et al. "The effect of temperature on the tensile strength and disintegration of paracetamol and oxytetracylcine tablets," J Pharm Pharmac., 29:389-392 (1977).
Polyox Water-Soluble Resins NF in Pharmaceutical Applications, Dow Chemical Company, Aug. 2002.
Purdue Pharma LP Material Safety Data Sheet, OxyContin Tablets, 10 mg, 15 mg, 20 mg, 30 mg, 40 mg, 60 mg, Version Sep. 16, 2010; available at www.purduephruma.com/msdss/oxcontin_msds.pdf.
Rauwendaal, Chris, PHD, Responsive Expert Report of Chris Rauwendaal, Ph.D. Regarding Expert Report of Michael M. Crowley, Ph.D., dated Jul. 17, 2015.
Repka, M. et al. Pharmaceutical Applications of Hot-Melt Extrusion: Part II. Drug Dev. & Indus. Pharmacy (2007) 33:1043-1057.
Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.
Seitz, J.A.; et al., "Evaluation of the Physical Properties of Compressed Tablets 1: Tablet Hardness and Friability," J. of Pharm. Sci. , 54:1353-1357 (1965).
Shah, et al., "Some Effects of Humidity and Heat on the Tableting Properties of Microcrystalline Cellulose Formulations 1," J. of Pharm. Sci., 57:181-182 (1967).
Singhal, et al., Handbook of Indices of Food Quality and Authenticity (1997), "Capsicum" p. 398-299.
Smith, K.L. et al. "High Molecular Weight Polymers of Ethylene Oxide—Plastic Properties." Industrial and Engineering Chemistry, 1958. 50(1): 12-16.
Tapentadol Pre-Review Report, Expert Committee on Drug Dependency Thirty-Fifth Meeting Hammamet, Tunisia, Jun. 4-8, 2012, available at http ://www.who.int/medicines/areas/quality_safety/5.2Tapentadolpre-review.pdf.
Tiwari, D., et al., "Evaluation of polyoxyethylene homopolymers for buccal bioadhesive drug delivery device formulations." AAPS Pharmsci, 1999. 1(3): Article 13.
Wilkins, J.N., "Pharmacotherapy of Schizophrenia Patients with Comorbid Substance Abuse," Schizophrenia Bulletin, 23:215-228 (1997).
World Health Org., Cancer Pain Relief With a Guide to Opioid Availability (2d ed. 1996).
Yin, T.P., et al., "Viscoelastic Properties of Polyethylene Oxide in Rubber-Like State." Journal of Physical Chemistry, 1961. 65(3): 534-538.
Zacny, J. et al. Drug & Alcohol Dependence (2003) 69:215-232.
Zhang, F., "Hot-Melt Extrusion as a Novel Technology to Prepare Sustained-Release Dosage Forms" Dissertation University of Texas at Austin, Dec. 1999.
Efentakis et al, Effects of Excipients on Swellin and Drug Release from Compressed Matrices, in Drug Development and Industrial Pharmacy 23(1):107-112, Jan. 1997, Abstract.
Cuesov, Drug Production Technology, Khar'kov, 1999, pp. 351-352.
Tennant, "Simultaneous Use of Stimulants and Opioids," 2011 [online] retrieved on Jul. 7, 2016 from: http://www.practicalpainmanagement.com/treatments/pharmacological/opiods/simultaneous-use-stimulants-opioids; 7 pages.
Cuesov, Drug Production Technology, Khar'kov, 1999, pp. 351-352. (Full translation attached.).
Extended European Search Report for Application No. EP 16182124.4-1455, dated Jan. 17, 2017.
Bannwarth, Bernard, "Will Abuse-Deterrent Formulations of Opioid Analgesics be Successful in Achieving Their Purpose?", Drugs, 2012, vol. 72, pp. 1713-1723.
Compap 90 technical data sheet Mar. 2014; 1 page.
Furu et al. "use of ADHD drugs in the Nordic countries: a population-based comparison study," Acta Psychiatrica Scandinavia, May 2010.
Nickerson, B., Sample Preparation of Pharmaceutical Dosage Forms, Springer, New York (2011); Chapter 1, pp. 3-48.
PCT International Search Report and Written Opinion for PCT Application No. PCT/EP2016/052046 dated Apr. 12, 2016.

(56) References Cited

OTHER PUBLICATIONS

PCT International Search Report and Written Opinion for PCT Application No. PCT/EP2017/070396 dated Sep. 8, 2017.
Polyox Water-Soluble Resins in Pharmaceutical Applications. Dow Chemicals, Published 2004.
Qi et al, "An Investigation into the Crystallisation Behavior of an Amorphous Cryomilled Pharmaceutical Material Above and Below the Glass Transition Temperature," Journal of Pharmaceutical Sciences, 2009, 196-208.
Houston, T.E., et al., "Bite Force and Bite Pressure: Comparison of Humans and Dogs," http://www.glapbta.com/BFBP.pdf, 2003, pp. 1-7.
Sigma-Aldrich entry for CAS No. 9010-88-2; www.sigmaaldrich.com/catalog/product/aldrich/182249?lang=en&region=US (downloaded Jun. 2018).
Patrick, K., et al., "Pharmacology of Methylphenidate, Amphetamine Enantiomers and Pemoline in Attention-Deficit Hyperactivity Disorder," Human Psychopharmacology, vol. 12, 527-546 (199).
"Low Substituted Hydroxypropyl Celluslose", Drugs.com, from https://www.drugs.com/inactive/low-susbstitute-hydroxypropyl-cellulose-581.html (2018).
Agarwal, G, et al, "Oral Sustained Release Tablets: An Overview with a Special Emphasis on Matrix Tablet," American Journal of Advanced Drug Delivery, 2017.
Brzeclo, W.,et al., "The Advent of a new Pseudoephedrine Product to Combat Methampetamine Abuse," Am J Drug Alcohol Abuse, 2013: 39(5): 284-290.
Extended European Search Report for Application No. 17173240.7 dated Nov. 28, 2017.
Jamini, M., et al, "Sustained Release Matrix Type Drug Delivery System: A Review," Journal of Drug Delivery & Therapeutics; 2012, 2(6), 142-148.
Kelly, C. et al, "Methamphetamine Synthesis Inhibition: Dissolving Metal Reductions," Johns Hopkins Univ. Applied Physics Lab., 2015, 1-10.
Misal, R, et al., "Matrix Tablet: A Promising Technique for Controlled Drug Delivery," Indo American Journal of Pharmaceutical Research, 2013.
Presley, B. et al., "Efficiency of Extraction and Conversion of Pseudoephedrine to Methamphetamine from Tamper-Resistant and Non-Tamper-Resistant Formulations," Journal of Pharmaceutical and Biomedical Analysis , 2018, 16-22.
Targin(R) Product Monograph. Purdue Pharma. Revised Mar. 1, 2016.
Definition Granule, Merriam-Webster, accessed online Jun. 28, 2018 (2018).
De Brabander C., et al., "Development and evaluation of sustained release mini-matrices prepared via hot melt extrusion," Journal of Controlled Release 89 (2003), 235-247.
European Pharmacopeia, 7th Ed. 2.2.8 and 2.2.10, 27ff. (2010).
Evekeo, (Amphetame Sulfate) for treating patients with ADHD website ([online] https://evekeo.com.about-evekeo; 2019:5 pages), 2019.
Jedinger, N., et al., Eur. J. Pharm. Biopharm 87 (2014), 217-226.
Lurie et al., "Chiral Resolution of Cationic Drugs of Forensic Interest," (Analytical Chemistry 1994; 66(22): 4019-4026.
Romach et al. "Update on tamper-resistant drug formulation," Drug and Alcohol Dependence, 130 (2013), 13-23.
Polyox, 2004, online retrieved on Oct. 15, 2018.
Pintauro, Nicholas, D., Food Flavoring Processes, Table of Content. Park Ridge, NJ and London, UK, 1976.
Ely et al., "Lithium-Ammonia Reduction of Ephedrine to Methamphetamine: An Unusual Clandestine Synthesis," Technical Note, 1990, 720-723.
Kunalan et al., "Investigation of the Reaction Impurities Associated with Methylamphetamine Synthesized using the Nagai Method," Anal. Chem. 2012, 84, 5744-52.

Lee et al., "Analysis of the impurities in the metamphetamine synthesized by thee different methods from ephedrine and pseudoephedrine," Forensic Science International 161 (2006), 209-215.
Person et al., Structural Determination of the Principal Byproduct of the Lithium-Ammonia Reduction Method of Methamphyetamine Manufacture, J Forensic Sci, Jan. 2005, vol. 50, No. 1, 87-95.
Salouros et al., Isolation and Identification of Three By-Products Found in Methylamphetamine Synthesized by the Emde Route2010, 605-615.
Skinner, Harry F., "Methamphetamine Synthesis via Hydriodic Acid/Red Phosphorus Reduction of Ephedrine," Forensic Science International, 48 (1990), 123-134.
Weinhold, et al. "Buprenophine alone and in combination with naloxone in non-dependent humans." Drug & Alcohol Dependence 30.3 (1992): 263-274.
Gaitondf, B. "General Principles of Drug Action", 1967, p. 48.
BASF the chemical company, Kollicoat IR Technical information, Feb. 2013, p. 1-14 (2013).
Befort et al., "The Conserved Asparatate Residue in the Third Putative Transmember Domain," Molecular Pharmacology 1996: 49:216-223 (1996).
Domino E.F. (1991) Nicotine: A Unique Psychoactive Drug. In: Adlkofer F., Thurau K. (eds.) Effects of Nicotine on Biological Systems. APS Advances in Pharmacological Sciences. Birkhaeuser Basel (1991).
Fitzpatrick, J., "The influence of Superdisintegrants on Immediate Release," by Pharmaceutical Technology Editions [online] retrieved from http://www.pharmatech.com/influence-superdisintegrants-immediate-release, vol. 21, issue 6 (Jun. 1, 2011).
Kolar et al., "Treatmen of adults with attention-deficit/hyperactivity disorder," Neuropsychiatric Disease and Treatment 2008:4(3):389-403.
Rasmussen, N. "America's First Amphetamine Epidemic 1929-1971," American Journal of Public Health 2008:98(6): 974-985.
Suzuki, T, "Blood-brain barrier transport of opioid analgesics," Abstract, Yakugaki Zasshi: 131(10):1445-51 (2011).
Claffey et al, "Amphetamine Adducts of Melanin Intermediates Demonstrated by Matrix-Assisted Laser Desorption Ionization Time-of-Flight Mass Spectrometry," Chem. Res. Toxicol. 2001, 14, 1339-1344.
Evans, J.C, et. al. "Optimal tocopherol concentrations to inhibit soybean oil oxidation," Journal of The American Oil Chemists' Society 79.1 (2002): 47-51.
Quinn, M.E. "Alpha Tocopherol" in Handbook of Pharmaceuical Excipients, Sixth Edition (2009), 31-33.
Thumma et al., "Influence of Plasticizers on the Stability of a Prodrug of D9-Tetrahydrocannabinol Incorporated in poly(Ethyelen Oxide) Matrices", Eur J. Pharm Biopharm. Oct. 2008 (70(2). 605-614.
Heal et al. "Amphetamine, past and present—a pharmacological and clinical perspective," Journal of Psychology 2013:27(6):479-496 (2013).
Martin et al., "Applications of Polyethylene Oxide (POLYOX) in Hydrophilic Matrices," in Hydrophilic Matrix Tablets for Oral Controlled Release, Springer, New York, 2014, Chapter 5, pp. 123-141.
Vosburg, et al., "A comparison among tapentadol tamper-resistant formulations (TRF) and OxyCotin® (non-TRF) in prescription opioid abusers," 2013; Society for the Study of Addiction; Addiction, vol. 108, pp. 1095-1106.
Pharma Tips ([online] retrieved on Mar. 22, 2018 from http://ww.pharmatips.in/Articles/Pharmaceutics/Tablet/Co-Processed-Directly-Compressed-Adjutants.aspx; May 2011: 10 pages).
Alekseeva et al, Chemical-Pharmaceutical Journal, vol. 41, No. 9, 2007, 49-52. (English abstract included.).
Extended European Search Report and Opinion for Application No. EP 15184634.2-1455, dated Mar. 3, 2016.
Saleem et al. "Formulation and Evaluation of Tramadol hydrochloride Rectal Suppositories," Indian J. Pharm Sci. Sep.-Oct. 2008; 70(5), 640-644.
The Merck Index, 14th Ed. (2006) No. 0006360 Nalefene.
The Merck Index, 14th Ed. (2006) No. 0006362 Naloxone.

(56) References Cited

OTHER PUBLICATIONS

The Merck Index, 14th Ed. (2006) No. 0006363 Naltrexone.
The Merck Index, 14th Ed. (2006) No. 0006959 Oxycodone.
Lefnaoui et al., Synthesis and evaluation of the structural and physiochemical properties of carboxymethyl pregelatinized starch as a pharmaceutical excipient, Saudi Pharmaceutical Jourani, Feb. 2015:23:698-711 (2015).
Lopez-Solis et al, Effect of disintegrants with different hygroscopicity on dissolution of Norfloxacin/Pharmatose DCL 11 tablets, International Journal of Pharmaceutics 2001:216:127-135 (2001).
U.S. Appl. No. 60/287,509, dated Dec. 2, 2002, Joshi et al.
U.S. Appl. No. 60/288,211, dated Sep. 2, 2004, Oshlack et al.
U.S. Appl. No. 60/310,514, Apr. 3, 2003, Oshlack et al.
U.S. Appl. No. 60/310,534, dated Apr. 10, 2003, Wright et al.
U.S. Appl. No. 60/376,470, dated Jan. 15, 2004, Ayer et al.
U.S. Appl. No. 60/384,442, Dec. 4, 2003, Fink et al.
European Pharmacopoeia 3.0, 2.9.8 "Resistance to Crushing of Tablets", 1997, p. 135.
Goodman and Gilman, 1985, 7th edition, chapter 29, 674-715,.
King, Remington's Pharmaceutical Sciences 17th ed., Chapter 78, p. 1418-1419 (1985).
Patel Et. Al., "Poloxamers: A pharmaceutical excipient with therapeutic behaviors," PharmTech, vol. 1, No. 2, pp. 299-300 (Apr. 2009).
Quadros, E. et al., "Evaluation of a novel colonic delivery device in vivo," STP Pharma Sci. 5, 77-82 (1995).
Sprockel, et. al, "A melt-extrusion process for manufacturing matrix drug delivery systems," Int. Journal of Pharmaceutics 155 (1997) 191-199.
Sumitomo Seika Chemicals, Co., Ltd, "Certificate of Analysis," Product: Polyethylene Oxide; Grade: PEO-18NF; Feb. 2, 2016.
Sumitomo Seika Chemicals, Co., Ltd, "Certificate of Analysis," Product: Polyethylene Oxide; Grade: PEO-20NF; Feb. 3, 2016.
Sumitomo Seika Chemicals, Co., Ltd, "Certificate of Analysis," Product: Polyethylene Oxide; Grade: PEO-20NF; Jan. 23, 2012.
Sumitomo Seika Chemicals, Co., Ltd, "Certificate of Analysis," Product: Polyethylene Oxide; Grade: PEO-20NF; May 15, 2013.
Theeuwes, Felix et al., Osmotic Systems for Colon-Targeted Drug Delivery in Colonic Drug Absorption and Metabolism (Peter R. Bieck ed., 1993).
Turkington, R., "Amphetamines,"in Chemicals used for Illegal Purposes. A Guide for first Reponsders to Identify Explosives, Recreational Drugs, and Poisons, 2010, p. 247.
Vezin, W. et al, "Adjustment of precompression force to reduce mixing-time dependence of tablet tensile strength," J. Pharm. Pharmacol. 1983, 35: 555-558 (Mar. 28, 1983).
Wooten, Marvin R. et al., Intracerebral Hemorrhage and Vasculitis Related to Ephedrine Abuse; 13 Annals of Neurology 337 (1983).

\* cited by examiner

CRUSH RESISTANT DELAYED-RELEASE DOSAGE FORMS

CROSS-REFERENCE TO RELATED APPLICATIONS

This application is a continuation of U.S. application Ser. No. 14/749,939, filed Jun. 25, 2015 now pending, which is a continuation of U.S. application Ser. No. 14/141,793, filed Dec. 27, 2013, now abandoned, which is a continuation of U.S. application Ser. No. 12/640,915, filed Dec. 17, 2009, abandoned, which is a divisional of U.S. application Ser. No. 11/348,295, filed Feb. 6, 2006, abandoned, which claims foreign priority from German Patent Application No. 10 2005 005 446.3, filed on Feb. 4, 2005.

BACKGROUND OF THE INVENTION

The present invention relates to a dosage form for administering a physiologically active substance (A), wherein the dosage form is mechanically stabilised, such that it cannot be comminuted by conventional methods, such as pounding, crushing, grinding in a mortar etc., or at least comminuted only with very great difficulty. The substance (A) is released from the dosage form according to the invention under physiological conditions with an at least partially delayed release profile.

Numerous physiologically active substances, such as nutritional supplements, pharmaceutical substances etc., are provided as delayed-release formulations, i.e., in contrast to conventional formulations (for example "immediate release" formulations), release of the substances from these formulations into the body is delayed for a comparatively long period, which often amounts to several hours. Release of the substance from the dosage form, on the one hand, and metabolisation or excretion by the organism; on the other hand, ensure a relatively uniform blood plasma level for the administered substance. As a consequence thereof, the number of dosage units which need to be taken per day by patients can frequently be reduced, intake often being required only once or twice a day.

In certain cases, delayed-release formulations may also reduce the extent of side-effects caused by the substance. Thus, for example, some pharmaceutical substances produce intensified side-effects if a given limit concentration of the pharmaceutical substance in the blood plasma is exceeded at least transiently. Such pharmaceutical substances are therefore generally unsuitable for "immediate release" formulations, in particular if it is desired to administer said formulations only two or three times daily. Such pharmaceutical substances are therefore conventionally administered as delayed-release formulations, whereby continuous release of the active ingredient is ensured and short-term occurrence of elevated concentrations is prevented.

In delayed-release formulations, the physiologically active substance is conventionally either embedded in a matrix controlling release and/or the dosage form is coated with a film which controls release.

However, older patients in particular frequently have difficulties in taking solid dosage forms, such as tablets, gelatine capsules, etc. They choke on them and sometimes develop pronounced aversion to such dosage forms.

To counter this problem, various apparatuses have been developed by means of which solid dosage forms may be comminuted or pulverised ("tablet crushers"). Such apparatuses are used, for example, by the care staff in old people's homes. The dosage forms are then administered to the people being cared for not as tablets etc. but rather as powder, for example to get round the difficulties involved in swallowing tablets.

However, the comminution of dosage forms with such apparatuses is problematic if the dosage forms are delayed-release formulations. As a rule, comminution then results in destruction of the inner structure of the dosage form, which is responsible for the delayed release, so doing away with the delayed-release action. As a result of comminution, the diffusion paths of the physiologically active substances contained therein are shortened and/or the diffusion barriers are removed. For instance, a delayed-release formulation in which delayed release is achieved by means of a film coating exhibits the film coating over only a small percentage of its solid surface after comminution. Consequently, after administration, frequently all the physiologically active substance originally contained in the dosage form is released in a relatively short time, whereby a comparatively very high plasma concentration of the substance is abruptly reached for a relatively short period. In this way, the original delayed-release formulations become "immediate release" formulations.

Depending on the physiological activity of the substance, this may cause considerable side-effects however, and in extreme cases may even lead to the death of the patient. Examples of substances with such a hazard potential are antiparkinson drugs, antiepileptics, antidiabetics, antihypertensives, antiarrhythmics, etc.

As a rule, the people who comminute the dosage forms for themselves or for others are not aware of these risks. Cases are known in which patients have died probably as a result of pulverisation of delayed-release formulations by nurses or carers. For further details, reference may be made for example to J. E. Mitchell, Oral Dosage Forms That Should Not Be Crushed: 2000 Update, Hospital Pharmacy, 2000; H. Miller et al., To Crush or Not to Crush, Nursing 2000; R. Griffith et al., Tablet Crushing and the law: the implications for nursing; Prof. Nurse 2003; J. G. Schier et al, Fatality from administration of labetalol and crushed extended-release nifedipine, Ann. Pharmacotherapy 2003; A. James, The legal and clinical implications of crushing tablet medication, Nurse Times 2005, 100(50), 28-9; and P. Cornish, "Avoid the Crush": hazards of medication administration in patients with dysphagia or a feeding tube, CMAJ. 2005, 172(7), 871-2.

Delayed-release formulations may also cause problems for small children. For instance, children frequently cannot distinguish solid dosage forms from sweets. If children find such dosage forms, for example because their parents have carelessly left them lying around in the home, there is a risk that the children may think that the dosage forms are sweets and put them in their mouths and chew them. If said dosage forms are delayed-release formulations, which contain a pharmaceutical substance in a dosage intended for adults, the child may in such a case already be at risk of overdose due to the relatively large amount of pharmaceutical substance contained therein. By chewing the dosage form and thus cancelling out the delayed-release action, this risk is increased still further, however, since the excessively high dose already contained therein is additionally released over a greatly reduced period of time, a situation which would be very hazardous even for an adult and which may have all the more drastic consequences for a child.

The chewing of delayed-release formulations may also lead to an overdose of the substance contained therein in adults. Sometimes adults chew the dosage forms deliberately, though often in ignorance of the type and purpose of a delayed-release formulation, because they hope for a quicker effect.

A known way of reducing the risks involved in comminuting delayed-release formulations consists in adding to the dosage form antagonists, i.e. antidotes, or compounds which produce defensive reactions, wherein the physiological action of these additives are as far as possible manifested only if the dosage form has been comminuted prior to administration. This method has the disadvantage, however, that the physiologically active substance is nonetheless administered in non-delayed form and that the organism is additionally exposed to a further physiologically active substance, for example an antidote, or to a defensive reaction, such as for example vomiting.

There is a need for pharmaceutical dosage forms with delayed release which reduce the risk of overdose, such that e.g. antidotes etc. may be dispensed with.

Thus, it is an object of the invention to provide a dosage form having advantages over the dosage forms of the prior art. The dosage form should release a physiologically active substance on a delayed-release basis but should reduce the risk of overdose, in particular as a consequence of improper handling of the dosage form, such as chewing, crushing, grinding in a mortar etc.

SUMMARY OF THE INVENTION

It has surprisingly been found that this object is achieved by a dosage form comprising
- a physiologically effective amount of a physiologically active substance (A) (=component (A));
- optionally one or more physiologically acceptable auxiliary substances (B) (=component (B));
- a synthetic, semi-synthetic or natural polymer (C) (=component (C)); and
- optionally a physiologically acceptable synthetic, semi-synthetic or natural wax (=component (D));
- wherein the dosage form exhibits a resistance to crushing of at least 400 N, and in increasingly preferred embodiments of at least 420 N, at least 440 N, at least 460 N, at least 480 N or of at least 500 N, and wherein under physiological conditions the release of the physiologically active substance (A) from the dosage form is at least partially delayed.

The dosage form according to the invention exhibits mechanical strength over a wide temperature range, in addition to the resistance to crushing optionally also sufficient hardness and impact strength for it to be virtually impossible to comminute or pulverise by chewing, grinding in a mortar, pounding, etc., even by means of commercially available apparatuses for pulverising conventional dosage forms. This is not necessarily achieved by the hardness of the dosage form. For instance, the impact strength of the dosage form according to the invention and its resistance to crushing, respectively, may in particular also mean that it may be deformed as a result of external mechanical action, for example using a hammer, but does not crumble into a number of fragments. Comminution is not even successful when the dosage form is initially chilled to increase its brittleness, for example to temperatures below −25° C., below −40° C. or indeed in liquid nitrogen.

As a consequence of the resistance to crushing, delayed release is maintained and an overdose due to improper handling of the dosage form is effectively prevented.

The advantageous properties of the dosage form according to the invention, in particular also its mechanical properties, may not automatically be achieved by simply processing components (A), (C), optionally (B) and optionally (D) by means of conventional methods for the preparation of dosage forms. In fact, usually suitable apparatuses must be selected for the preparation and critical processing parameters must be adjusted, particularly pressure/force, temperature and time. Only if in the course of the preparation of the dosage form the components are exposed to a sufficient pressure at a sufficient temperature for a sufficient period of time, dosage forms exhibiting the desired properties may be obtained. Thus, even if conventional apparatuses are used, the process protocols usually must be adapted in order to meet the required criteria.

Delayed release is understood according to the invention preferably to mean a release profile in which the physiologically active substance is released over a relatively long period with reduced intake frequency with the purpose of extended therapeutic action. This is achieved in particular with peroral administration. The expression "with at least partially delayed release" covers according to the invention any dosage forms which ensure modified release of the physiologically active substances contained therein. The dosage forms preferably comprise coated or uncoated dosage forms, which are produced with specific auxiliary substances, by particular processes or by a combination of the two possible options in order purposefully to change the release rate or location of release.

In the case of the dosage forms according to the invention, the release time profile may be modified e.g. as follows: extended release, repeat action release, prolonged release and sustained release.

DETAILED DESCRIPTION OF THE INVENTION

Figure 1:
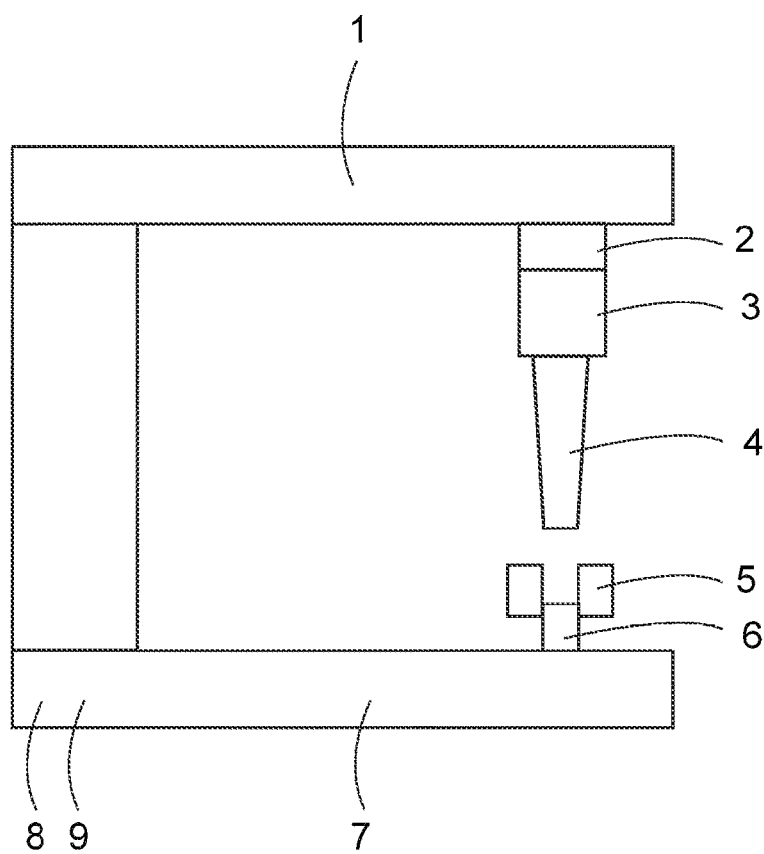
FIG. 1 depicts an ultrasound device used to supply energy for production of the dosage form.

For the purpose of the specification "extended release" means a product in which the release of active substance is delayed for a finite lag time, after which release is unhindered.

For the purpose of the specification "repeat action release" means a product in which a first portion of active substance is released initially, followed by at least one further portion of active substance being released subsequently.

For the purpose of the specification "prolonged release" means a product in which the rate of release of active substance from the formulation after administration has been reduced, in order to maintain therapeutic activity, to reduce toxic effects, or for some other therapeutic purpose.

For the purpose of the specification "sustained release" means a way of formulating a medicine so that it is released into the body steadily, over a long period of time, thus reducing the dosing frequency. For further details, reference may be made, for example, to K. H. Bauer, Lehrbuch der Pharmazeutischen Technologie, 6th edition, WVG Stuttgart, 1999; and European Pharmacopoeia.

In increasingly preferred embodiments, after 5 hours under physiological conditions, the dosage form has released not more than 99%, or not more than 90%, or not more than 75%, or not more than 50%, or not more than 40% or not more than 30% of substance (A). It is particularly preferable for the dosage form in this case to contain neither tramadol hydrochloride, nor oxycodone hydrochloride, or more desirably, no opioid [N02A] (for the meaning of "N02A" see below). Release is determined using the standardised method in the European Pharmacopoeia, preferably under the conditions stated in Example 1.

In a preferred embodiment, under physiological conditions the dosage form according to the invention has released after 30 minutes 0.1 to 75%, after 240 minutes 0.5 to 95%, after 480 minutes 1.0 to 100% and after 720 minutes 2.5 to 100% of substance (A).

Further embodiments exhibit release profiles 1 to 5 and are summarised in the table here below [all data in wt.-% of released component (A)]:

| time [h] | No. 1 | No. 2 | No. 3 | No. 4 | No. 5 |
|---|---|---|---|---|---|
| 1 | 0-30 | 0-50 | 0-50 | 15-25 | 20-50 |
| 2 | 0-40 | 0-75 | 0-75 | 25-35 | 40-75 |
| 4 | 3-55 | 3-95 | 10-95 | 30-45 | 60-95 |
| 8 | 10-65 | 10-100 | 35-100 | 40-60 | 80-100 |
| 12 | 20-75 | 20-100 | 55-100 | 55-70 | 90-100 |
| 16 | 30-88 | 30-100 | 70-100 | 60-75 | |
| 24 | 50-100 | 50-100 | >90 | | |
| 36 | >80 | >80 | | | |

The release properties of the dosage form according to the invention are substantially independent from the pH value of the release medium, i.e. preferably the release profile in artificial intestinal juice substantially corresponds to the release profile in artificial gastric juice. At any given time point the release profiles deviate from one another by not more than 20%, in increasingly preferred embodiments, the deviation is not more than 15%, or not more than 10%, or not more than 7.5%, or not more than 5.0% or not more than 2.5%.

Preferably, the dosage form according to the invention exhibits an uniform release profile. Preferably, the release profile of the physiologically active substance (A) is inter-individually uniform (i.e. when comparing dosage forms obtained from the same process) and/or uniform within a single dosage form (i.e. when comparing segments of the same dosage form). Desirably, when comparing two probes each having a mass of preferably 500 mg, the total amount of the released active substance for any given time point of the measurement does not deviate by more than 20%, or not more than 15%, or not more than 10%, or not more than 7.5%, or not more than 5.0% or not more than 2.5%.

The release profile of the dosage form according to the present invention is stable upon storage, such as upon storage at elevated temperature, e.g. 37° C., for 3 months in sealed containers. In this regard "stable" means that when comparing the initial release profile with the release profile after storage, at any given time point the release profiles deviate from one another by not more than 20%, or not more than 15%, or not more than 10%, or not more than 7.5%, or not more than 5.0% or not more than 2.5%, with the later being most preferred.

By using certain polymers in suitable quantities and under suitable conditions, a resistance to crushing is achieved according to the invention for the dosage form of at least 400 N, or of at least 420 N, or of at least 440 N, or of at least 460 N, or of at least 480 N or of at least 500 N (measured as stated in the description; the preferred method for measuring the resistance to crushing according to the invention is a modification of the method disclosed in the European Pharmacopoeia 5.0, page 235, 2.9.8 "Resistance to Crushing of Tablets"). It is thereby possible effectively to prevent comminution, for example pulverisation, of the dosage form using conventional means.

For the purpose of the specification, "comminution" means pulverisation of the dosage form by the application of force with conventional means, such as for example a pestle and mortar, a hammer, a mallet or other usual means for pulverisation, in particular devices developed for this purpose (tablet crushers), wherein the proportion of fines which may arise (particle size equal to or smaller than 0.3 mm) must not exceed 5 wt. %.

The dosage form according to the invention is therefore suitable for preventing overdosing on physiologically active substances, in particular nutritional supplements and pharmaceutical substances, which are provided in delayed-release formulations. It is then possible to dispense with antidotes, irritants etc. In addition to preventing overdoses and the accompanying risks for patients, the dosage forms according to the invention additionally ensure that the other advantages of delayed-release formulation, such as for example uniform release over a relatively long period, are retained and cannot easily be overcome.

To achieve the necessary resistance to crushing of the dosage form according to the invention, at least one synthetic, semi-synthetic or natural polymer (C) is used, which contributes considerably to the elevated resistance to crushing of the dosage form. The resistance to crushing of the dosage form amounts to at least 400 N, to at least 420 N, to at least 440 N, to at least 460 N or to at least 480 N, wherein the resistance to crushing is determined using the method stated in the description. In a preferred embodiment, the resistance to crushing of the dosage form amounts to at least 500 N, to at least 600 N, to at least 700 N, to at least 800 N, to at least 900 N, to at least 1000 N or even to at least 1100 N.

Besides its resistance to crushing, the dosage form according to the invention is preferably featured by further mechanical properties, e.g. its hardness, impact resistance, impact elasticity and/or modulus of elasticity, optionally also at low temperatures (e.g. below −24° C., below −40° C. or in liquid nitrogen).

In increasingly preferred embodiments, the dosage form according to the invention has a density of at least 0.80 or at least 0.85 g/cm$^3$, at least 0.90 or at least 0.95 g/cm$^3$, at least 1.00, at least 1.05 or at least 1.10 g/cm$^3$, in the range from 0.80 to 1.35 g/cm$^3$, and in particular in the range from 0.95 to 1.25 g/cm$^3$.

The dosage form according to the invention is characterized by a comparatively homogeneous distribution of density. Preferably, the densities of two segments of the dosage form having a volume of 1.0 mm$^3$ each, deviate from one another by not more than ±10%, or by not more than ±7.5%, or by not more than ±5.0%, or by not more than ±2.5%, and in particular by not more than ±1.0%.

The dosage form according to the invention is characterized by a comparatively homogeneous distribution of the physiologically active substance (A). Preferably, the content of component (A) in two segments of the dosage form having a volume of 1.0 mm$^3$ each, deviates from one another by not more than ±10%, more preferably not more than ±7.5%, still more preferably not more than ±5.0%, most preferably not more than ±2.5%, and in particular not more than ±1.0%.

Preferably, the total weight of the dosage form according to the invention is within the range from 0.01 g to 1.5 g, more preferably 0.05 g to 1.2 g, still more preferably 0.1 g to 1.0 g, most preferably 0.2 g to 0.9 g and in particular 0.25 g to 0.8 g.

The dosage form according to the invention preferably contains at least one synthetic, semi-synthetic or natural polymer (C). For the purpose of the specification a "semi-synthetic" product has been produced by chemical manipulation of naturally occurring substances.

Particularly preferred are high molecular weight polymers with a preferably weight average molecular weight ($M_w$) or viscosity average molecular weight ($M_\eta$) of at least $0.5 \cdot 10^6$ g/mol, of at least $1.0 \cdot 10^6$ g/mol, of at least $2.5 \cdot 10^6$ g/mol, of at least $5.0 \cdot 10^6$ g/mol, of at least $7.5 \cdot 10^6$ g/mol or of at least $10 \cdot 10^6$ g/mol, preferably $1.0 \cdot 10^6$ g/mol to $15 \cdot 10^6$ g/mol. Suitable methods for determining $M_w$ or $M_\eta$ are known to the person skilled in the art. Preferably, $M_\eta$ is determined using rheological measurements and $M_w$ is determined using gel permeation chromatography (GPC) on suitable phases.

The polymers (C) preferably have a viscosity at 25° C. of 4,500 to 17,600 cP, measured in a 5 wt. % aqueous solution using a model RVF Brookfield viscosimeter (spindle no. 2/rotational speed 2 rpm), of 400 to 4,000 cP, measured on a 2 wt. % aqueous solution using the stated viscosimeter (spindle no. 1 or 3/rotational speed 10 rpm) or of 1,650 to 10,000 cP, measured on a 1 wt. % aqueous solution using the stated viscosimeter (spindle no. 2/rotational speed 2 rpm).

Individual or combinations of polymers may be selected from the group comprising polyalkylene oxide, preferably polymethylene oxide, polyethylene oxide, polypropylene oxide; polyethylene, polypropylene, polyvinyl chloride, polycarbonate, polystyrene, polyacrylate, poly(hydroxy fatty acids), such as for example poly(3-hydroxybutyrate-co-3-hydroxyvalerate) (Biopol®), poly(hydroxyvaleric acid); polycaprolactone, polyvinyl alcohol, polyesteramide, polyethylene succinate, polylactone, polyglycolide, polyurethane, polyvinylpyrrolidone, polyamide, polylactide, polyacetal (for example polysaccharides optionally with modified side chains), polylactide/glycolide, polylactone, polyglycolide, polyorthoester, polyanhydride, block polymers of polyethylene glycol and polybutylene terephthalate (Polyactive®), polyanhydride (Polifeprosan), copolymers thereof, block-copolymers thereof, and mixtures of at least two of the stated polymers, or other polymers with the above characteristics.

Thermoplastic polyalkylene oxides having a weight average molecular weight ($M_w$) or a viscosity average molecular weight ($M_\eta$) of at least $0.5 \cdot 10^6$ g/mol are particularly preferred, e.g. polyethylene oxides, polypropylene oxides or the (block-)copolymers thereof.

In a preferred embodiment according to the invention component (C) comprises
 a polyalkylene oxide having a weight average molecular weight ($M_w$) or viscosity average molecular weight ($M_\eta$) of at least $0.5 \cdot 10^6$ g/mol
 in combination with
 at least one further polymer, preferably also having a weight average molecular weight ($M_w$) or viscosity average molecular weight ($M_\eta$) of at least $0.5 \cdot 10^6$ g/mol, selected from the group consisting of polyethylene, polypropylene, polyvinyl chloride, polycarbonate, polystyrene, polyacrylate, poly(hydroxy fatty acids), polycaprolactone, polyvinyl alcohol, polyesteramide, polyethylene succinate, polylactone, polyglycolide, polyurethane, polyvinylpyrrolidone, polyamide, polylactide, polyacetal, polylactide/glycolide, polylactone, polyglycolide, polyorthoester, polyanhydride, block polymers of polyethylene glycol and polybutylene terephthalate, polyanhydride and copolymers thereof.

Preferably, the content of said further polymer amounts to 1.0 to 25 wt.-%, more preferably 5.0 to 10 wt.-%, based on the total weight of polymer (C).

The polymer (C) is preferably used in the form of powder. It may be water-soluble.

In one embodiment, the polymer (C) is used in a quantity of at least 20 wt. %, preferably at least 30 wt. %, more preferably at least 40 wt. %, most preferably at least 50 wt. % and in particular at least 60 wt. %, relative to the total weight of the dosage form. In a preferred embodiment it is used in a quantity of from about 20 to about 49 wt.-%, relative to the total weight of the dosage form.

The dosage form according to the invention is suitable for the administration of a number of physiologically active substances (A) in a single dosage form. Preferably, the dosage form contains only one particular physiologically active substance (A), preferably a nutritional supplement or a pharmaceutical substance (=pharmaceutical active ingredient).

The amount of the physiologically active substance (A), based on the total amount of the dosage form, is preferably within the range from 0.01 to 95 wt.-%, more preferably from 0.5 to 80 wt.-%, still more preferably 1.0 to 70 wt.-%, most preferably 5.0 to 60 wt.-% and in particular 10 to 50 wt.-%. In a preferred embodiment it is more than 20 wt.-%.

In a preferred embodiment the dosage form according to the invention does not contain a psychotropically acting substance as the physiologically active substance (A). The person skilled in the art knows which substances have a psychotropic action. Substances which influence psychological processes commonly have a psychotropic action, i.e. they act specifically on psychological functions. Substances with a psychotropic action may thus influence mood, either raising or lowering it. For the purpose of the description, substances with a psychotropic action include in particular opioids, stimulants, tranquillisers (e.g. barbiturates and benzodiazepines) and other narcotics. Substances with a psychotropic action preferably comprise substances which, in particular when improperly administered (in particular with the intention of abuse), cause an accelerated increase in active ingredient levels relative to proper oral administration, giving the abuser the desired effect, namely the "kick" or "rush". This kick is also obtained if the powdered dosage form is administered nasally, i.e. is sniffed. Substances with a psychotropic action are preferably substances which (in the appropriate dose and dosage form and when administered appropriately) influence human mental activity and/or sensory perception in such a way that they are fundamentally suited to abuse.

The following opiates, opioids, tranquillisers or other narcotics are substances with a psychotropic action, i.e. have a potential of abuse, and hence are preferably not contained in the dosage form according to the invention: alfentanil, allobarbital, allylprodine, alphaprodine, alprazolam, amfepramone, amphetamine, amphetaminil, amobarbital, anileridine, apocodeine, barbital, bemidone, benzylmorphine, bezitramide, bromazepam, brotizolam, buprenorphine, butobarbital, butorphanol, camazepam, carfentanil, cathine/D-norpseudoephedrine, chlordiazepoxide, clobazam clofedanol, clonazepam, clonitazene, clorazepate, clotiazepam, cloxazolam, cocaine, codeine, cyclobarbital, cyclorphan, cyprenorphine, delorazepam, desomorphine, dextromoramide, dextropropoxyphene, dezocine, diampromide, diamorphine, diazepam, dihydrocodeine, dihydromorphine, dihydromorphone, dimenoxadol, dimephetamol, dimethylthiambutene, dioxaphetylbutyrate, dipipanone, dronabinol, eptazocine, estazolam, ethoheptazine, ethylmethylthiambutene, ethyl loflazepate, ethylmorphine, etonitazene, etorphine, fencamfamine, fenethylline, fenpipramide, fenproporex, fentanyl, fludiazepam, flunitrazepam, flurazepam, halazepam, haloxazolam, heroin, hydrocodone, hydromorphone, hydroxypethidine, isomethadone, hydroxymethylmorphinan, ketazolam, ketobemidone, levacetylmethadol (LAAM), levomethadone, levorphanol, levophenacylmorphane, levoxemacin, lofentanil, loprazolam, lorazepam, lormetazepam, mazindol, medazepam, mefenorex, meperidine, meprobamate, metapon, meptazinol, metazocine, methylmorphine, metamphetamine, methadone, methaqualone, 3-methylfentanyl, 4-methylfentanyl, methylphenidate, methylphenobarbital, methyprylon, metopon, midazolam, modafinil, morphine, myrophine, nabilone, nalbuphene, nalorphine, narceine, nicomorphine, nimetazepam, nitrazepam, nordazepam, norlevorphanol, normethadone, normorphine, norpipanone, opium, oxazepam, oxazolam, oxycodone, oxymorphone, Papaver somniferum, papaveretum, pernoline, pentazocine, pentobarbital, pethidine, phenadoxone, phenomorphane, phenazocine, phenoperidine, piminodine, pholcodeine, phenmetrazine, phenobarbital, phentermine, pinazepam, pipradrol, piritramide, prazepam, profadol, proheptazine, promedol, properidine, propoxyphene, remifentanil, secbutabarbital, secobarbital, sufentanil, temazepam, tetrazepam, tilidine (cis and trans), tramadol, triazolam, vinylbital, N-(1-methyl-2-piperidinoethyl)-N-(2-pyridyl)propionamide, (1R,2R)-3-(3-dimethylamino-1-ethyl-2-methyl-propyl)phenol, (1R,2R,4S)-2-(dimethylamino)methyl-4-(p-fluorobenzyloxy)-1-(m-methoxyphenyl)cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3 (3-methoxyphenyl)-2-methyl-pentan-3-ol, (1RS,3RS,6RS)-6-dimethylaminomethyl-1-(3-methoxyphenyl)-cyclohexane-1,3-diol, preferably as racemate, 3-(2-dimethylaminomethyl-1-hydroxy-cyclohexyl)phenyl 2-(4-isobutyl-phenyl)propionate, 3-(2-dimethylaminomethyl-1-hydroxy-cyclohexyl)phenyl-2-(6-methoxy-naphthalen-2-yl)propionate, 3-(2-dimethylaminomethyl-cyclohex-1-enyl)-phenyl 2-(4-isobutyl-phenyl)propionate, 3-(2-dimethylaminomethyl-cyclohex-1-enyl)-phenyl 2-(6-methoxy-naphthalen-2-yl)propionate, (RR-SS)-2-acetoxy-4-trifluoromethyl-benzoic acid 3-(2-dimethylaminomethyl-1-hydroxy-cyclohexyl)-phenyl ester, (RR-SS)-2-hydroxy-4-trifluoromethyl-benzoic acid 3-(2-dimethylaminomethyl-1-hydroxy-cyclohexyl)-phenyl ester, (RR-SS)-4-chloro-2-hydroxy-benzoic acid 3-(2-dimethylaminomethyl-1-hydroxy-cyclohexyl)-phenyl ester, (RR-SS)-2-hydroxy-4-methyl-benzoic acid 3-(2-dimethylaminomethyl-1-hydroxy-cyclohexyl)-phenyl ester, (RR-SS)-2-hydroxy-4-methoxy-benzoic acid 3-(2-dimethylaminomethyl-1-hydroxy-cyclohexyl)-phenyl ester, (RR-SS)-2-hydroxy-5-nitro-benzoic acid 3-(2-dimethylaminomethyl-1-hydroxy-cyclohexyl)-phenyl ester, (RR-SS)-2',4'-difluoro-3-hydroxy-biphenyl-4-carboxylic acid 3-(2-dimethylaminomethyl-1-hydroxy-cyclohexyl)-phenyl ester, and corresponding stereoisomeric compounds, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the salts thereof and solvates, e.g. hydrochlorides.

In particular, the dosage form according to the invention preferably does not contain a psychotropically acting substance selected from the group consisting of opioids [A07DA, N01AH, N02A, R05DA, R05FA]; barbiturates [N01AF, N01AG, N03AA]; benzodiazepine derivatives [N03AE]; agents for treating opiate dependency [N07BC]; anxiolytics [N05B]; hypnotics and sedatives [N05C]; psychostimulants, agents for treating attention-deficit/hyperactivity disorder (ADHD) and nootropics [N06B]; antiemetics [A04A]; antiobesity preparations excluding diet products [A08A]; centrally acting muscle relaxants [M03B]; and antidotes [V03AB]. The abbreviations stated in square brackets here correspond to the ATC Index, as used by the WHO for classifying pharmaceutical substances (preferred version: January 2005 or 2006). Further details regarding the ATC Index may, for example, be found in U. Fricke, J. Günther, Anatomisch-therapeutisch-chemische Klassifikation mit Tagesdosen für den deutschen Arzneimittelmarkt: Methodik der ATC-Klassifikation und DDD-Festlegung [Anatomical therapeutic chemical classification with daily doses for the German pharmaceuticals market: methodology of ATC classification and DDD assignment]. ATC index with DDDs, Wissenschaftliches Institut der AOK; and Swiss Pharmaceutical Society, Index Nominum: International Drug Directory, CRC Press; 18th edition (Jan. 31, 2004).

In a preferred embodiment the dosage form according to the invention does not contain a compounds selected from the group consisting of (1) analgesics such as aspirin, acetaminophen, deflunisal and the like;
(2) anesthetics such as lidocaine, procaine, benzocaine, xylocaine and the like;
(3) antiarthritics and anti-inflammatory agents such as phenylbutazone, indomethacin, sulindac, dexamethasone, ibuprofen, allopurinol, oxyphenbutazone probenecid, cortisone, hydrocortisone, betamethasone, dexamethasone, fluocortolone, prednisolone, triamcinolone, indomethacin, sulindac and its salts and corresponding sulfide and the like;
(4) antiasthma drugs such as theophylline, ephedrine, beclomethasone dipropionate, epinephrine and the like;
(5) urinary tract disinfectives such as sulfarmethoxazole, trimethoprim, nitrofurantoin, norfloxicin, and the like;
(6) anticoagulants such as heparin, bishydroxy coumarin, warfarin and the like;
(7) anticonvulsants such as diphenylhydantoin, diazepam and the like;
(8) antidepressants such as amitriptyline, chlordiazepoxide, perphenazine, protriptyline, imipramine, doxepin and the like;
(9) agents useful in the treatment of diabetics and regulation of blood sugar, such as insulin, tolbutamide, tolazamide, somatotropin, acetohexamide, chlorpropamide and the like;
(10) antineoplastics such as adriamycin, fluouracil, methotrexate, asparaginase and the like;
(11) antipsychotics such as prochlorperazine, lithium carbonate, lithium citrate, thioridazine, molindone, fluphenazine, trifluoperazine, perphenazine, amitriptyline, triflupromazine and the like;

(12) antihypertensives such as spironolactone, methyldopa, hydralazine, clonidine, chlorothiazide, deserpidine, timolol, propanolol, metaprotol, prazosin hydrochloride, reserpine and the like;
(13) muscle relaxants such as mephalan, danbrolene, cyclobenzaprine, methocarbarnol, diazepam, succinoyl chloride and the like;
(14) antiprotozoals such as chloramphenicol, chloroquine, trimethoprim and sulfamethoxazole;
(15) spermicidals such as nonoxynol;
(16) antibacterial substances such as beta-lactam antibiotics, tetracyclines, chloramphenicol, neomycin, cefoxitin, thienamycin, gramicidin, bacitracin, sulfonamides, aminoglycoside antibiotics, tobramycin, nitrofurazone, nalidixic acid und analogs and the antimicrobial combination of fludalanine/pentizidone;
(17) antihistamines and decongestants such as perilamine, chlorpheniramine (e.g. chlorpheniramine maleate), tetrahydrozoline und antazoline;
(18) antiparasitic compounds such as ivermectin;
(19) antiviral compounds such as acyclovir and interferon;
(20) antifungal, amoebicidal, trichomonacidal agents or antiprotozoals such as polyoxyethylene nonylphenol, alkylaryl sulfonate, oxyquinoline sulfate, miconazole nitrate, sulfanil amide, candicidin, sulfisoxazole, nysatidin, clotrimazole, metronidazol and the like; and
(21) losoxanthrone, theophylline or $\square$-hydroxyethyl-theophylline (etophylline), diphenhydramine and its hydrochloride, diltiazem and its hydrochlorid, and diphenylethyl(adenosine).

In a preferred embodiment, the dosage form according to the invention contains no substances which irritate the nasal passages and/or pharynx, i.e. substances which, when administered via the nasal passages and/or pharynx, bring about a physical reaction which is either so unpleasant for the patient that he/she does not wish to or cannot continue administration, for example burning, or physiologically counteracts taking of the corresponding active ingredient, for example due to increased nasal secretion or sneezing. Further examples of substances which irritate the nasal passages and/or pharynx are those which cause burning, itching, an urge to sneeze, increased formation of secretions or a combination of at least two of these stimuli. Corresponding substances and the quantities thereof which are conventionally to be used are known to the person skilled in the art. Some of the substances which irritate the nasal passages and/or pharynx are accordingly based on one or more constituents or one or more plant parts of a hot substance drug. Corresponding hot substance drugs are known per se to the person skilled in the art and are described, for example, in "Pharmazeutische Biologie-Drogen und ihre Inhaltsstoffe" by Prof. Dr. Hildebert Wagner, 2nd., revised edition, Gustav Fischer Verlag, Stuttgart-New York, 1982, pages 82 et seq. The corresponding description is hereby introduced as a reference and is deemed to be part of the disclosure.

The dosage form according to the invention furthermore preferably contains no antagonists for the physiologically active substance (A), preferably no antagonists against psychotropic substances, in particular no antagonists against opioids. Antagonists suitable for a given physiologically active substance (A) are known to the person skilled in the art and may be present as such or in the form of corresponding derivatives, in particular esters or ethers, or in each case in the form of corresponding physiologically acceptable compounds, in particular in the form of the salts or solvates thereof. The dosage form according to the invention preferably contains no antagonists selected from among the group comprising naloxone, naltrexone, nalmefene, nalide, nalmexone, nalorphine or naluphine, in each case optionally in the form of a corresponding physiologically acceptable compound, in particular in the form of a base, a salt or solvate; and no neuroleptics, for example a compound selected from among the group comprising haloperidol, promethacine, fluphenazine, perphenazine, levomepromazine, thioridazine, perazine, chlorpromazine, chlorprothixine, zuclopenthixol, flupentixol, prothipendyl, zotepine, benperidol, pipamperone, melperone and bromperidol.

The dosage form according to the invention furthermore preferably contains no emetic. Emetics are known to the person skilled in the art and may be present as such or in the form of corresponding derivatives, in particular esters or ethers, or in each case in the form of corresponding physiologically acceptable compounds, in particular in the form of the salts or solvates thereof. The dosage form according to the invention preferably contains no emetic based on one or more constituents of ipecacuanha (ipecac) root, for example based on the constituent emetine, as are, for example, described in "Pharmazeutische Biologie-Drogen und ihre Inhaltsstoffe" by Prof. Dr. Hildebert Wagner, 2nd, revised edition, Gustav Fischer Verlag, Stuttgart, N.Y., 1982. The corresponding literature description is hereby introduced as a reference and is deemed to be part of the disclosure. The dosage form according to the invention preferably also contains no apomorphine as an emetic.

Finally, the dosage form according to the invention preferably also contains no bitter substance. Bitter substances and the quantities effective for use may be found in US-2003/0064099 A1, the corresponding disclosure of which is incorporated herein and mare a part hereof. Examples of bitter substances are aromatic oils, such as peppermint oil, *eucalyptus* oil, bitter almond oil, menthol, fruit aroma substances, aroma substances from lemons, oranges, limes, grapefruit or mixtures thereof, and/or denatonium benzoate.

The dosage form according to the invention accordingly preferably contains neither substances with a psychotropic action, nor substances which irritate the nasal passages and/or pharynx, nor antagonists for the physiologically active substance (A), nor emetics, nor bitter substances.

In a preferred embodiment, the dosage form according to the invention contains a nutritional supplement as the physiologically active substance (A). Nutritional supplements preferably contain one or more nutrients in a concentrated, measured dose form which is atypical of foodstuffs. They are intended to supplement daily food intake in those cases in which intake with the food is inadequate or supplementation is desired. The nutritional supplement is preferably selected from the group consisting of vitamins, minerals, trace elements, enzymes, fatty acids, amino acids and antioxidants. Particularly preferred nutritional supplements are vitamins, provitamins and the derivatives thereof, in particular retinol, calcitriol, tocopherol, phylloquinone, thiamine, riboflavine, folic acid, niacin (in particular nicotinamide), pantothenic acid, pyridoxal, cobalamin, L-ascorbic acid, biocytin, biotin and carotenoids.

Active Substance (A)

In a preferred embodiment, the dosage form according to the invention contains as the physiologically active substance (A) a pharmaceutically effective amount of a pharmaceutical substance (=pharmaceutical active ingredient), which justifies use of the dosage form as a pharmaceutical preparation and is the cause of the activity thereof. Pharmaceutical substances which may in principle be considered in the dosage form according to the invention are any known pharmaceutical substances, wherein the pharmaceutical substances may be present in the dosage form according to the invention as such, in the form the derivatives thereof, in particular esters or ethers, or in each case in the form of corresponding physiologically acceptable compounds, in particular in the form of the corresponding salts or solvates thereof, as racemates or in a form enriched in one or more stereoisomers (enantiomers or diastereomers).

Particularly preferably the dosage form according to the invention contains a substance (A) or two or more substances (A) selected from the group consisting of agents for the treatment and prevention of diseases of the alimentary system and metabolism [A]; in particular stomatological preparations [A01], agents for the treatment and prevention of acid-related disorders [A02], agents for the treatment and prevention of functional gastrointestinal tract disorders [A03], serotonin 5 $HT_3$ antagonists [A04AA], antihistamine preparations [A04AB], agents for bile and liver therapy [A05], laxatives [A06], intestinal antiinfectives [A07A], intestinal adsorbents [A07B], electrolytes with carbohydrates [A07C], intestinal antiinflammatory agents [A07E], microbial antidiarrhoeals [A07F], digestives including enzymes [A09], drugs used in diabetes [A10], vitamins [A11], minerals [A12], anabolic agents for systemic applications [A14] and appetite stimulants [A15]; agents for the treatment and prevention of diseases of the blood and the blood forming organs [B]; in particular antithrombotic agents [B01], antihaemorrhagics [B02], antianaemic preparations [B03] and other haematological agents [B06];

agents for the treatment and prevention of diseases of the cardiovascular system [C]; in particular agents for cardiac therapy [C01], antihypertensives [C02], diuretics [C03], peripheral vasodilatators [C04], vasoprotectives [C05], antihypotensives [C06A], D-adrenoceptor antagonists [C07], calcium channel blockers [C08], agents acting on the renin-angiotensin system [C09] and lipid reducing agents [C10];

dermatologicals [D]; in particular antifungals for systemic use [D01B], antipsoriatics for systemic use [D05B], antiacne preparations for systemic use [D10B];

agents for the treatment and prevention of diseases of the genitourinary system and sex hormones [G]; in particular gynaecological antiinfectives and antiseptics [G01], oxytocics [G02A], sympathomimetic labour repressants [G02CA], prolactin inhibitors [G02CB], hormonal contraceptives for systemic use [G03] and urologicals [G04];

systemic hormone preparations excluding sex hormones and insulins [H]; in particular pituitary and hypothalamic hormones and analogue [H01], corticosteroids for systemic use [H02], thyroid preparations [H03], pancreatic hormones [H04], and agents for regulating calcium homeostatis [H05];

antiinfectives for systemic use [J]; in particular antibiotics for systemic use [J01], antimycotics for systemic use [J02], antimycobacterials [J04], antivirals for systemic use [J05], immune sera and immunoglobulins [J06], and vaccines [J07]);

antineoplastic and immunomodulating agents [L] (in particular antineoplastistic agents [L01], agents for endocrine therapy [L02], immunostimulants [L03] and immunosuppressive agents [L04];

agents for the treatment and prevention of diseases of the musculo-skeletal system [M]; in particular antiinflammatory and antirheumatic agents [M01], peripherally acting muscle relaxants [M03A], directly acting muscle relaxants [M03C], antigout preparations [M04] and agents for the treatment of bone diseases [M05];

agents for the treatment and prevention of diseases of the nervous system [N]; in particular salicylic acid the derivatives thereof [N02BA], pyrazolones [N02BB], anilides [N02BE], ergot alkaloids [N02CA], corticosteroid derivatives [N02CB], selective serotonin-5 $HT_1$ agonists [N02CC], hydantoin derivatives [N03AB], oxazolidine derivatives [N03AC], succinimide derivatives [N03AD], carboxamide derivatives [N03AF], fatty acid derivatives [N03AG], antiparkinson drugs [N04]), antipsychotics [N05A], antidepressants [N06A], antidementia drugs [N06D], parasympathomimetics [N07A] and antivertigo preparations [N07C];

antiparasitic products, insecticides and repellents [P]; in particular antiprotozoals [P01], anthelmintics [P02] and ectoparasiticides, including scabicides, insecticides and repellents [P03];

agents for the treatment and prevention of diseases of the respiratory system [R]; in particular nasal preparations [R01], throat preparations [R02], drugs for obstructive airways diseases [R03], expectorants, excluding combinations with cough suppressants [R05C] and antihistamines for systemic use [R06];

agents for the treatment and prevention of diseases of the sensory organs [S]; in particular otologicals [S02]; and general diet products [V06] and therapeutic radiopharmaceuticals [V10], wherein the abbreviations stated in square brackets here correspond to the ATC Index, as used by the WHO for classifying pharmaceutical substances (preferred version: January 2005 or 2006).

The dosage form according to the invention preferably contains a substance (A) or two or more substances (A) selected from the group consisting of 4-aminomethylbenzoic acid, abacavir, abamectin, abciximab, abibendan, abrin, acamprosat, acarbose, acebutolol, aceclidine, aceclofenac, acediasulfone, acemetacin, acenocoumarol, acetazolamide, acetoacetic acid, acetyldigoxin, acetylandromedol, acetylcysteine, □-acetyldigoxin, acetylhistamine, acetylsalicylic acid, acetylthiocholine, aciclovir, acipimox, acitretin, aclarubicin, aconitine, acriflavinium chloride, acrivastine, actinoquinol, acylaminopenicillin, adalimumab, adapalene, adefovir, adefovir dipivoxil, adenosine, adenosine phosphate, adenosine triphosphate, adipiodone, adrenalin, aescin, agalsidase alfa, agalsidase beta, agaricic acid, ajmaline, alanine, albendazole, alcuronium, aldesleukin, aldosterone, alemtuzumab, alendronic acid, alfacalcidol, alfuzosin, algeldrate F, alitretinoin, alizapride, allantoin F, allopurinol, allyl isorhodanate, almasilate F, almotriptan, □-acetyldigoxin, alprenolol, alprostadil, alteplase, aluminium glycinate F, aluminium hydroxide F, aluminium phosphate F, aluminium triformate, amantadine, ambazone, ambroxol, ambutonium bromide, formic acid, amicacin, amidephrine, amidotrizoic acid, amifostine, amikacin, amiloride, aminoacetic acid, aminoglutethimide, aminophylline, aminoquinuride, amiodarone, amisulpride, amitriptyline, amitryptiline, amlodipine, amorolfine, amoxicillin, amphotericin B, ampicillin, amprenavir, amylmetacresol, amyl nitrite, anagrelide, anakinra, anastrozole, ancrod, anistreplase, antazoline, antithrombin III, apomorphine, apraclonidine, aprepitant, aprindine, aprotinin, arcitumomab, arginine, aripiprazole, arsenic trioxide, artemether, articaine, ascorbic acid, asparagine, L-asparaginase, aspartic acid, atazanavir, atenolol, atomoxetine, atorvastatin, atosiban, atovaquone, atracurium, atracurium besylate, atropine, auranofin, azapropazone, azathioprine, azelaic acid, azelastine, azidothymidine, azithromycin, azlocillin, aztreonam, N2 alanyl levoglutamide, p-aminosalicylic acid, bacampicillin, bacitracin, baclofen, balsalazide, bambuterol, bamethan, bamipine, barbexaclone, barium sulfate F, barnidipine, basiliximab, batroxobin, becaplermin, beclomethasone, bendamustine, befunolol, bemiparin, benactyzine, benazepril, bencyclane, bendazac, bendroflumethiazide, benproperine, benserazide, benzaseride, benzathine, benzatropine, benzbromarone, benzocaine, benzoyl peroxide, benzyclane, benzydamine, benzylpenicillin, benzylphenyl glycolate, betacarotene, betahistidine, betahistine, betamethasone, bethanechol, betaxolol, bethanechol chloride, betiatide, bevacizumab, bexarotene, bezafibrate, bibenzonium bromide, bicalutamide, bicisate, bifonazole, bimatoprost, biperiden, bisoprolol, bivalirudin, bleomycin, blood clotting factor VII, VIII, IX, X, XIII, bornapine, bornaprine, bortezomib, bosentan, botulinum toxin type B, brimonidine, brinzolamide, brivudin, bromhexine, bromocriptine, bromperidol, brompheniramine, brotizolam, budesonide, budipine, bufexamac, buflomedil, bumetanide, bunazosin, buphenine, bupivacaine, bupranolol, bupropion, buserelin, buspirone, busulfan, butalamine, butanilicaine, butenafine, butethamate, butinoline, butizide, butylscopolaminium, 5-chlorcarvacrol, C1 esterase inhibitor, cabergoline, cadexomer iodine, cafedrine, calcipotriol, calcitonin, calcitriol, camylofine, candesartan cilexetil, canrenoic acid, capecitabine, capreomycin, capsaicin, captopril, carazolol, carbaldrate F, carbamazepine, carbasalate calcium, carbenoxolone, carbidopa, carbimazole, carbinoxamine, carboplatin, carglumic acid, carmustine, caroverine, carteolol, carvedilol, caspofungin, cefaclor, cefadroxil, cefalexin, cefaloridine, cefamandole, cefazolin, cefdinir, cefepime, cefetamet-pivotil, cefixime, cefodizime, cefoperazone, cefotaxime, cefotiam, cefoxitin, cefpirome, cefpodoxime, cefpodoxime-proxetil, cefprozil, ceftazidime, ceftibuten, ceftizoxime, ceftriaxone, cefuroxime, celecoxib, celiprolol, certoparin, cetirizine, cetrimide, cetrimonium bromide, cetrorelix, cetuximab, cetylpyridinium, chenodeoxycholic acid, quinidine, quinine, quinine iron citrate F, quinine tannate F, chlorambucil, chloramphenicol, chlorobutynol, chlorhexidine, chlormidazole, chlorobutanol, chloroquine, chloroxylenol, chlorphenamine, chlorphenesin, chlorphenoxamine, chlorpromazine, chlorprotheaxine, chlorprothixine, chlortalidone, chlortetracycline, chlorzoxazone, choline, chondroitin sulfate, choriogonadotropin alfa, chorionic gonadotropin, chrysarobin, chymotrypsin, ciclesonide, cicletanine, ciclopirox, ciclosporin, cidofovir, cilastatin, cilazapril, cimetidine, cinacalcet, cinchocaine, cinnarizine, cinolazepam, ciprofloxacin, cisapride, cisatracurium besylate, cisplatin, citalopram, citicoline, cladribine, clarithromycin, clavulanic acid, clemastine, clenbuterol, clindamycin, clioquinol, clobetasol, clobetasone, clobutinol, clocortolone, clodronic acid, Clofibrate, clomifene, clomipramine, clonazepam, clonidine, clopamide, clopidogrel, clostebol acetate, clostridium botulinum, clotrimazole, cloxiquine, clozapine, cocarboxylase, colchicine, colecalciferol, colesevelam, colestipol, colestyramine, colfosceril palmitate, colistin, zinc eyewash F, corticorelin, corticotrophin, cortisone, cresol, croconazole, cromoglicic acid, crotamiton, cryofluorane, coumarin, cyanamide, cyanocobalamin, cyclizine, cyclobutyrol, cyclopentolate, cyclophosphamide, cycloserine, cyproheptadine, cyproterone, cysteine, cytarabine, cytarabine, 2,4-dichlorobenzyl alcohol, 2-diethylaminoethanol, dacarbazine, daclizumab, dactinomycin, dalfopristin, dalteparin, danaparoid, danazol, dantrolene, dapiprazole, dapsone, darbepoetin alfa, darifenacin, Daunorubicin, deanol, deanolace, decarbazine, dectaflur F, deferiprone, deferoxamine, delapril, demeclocycline, denaverine, depreotide, dequalinium, desflurane, desipramine, desirudin, deslanoside, desloratadine, desmeninol, desmopressin, desogestrel, desoximetasone, deoxyribonuclease, detajmium, dexamethasone, dexchlorpheniramine, dexibuprofen, dexketoprofen, dexrazoxane, dextran, dextromethorphan, diacerein, diacetyl morphine, dibenzepin, dibotermin alfa, diclofenac, diclofenamide, didanosine, dienestrol, dienogest, diethylstilbestrol, difloxacin, diflucortolone, diflunisal, digitoxin, digoxin, dihydralazine, dihydroergocornine, dihydroergocristine, dihydroergocryptine, dihydroergotamine, dihydroergotoxine, dihydrotachysterol, diisopropylamine, dipotassium clorazepate, diltiazem, dimenhydrinate, dimepranol, dimercaprol, dimethyl sulfoxide, dimethindene, disodium selenite, dinoprost, dinoprostone, diosmin, diphenhydramine, diphenoxylate, diphenylpyraline, dipivefrine, diprophylline, dipyridamole, disopyramide, dinitrogen monoxide, distigmine, disulfiram, dithranol, dixyrazine, D-norpseudoephedrine, dobesilate calcium, dobutamine, docetaxel, dofetilide, dolasetron, domperidone, donepezil, dopamine, dopexamine, dornase alfa, dorzolamide, dosulepin, doxapram, doxazosin, doxepin, doxorubicin, doxycycline, doxylamine, drofenine, droperidol, drospirenone, drotrecogin alfa, duloxetine, dutasteride, dydrogesterone, N,N'-dihydroxymethyl urea, ebastine, econazole, ecothiopate iodide, efalizumab, efavirenz, eflornithine, iron(III) ammonium citrate F, superparamagnetic iron oxide, elcatonin, eletriptan, emedastine, emepronium, emepronium carrageenate, emetine, emtricitabine, enalapril, enalaprilat, enflurane, enfuvirtide, enoxacin, enoxaparin, entacapone, ephedrine, ephedrine racephedrine, epinastine, epinephrine, epirubicin, eplerenone, epoetin alfa, epoetin beta, epoetin delta, epoprostenol, eprazinone, eprosartan, eptacog alfa, eptifibatide, eptotermin alfa, erdosteine, ergocalciferol, ergometrine, ergotamide, ergotamine, ertapenem, erythromycin, escitalopram, esmolol, esomeprazole, estradiol, estramustine, estriol, estrone, etacrynic acid, etamivan, etanercept, ethacridine, ethambutol, ethaverine, ethinylestradiol, ethisterone, ethosuximide, etidronic acid, etilefrine, etodolac, etofenamate, etofibrate, etofylline, etomidate, etonogestrel, etoposide, etoricoxib, everolimus, exametazime, exemestane, ezetimibe, 3-fluorotyrosine, famciclovir, famotidine, felbamate, felbinac, felodipine, fenbufene, fendiline, fenofibrate, fenoterol, fenticonazole, fexofenadine, fibrinogen, fibrinolysin, filgrastim, finasteride, flavoxate, flecainide, flucloxacillin, fluconazole, fludarabine, fludeoxyglucose [$^{18}$F], fludrocortisone, flufenamic acid, flumazenil, flumetasone, flunarizine, flunisolide, fluocinolone acetonide, fluocinonide, fluocortolone, fluophenozine, fluorescein dilaurate, fluorescein sodium, fluorometholone, fluorouracil, fluorophosphoric acid, fluorosilane, fluoxetil, fluoxetine, flupentixol, fluphenazine, flupirtine, fluprednidene, flurbiprofen, flutamide, fluticasone, flutrimazole, fluvastatin, fluvoxamine, folic acid, follitropin alfa, follitropin beta, folic acid, fomepizole, fomivirsen, fondaparinux, formestane, formoterol, fosamprenavir, foscarnet, fosfestrol, fosfomycin, fosinopril, fosphenytoin, fotemustine, framycetin, framycetin, frovatriptan, fulvestrant, furosemide, fusafungine, fusidic acid, fytic acid, gabapentin, gadobenic acid, gadobutrol, gadodiamide, gadopentetic acid, gadoteridol, gadoteric acid, gadoteric acid-meglumine, gadoxetic acid, galantamine, gallopamil, ganciclovir, ganirelix, gatifloxacin, gemcitabine, gemfibrozil, gentamicin, gepefrine, gestodene, glatiramer, glibenclamide, glibornuride, gliclazide, glimepiride, glipizide, gliquidone, glisoxepide, glucagon, glutamine, glutamic acid, glycopyrronium, glycopyrronium bromide, glycyrrhetinic acid, gonadorelin, goserelin, gramicidin, granisetron, grepafloxacin, griseofulvin, g-strophanthin, guajacol, guanethidine, guanfacine, $^{13}C$ urea, 4-hydroxybutyric acid, halcinonide, halofantrine, halometasone, haloperidol, halothane, haem, haematoporphyrin, heparin, hepatitis B vaccine, heptaminol, hexobarbital, hexobendine, hexoprenaline, histamine, histidine, homatropine, homofenazine, human albumin, hyaluronidase, hydralazine, hydrastinine, hydroquinone, hydrochlorothiazide, hydrocortisone, hydrotalcite F, hydroxocobalamin, hydroxycarbamide, hydroxychloroquine, hydroxycine, hydroxylamine, hydroxyprogesterone, hydroxyzine, hymecromone, ibandronic acid, ibopamine, ibritumomab tiuxetan, ibuprofen, ibutilide, idarubicin, ifosfamide, iloprost, imatinib, imatinib mesylate, imidapril, imiglucerase, imipenem, imipramine, imiquimod, immunocyanin, indanazoline, indapamide, indinavir, indium chloride [$^{111}$In], indobufen, indometacin, indoramin, infliximab, inosine, insulin, insulin aspart, insulin detemir, insulin glargine, insulin glulisine, insulin lispro, interferon alfa, interferon alfa-2b, interferon alfacon-1, interferon beta, interferon beta-1a, interferon beta-1b, interferon gamma, iobitridol, iodine, iodamide, iodixanol, ioflupane [$^{123}$I], iohexol, iomeprol, iopamidol, iopentol, iopromide, iosarcol, iotrolan, iotroxic acid, ioversol, ioxaglic acid, ioxitalamic acid, ipatropium, irbesartan, irinotecan, irinotecan, isepamicin, isoaminile, isoconazole, isoflurane, isoleucine, isoniazid, isonicotinic acid, isoprenaline, isosorbide, isospaglumic acid, isotretinoin, isoxsuprine, isradipine, itraconazole, josamycin, potassium permanganate, kallidinogenase, kanamycin, kawain, kebuzone, ketamine, ketoconazole, ketoprofen, ketorolac, ketotifen, collagenase, creosote, labetalol, lacidipine, lactitol, lamivudine, lamotrigine, lanreotide, lansoprazole, laronidase, latanoprost, leflunomide, lenograstim, lepirudin, lercanidipine, letrozole, leucine, leuprorelin, levallorphan, levamisole, levetiracetam, levobunolol, levobupivacaine, levocabastine, levocetirizine, levodopa, levofloxacin, levofolinate calcium, levomepromazine, levomethadyl, levonorgestrel, levopropylhexedrine, levosimendan, levothyroxine, lidocaine, lincomycin, lindane, linezolid, liothyronine, lisinopril, lisuride, lobeline, lodoxamide, lofepramine, lomefloxacin, lomustine, lonazolac, loperamide, lopinavir, loratadine, lorazepam oxide, lornoxicam, losartan, loteprednole, lovastatin, lumefantrine, lutropin alfa, lymecycline, lynestrenol, lypressin, lysine, magaldrate F, magnesium pidolate, magnesium L-aspartate, mangafodipir, manidipine, maprotiline, mebendazole, mebeverine, meclofenoxate, mecloxamine, meclozine, medrogestone, medroxyprogesterone, mefenamic acid, mefloquine, megestrol, melagatrane, melitracen, melperol, melperone, melphalan, memantine, menadione, mepacrine, mepartricin, mephenytoin, mepindolol, mepivacaine, mepyramine, mequinol, mercaptamine, mercaptopurine, meropenem, mesalazine, mesna, mesterolone, mesuximide, metaclazepam, metamizole, metamphetamine, metenolone, metenolone acetate, metformin, methanthelinium, methazolamide, methenamine, methionine, methohexital, methotrexate, 5-methoxypsoralen, 8-methoxypsoralen, methyl 5-aminolevulinate, methylbenactyzium bromide, methyldopa, methylergometrine, methylprednisolone, methylrosanilinium, methyltestosterone, methylthionium chloride, methysergide, metildigoxin, metipranolol, metoclopramide, metoprolol, methixene, metronidazole, mexiletine, mezlocillin, mianserine, miconazole, midodrine, mifepristone, miglitol, miglustat, milnacipran, milrinone, miltefosine, minocycline, minoxidil, mirtazapine, misoprostol, mitobronitol, mitomycin, mitotane, mitoxantrone, mivacurium chloride, mivacuronium, mizolastine, moclobemide, moexipril, molgramostim, molsidomine, mometasone, monochloroacetic acid, montelukast, moroctocog alfa, moxaverine, moxifloxacin, moxonidine, mupirocin, mycophenolate mofetil, nadifloxacin, nadrolon decanonate, nadroparin calcium, naftidrofuryl, naftifine, nalbuphine, nalide, nalmefene, nalmexone, naloxone, naltrexone, naluphine, naphazoline, 2-naphthol, naproxen, naratriptan, naratriptan, nateglinide, sodium aurothiomalate, sodium phenylbutyrate, sodium fluoride, sodium hyaluronate, sodium iodide [$^{131}$I], sodium molybdate [$^{99}$Mo], sodium phenylbutyrate, n-butyl-p-aminobenzoate, N-butylscopolaminium bromide, nebivolol, nedocromil, nefazodone, nefopam, nelfinavir, neomycin, neostigmine, neostigmine methylsulfate, netilmicin, nevirapine, n-heptyl-2-phenyl glycinate, nicardipine, nicergoline, nicethamide, niclosamine, nicoboxil, nicorandil, nicotine, nicotine aldehyde, nicotinamide, nicotine resinate, nicotinic acid, nicotinic acid ester, nicotinyl alcohol, nifedipine, niflumic acid, nifuratel, nilvadipine, nimesulide, nimodipine, nimorazole, nimustine, nisoldipine, nitisinone, nitrendipine, nitric oxide, nitrofurantoin, nitroglycerine, nizatidine, N-methylephedrine, nonacog alfa, nonivamide, noradrenalin, norelgestromin, norepinephrine, norethisterone, norfenefrine, norfloxacin, norgestimate, norgestrel, nortriptyline, noscapine, nystatin, obidoxime chloride, octafluoropropane, octocog alfa, octodrine, octreotide, odansetron, ofloxacin, olaflur F, olanzapine, olmesartan medoxomil, olopatadine, olsalazine, omeprazole, omoconazole, ondansetron, opipramol, oral cholera vaccine, orciprenaline, orlistat, ornipressin, orphenadrine, oseltamivir, osteogenic protein-1: BMP-7, oxaprozin, oxatomide, oxcarbazepine, oxedrine tartrate, oxetacaine, oxiconazole, oxilofrine, oxitropium, 2-oxo-3-methylbutyric acid, 2-oxo-3-methylvaleric acid, 2-oxo-3-phenylpropionic acid, 2-oxo-4-methylvaleric acid, oxprenolol, oxybuprocaine, oxybuprocaine, oxybutynin, oxybutynin, oxyfedrine, oxymetazoline, oxytetracycline, oxytocin, paclitaxel, palinavir, palivizumab, palonosetrone, pamidronic acid, pancuronium, pantoprazole, papaverine, paracetamol, paraldehyde, parecoxib, paricalcitol, parnaparin, paromomycin, paroxetine, pefloxacin, peg-filgrastim, peginterferon alfa, pegvisomant, pemetrexed, penbutolol, penciclovir, penfluridol, penicillamine, benperidol, pentaerithrityl tetranitrate, pentamidine, pentetrazol, pentetreotide, pentosan polysulfate sodium, pentoxifylline, pentoxyverine, perazine, perchloric acid, perflenapent, perflisopent, perflutren, pergolide, perindopril, perphenazine, phenacetin, phenamazid, phenazone, phenazopyridine, pheniramine, phenol, phenolphthalein, phenoxybenzamine, phenoxymethylpenicillin, phenprocoumon, phentolamine, phenylalanine, phenylbutazone, phenylephrine, phenylpropanolamine, phenyltoloxamine, phenytoin, phloroglucinol, pholedrine, phthalylsulfathiazole, physostigmine, phytomenadione, phytosterol, picric acid, pilocarpine, pimecrolimus, pimozide, pinaverium bromide, pindolol, pioglitazone, pipamperone, pipazetate, pipecuronium bromide, pipemidic acid, pipenzolate, piperacillin, piprinhydrinate, piracetam, pirarubicin, pirbuterol, pirenzepine, piritramide, piroxicam, pivmecillinam, pizotifen, podophyllotoxin, polidocanol, polycarbophil, polyestradiol phosphate, polymyxin B, polymyxin-B, polystyrenesulfonic acid, porfimer, prajmaline, prajmalium bitartrate, pramipexole, pranoprofen, prasterone, pravastatin, prazepam, prazosin, prednicarbate, prednisolone, prednisone, pregabalin, proglumetacin, pridinol, prilocaine, primaquine, primidone, prithipendyl, procaine, procainamide, procarbazil, procarbazine, procyclidin, progesterone, proglumetacin, proglumide, proguanil, proline, promethazine, propacetamol, propafenon, propanolol, propicillin, propiverine, propofol, propranolol, propylthiouracil, propyphenazone, protamine, protamine sulfate, protein C, prothipendyl, prothrombin, protionamide, protirelin, proxymetacaine, proxyphylline, pseudoephedrine, Pulmonal, pyrantel, pyrazinamide, pyridostigmine, pyridostigmine bromide, pyridoxine, 3-pyridylmethanol, pyrimethamine, pyrithione zinc, pyritinol, pyrogallol, pyrvinium, pyrvinium embonate, mercury amide chloride, quetiapine, quinagolide, quinapril, quinupristin, rabeprazole, racephedrine, racecadotrile, raloxifene, raltitrexed, ramipril, ranitidine, rasagiline, rasburicase, raubasine, reboxetine, repaglinide, reproterol, reserpine, resorcinol, reteplase, retinol, reviparin, ribavirin, riboflavin, rifabutin, rifampicin, rifamycin, rifaximin, rilmenidine, riluzole, rimexolone, risedronic acid, risperidone, ritonavir, rituximab, rivastigmine, rizatriptan, rocuronium bromide, rofecoxib, ropinirole, ropivacaine, ropivacaine, rosiglitazone, red mercuric sulfide F, roxatidine, roxithromycin, salbutamol, salicylic acid, salmeterol, nitric acid, nitrous acid, salverine, samarium [$^{153}$Sm] lexidronam, saquinavir, sulfur hexafluoride, scopolamine, selegiline, selenium sulfide, serine, sermorelin, sertaconazole, sertindole, sertraline, sevelamer, sevoflurane, sibutramine, silver chloride F, sildenafil, silibinin, simvastatin, sirolimus, formaldehyde solution, solifenacine, somatostatin, somatropin, sotalol, spaglumic acid, sparteine, spectinomycin, spiramycin, spirapril, spironolactone, stavudine, streptodornase, streptokinase, streptomycin, strontium ranelate, strontium chloride, strychnine, sucralfate F, sulbactam, sulesomab, sulfacetamide, sulfadiazine, sulfadimethoxine, sulfaguanidine, sulfamerazine, sulfamethoxazole, sulfamethoxydiazine, sulfametrole, sulfanilamide, sulfasalazine, sulfathiazole, sulfisomidine, sulindac, sulodexide, sulfur hexafluoride, sulpiride, sulprostone, sultamicillin, sultiame, sumatriptan, suxamethonium, tacalcitol, tacrolimus, tadalafil, tamoxifen, tamsulosin, tasonermin, taurolidine, tazarotene, tazobactam, tegafur, teicoplanin, telithromycin, telmisartan, temoporfin, temozolomide, tenecteplase, teniposide, tenofovir, tenofovir disoproxil, tenoxicam, terazosin, terbinafine, terbutaline, terfenadine, teriparatide, terizidone, terlipressin, testosterone, testosterone propionate, testosterone undecanoate, tetracaine, tetracosactide, tetracycline, tetrafluoroborate-1+, tetrofosmin, tetryzoline, thallium chloride [$^{201}$Tl], theobromine, theodrenaline, theodrenaline, theophylline, thiamazole, thiamine, thiethylperazine, thiocolchicoside, thiopental, thioridazine, thiotepa, threonine, thrombin, thrombokinase, thymol, thyrotropin alfa, tiagabine, tianeptine, tiapride, tibolone, ticlopidine, tiludronic acid, timolol, tinzaparin, tioconazole, tioguanine, tiotropium bromide, tirilazad, tirofiban, tisopurine, tizamidine, tizanidine, tobramycin, tocainide, tolazoline, tolbutamide, tolcapone, tolfenamic acid, tolmetin, tolperisone, tolterodine, topiramate, topotecan, torasemide, toremifene, tramazoline, trandolapril, tranexamic acid, tranylcypromine, trapidil, trastuzumab, travoprost, trazodone, tretinoin, triamcinolone, triamcinolone acetonide, triamterene, trichloroacetic acid, triethylperazine, trifluoperazine, triflupromazine, trihexyphenidyl, trimebutine, trimecaine, trimegestone, trimetazidine, trimethoprim, trimipramine, tripelennamine, triprolidine, triptorelin, tritoqualine, trofosfamide, tromantadine, trometamol, tropicamide, tropisetron, trospium, tryptophan, tubocurarine chloride, tulobuterol, tyloxapol, tyrosine, tyrothricin, unoprostone, urapid, urapidil, urokinase, ursodeoxycholic acid, valaciclovir, valdecoxib, valganciclovir, valine, valproic acid, valsartan, vancomycin, vardenafil, vecuronium, vecuronium bromide, venlafaxine, verapamil, verteporfin, vigabatrin, viloxazine, vinblastine, vincamine, vincristine, vindesine, vinorelbine, vinpocetine, viquidil, voriconazole, votumumab, hydrogen peroxide, xantinol nicotinate, ximelagatrane, xipamide, xylometazoline, yohimbine, yttrium $^{90}$Y chloride, zalcitabine, zaleplon, zanamivir, zidovudine, zinc acetate dihydrate, zinc chloride, zinc citrate, zinc sulfate, ziprasidone, zofenopril, zoledronic acid, zolmitriptan, zolpidem, zolpidem tartrate, zonisamide, zopiclone, zotepine, zucklopantexol, and zuclopenthixol.

The above-stated compounds are predominantly stated by their international nonproprietary name (INN) and are known to the person skilled in the art. Further details may be found, for example, by referring to International Nonproprietary Names (INN) for Pharmaceutical Substances, World Health Organization (WHO).

In a preferred embodiment the dosage form according to the invention contains one physiologically active substance (A) or more physiologically active substances (A) selected from the group consisting of 1,1-(3-dimethylamino-3-phenylpentamethylen)-6-fluor-1,3,4,9-tetrahydropyrano[3,4-b]indole, in particular its hemicitrate; 1,1-[3-dimethylamino-3-(2-thienyl)pentamethylen]-1,3,4,9-tetrahydropyrano[3,4-b]indole, in particular its citrate; and 1,1-[3-dimethylamino-3-(2-thienyl)pentamethylen]-1,3,4,9-tetrahydropyrano [3,4-b]-6-fluoro-indole, in particular its hemicitrate. These compounds are known, for example, from WO 2004/043967 or WO 2005/066183. The corresponding descriptions are hereby introduced as a reference and are deemed to be part of the disclosure.

Wax

At least one natural, semi-synthetic or synthetic wax (D) (=component (D)) may be used in order to achieve the necessary breaking strength of the dosage form according to the invention. Preferred waxes are those with a softening point of at least 50° C., or of at least 55° C., or of at least 60° C., or of at least 65° C. or of at least 70° C. Carnauba wax and beeswax are particularly preferred. Carnauba wax is very particularly preferred. Carnauba wax is a natural wax which is obtained from the leaves of the carnauba palm and has a softening point of at least 80° C. When the wax component is additionally used, it is used together with at least one polymer (C) in quantities such that the dosage form has a breaking strength of at least 400 N, preferably of at least 500 N.

Auxiliary Substances (B)

Auxiliary substances (B) which may be used are those known auxiliary substances which are conventional for the formulation of solid dosage forms. These are preferably plasticisers, such as triacetin and polyethylene glycol, preferably a low molecular weight polyethylene glycol, auxiliary substances which influence active ingredient release, preferably hydrophobic or hydrophilic, preferably hydrophilic polymers, very particularly preferably hydroxypropylmethylcellulose, and/or antioxidants. Polymers, particularly preferably cellulose ethers, cellulose esters and/or acrylic resins are preferably used as hydrophilic matrix materials. Ethylcellulose, hydroxypropylmethylcellulose, hydroxypropylcellulose, hydroxymethylcellulose, poly(meth)acrylic acid and/or the derivatives thereof, such as the salts, amides or esters thereof are very particularly preferably used as matrix materials.

Suitable antioxidants are ascorbic acid, butylhydroxyanisole (BHA), butylhydroxytoluene (BHT), salts of ascorbic acid, monothioglycerol, phosphorous acid, vitamin C, vitamin E and the derivatives thereof, sodium bisulfite, particularly preferably butylhydroxytoluene or butylhydroxyanisole and α-tocopherol.

The antioxidant is preferably used in quantities of 0.01 to 10 wt. %, preferably of 0.03 to 5 wt. %, relative to the total weight of the dosage form.

Dosage Forms

The dosage forms according to the invention are distinguished in that, by virtue of their resistance to crushing, they cannot be pulverised with the assistance of conventional comminution tools, such as a pestle and mortar. Overdosing is consequently virtually ruled out. However, in order to increase the resistance to crushing of the dosage form still further, the dosage forms according to the invention may contain further resistance-to-crushing-enhancing agents as auxiliary substances (B).

The dosage form according to the invention is preferably solid and suitable for taking orally, vaginally or rectally, preferably orally. The dosage form is preferably not in film form. In a further preferred embodiment, the dosage form according to the invention assumes the form of a tablet, a capsule or the form of an oral osmotic therapeutic system (OROS).

In a preferred embodiment, the dosage form according to the invention assumes the form of a tablet.

The dosage form according to the invention may assume multiparticulate form, preferably the form of microtablets, microcapsules, micropellets, granules, spheroids, beads or pellets, optionally packaged in capsules or press-formed into tablets, preferably for oral administration. The individual particles themselves exhibit a resistance to crushing of at least 400 N, optionally also a tablet obtained therefrom.

The multiparticulate forms preferably have a size or size distribution in the range from 0.1 to 3 mm, particularly preferably in the range from 0.5 to 2 mm. Depending on the desired dosage form, conventional auxiliary substances (B) are optionally also used for the formulation of the dosage form.

Process of Preparation

The dosage form according to the invention may be produced by different processes, which are explained in greater detail below; the present invention also relates to dosage forms that are obtainable by any of the processes described here below:

In general, the process for the production of the dosage form according to the invention preferably comprises the following steps:

(a) mixing of component (A), (C), optionally (B) and optionally (D);

(b) optionally preforming the mixture obtained from step (a), preferably by applying heat and/or force to the mixture obtained from step (a), the quantity of heat supplied preferably not being sufficient to heat component (C) up to its softening point;

(c) hardening the mixture by applying heat and force, it being possible to supply the heat during and/or before the application of force and the quantity of heat supplied being sufficient to heat component (C) at least up to its softening point;

(d) optionally singulating the hardened mixture;

(e) optionally shaping the dosage form; and (f) optionally providing a film coating.

Heat may be supplied directly or with the assistance of ultrasound. Force may be applied and/or the dosage form may be shaped for example by direct tabletting or with the assistance of a suitable extruder, particularly by means of a screw extruder equipped with two screws (twin-screw-extruder) or by means of a planetary gear extruder.

In general, when the dosage formed is prepared utilizing an extruder, the following parameters are critical in extrusion processes and have the consequences described.

1. Throughput (Kg Per Hour)

If the throughput is too low the extruder is not correctly filled and the material is stressed thereby affecting the viscosity and the release profile of the final product. If the throughput is too high, the load of the extruder is higher than 100% and the extruder shuts down automatically; and if the throughput is tolerable but close to the upper limit significant expansion of the extruded strand occurs (also known as "die swelling").

2. Screw Geometry

A minimum number of kneading elements is required in order to obtain a homogeneous mixture; if the number is too high, the material is stressed thereby affecting the viscosity and the release profile of the final product. The number and lead of the conveying elements influences the homogeneity of the mixture and its residence time in the extruder and controls the increase of the pressure in front of the die. Mixing elements improve the homogeneity of the mixture; and eccentric screw heads allow for a continuous discharge of the extrudate without density variations.

3. Die and Merge Element Geometry

The geometry of the element which merges the extrusion strands in front of the die, and geometry of the die itself, the residence time in said element, and the ratio length of the die to diameter of the die influence the compression of the material thereby affecting the melt pressure. The die pressure depends on revolution, throughput and melt temperature and affects the viscosity and the release profile of the final product.

4. Temperature (Melt Zones)

The feeding cylinder should not be heated to prevent the starting material from melting in the feeder and causing an accumulation. The number of cylinders is variable, the longer the extruder the longer the residence time. The temperature of the cylinders (except feeding cylinder) destroys the material if it is too high; if too low the material dos not sufficiently melt thereby resulting in an inhomogeneous mixture and degradation. If the die temperature, if separately set too low, causes the "extrusion skin" to not properly form thereby making further processing of the extrudate difficult.

5. Revolution of the Extruder

If the extruder revolution speed is too high the material is stressed thereby affecting the viscosity and the release profile of the final product. If the extruder revolution speed is too low the load of the extruder is higher than 100% and the extruder shuts down automatically; and inter alia the residence time depends on the revolution.

6. Arrangement of Cylinders

The position of feeding cylinder, the length of extruder are important. The degassing should be located close to the feeder in order to avoid air pockets in the product; and if one of the components is thermo-labile it may be separately fed into one of the rear cylinders.

7. Temperature of Cooling Water

Cooling of the engine and control of the temperature of the extrusion cylinders are important parameters.

The following process variants are preferred embodiments of the various techniques which may be utilized to produce the dosage forms:

Process Embodiment 1

In this embodiment, the dosage form according to the invention is preferably produced without using an extruder by preferably mixing components (A), (C), optionally (B) and the optionally present component (D) and, optionally after granulation, shaping the resultant mixture by application of force to yield the dosage form with preceding and/or simultaneous exposure to heat.

This heating and application of force for the production of the dosage form proceeds without using an extruder.

Components (A), (C), optionally (B) and optionally (D) are mixed in a mixer known to the person skilled in the art. The mixer may, for example, be a roll mixer, shaking mixer, shear mixer or compulsory mixer.

The resultant mixture is preferably directly shaped into the dosage form according to the invention by application of force with preceding and/or simultaneous exposure to heat. The mixture may, for example, be formed into tablets by direct tabletting. In direct tabletting with preceding exposure to heat, the material to be pressed is heated immediately prior to tabletting at least to the softening temperature of component (C) and then pressed. In the case of direct tabletting with simultaneous application of heat, the mixture to be press-formed is heated at least to the softening point of polymeric component (C) with the assistance of the tabletting tool, i.e. the bottom punch, top punch and the die, and is so press-formed.

By such process using a tabletting tool with bottom punch, top punch and die for tablets having a diameter of 10 mm and a radius of curvature of 8 mm, e.g. 300 mg of a powder mixture may be compressed at a temperature of e.g. 80° C., the pressure caused by a force of e.g. 2 kN or 4 kN being maintained for e.g. 15 seconds.

The resultant mixture of components (A), (C), optionally (B) and optionally component (D) may also first be granulated and then, with preceding and/or simultaneous exposure to heat, be shaped into the dosage form according to the invention by application of force.

When force is applied, it is applied until the dosage form has achieved a resistance to crushing of at least 400 N, 420 N, 440 N, 460 N, 480 N, or preferably of at least 500 N.

Granulation may be performed in known granulators by wet granulation or melt granulation.

Each of the above-mentioned process steps, in particular the heating steps and simultaneous or subsequent application of force for production of the dosage form according to the invention proceeds without using an extruder.

Process Embodiment 2

In this process variant, the dosage form according to the invention is produced by thermoforming with the assistance of an extruder, without there being any observable consequent discoloration of the extrudate.

In order to investigate the extent of discoloration due to this thermoforming, the color of the mixture of starting components of which the dosage form consists is first determined without addition of a color-imparting component, such as for example a coloring pigment or an intrinsically coloured component (for example α-tocopherol). This composition is then thermoformed according to the invention, wherein all process steps, including cooling of the extrudate, are performed under an inert gas atmosphere. By way of comparison, the same composition is produced by the same process, but without an inert gas atmosphere. The color of the dosage form produced according to the invention from the starting composition and of the dosage form produced by way of comparison is determined. The determination is performed with the assistance of "Munsell Book of Color" from Munsell Color Company Baltimore, Md., USA, 1966 edition. If the colour of the dosage form thermoformed according to the invention has a color with identification no. N 9.5, but at most a color with the identification no. 5Y 9/1, thermoforming is classed as being "without discoloration". If the dosage form has a color with the identification no. 5Y 9/2 or greater, as determined according to the Munsell Book of Color, the thermoforming is classed as being "with discoloration".

Surprisingly, the dosage forms according to the invention exhibit no discoloration classed in accordance with the above classification, if the entire production process is performed under an inert gas atmosphere, preferably under a nitrogen atmosphere with the assistance of an extruder for thermoforming.

This variant according to the invention for the production of dosage forms according to the invention is characterised in that z) components (A), (C), optionally (B) and the optionally present component (D) are mixed, y) the resultant mixture is heated in the extruder at least up to the softening point of component (C) and extruded through the outlet orifice of the extruder by application of force, x) the still plastic extrudate is singulated and formed into the dosage form or w) the cooled and optionally reheated singulated extrudate is formed into the dosage form, wherein process steps y) and x) and optionally process steps z) and w) are performed under an inert gas atmosphere, preferably a nitrogen atmosphere.

Mixing of the components according to process step z) may also proceed in the extruder.

Components (A), (C), optionally (B) and optionally (D) may also be mixed in a mixer known to the person skilled in the art. The mixer may, for example, be a roll mixer, shaking mixer, shear mixer or compulsory mixer.

Before blending with the remaining components, component (C) and the optionally present component (D) is preferably provided according to the invention with an antioxidant. This may proceed by mixing the two components, (C) and the antioxidant, preferably by dissolving or suspending the antioxidant in a highly volatile solvent and homogeneously mixing this solution or suspension with component (C) and the optionally present component (D) and removing the solvent by drying, preferably under an inert gas atmosphere.

The, preferably molten, mixture which has been heated in the extruder at least up to the softening point of component (C) is extruded from the extruder through a die with at least one bore.

The process according to the invention requires the use of suitable extruders, preferably screw extruders. Screw extruders which are equipped with two screws (twin-screw-extruders) are particularly preferred.

The extrusion is preferably performed so that the expansion of the strand due to extrusion is not more than 50%, i.e. that when using a die with a bore having a diameter of e.g. 6 mm, the extruded strand should have a diameter of not more than 9 mm. More preferably, the expansion of the strand is not more than 40%, still more preferably not more than 35%, most preferably not more than 30% and in particular not more than 25%. It has been surprisingly found that if the extruded material in the extruder is exposed to a mechanical stress exceeding a certain limit, a significant expansion of the strand occurs thereby resulting in undesirable irregularities of the properties of the extruded strand, particularly its mechanical properties.

The extruder preferably comprises at least two temperature zones, with heating of the mixture at least up to the softening point of component (C) proceeding in the first zone, which is downstream from a feed zone and optionally mixing zone. The throughput of the mixture is preferably from 2.0 kg to 8.0 kg/hour.

After heating at least up to the softening point of component (C), the molten mixture is conveyed with the assistance of the screws, further homogenised, compressed or compacted such that, immediately before emerging from the extruder die, it exhibits a minimum pressure of 5 bar, preferably of at least 10 bar, and is extruded through the die as an extruded strand or strands, depending on the number of bores which the die comprises. The die geometry or the geometry of the bores is freely selectable. The die or the bores may accordingly exhibit a round, oblong or oval cross-section, wherein the round cross-section preferably has a diameter of 0.1 mm to 15 mm and the oblong cross-section preferably has a maximum lengthwise extension of 21 mm and a crosswise extension of 10 mm. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of component (C) and does not rise above a temperature at which the physiologically active substance (A) to be processed may be damaged. Preferably, the temperature of the mixture to be extruded is adjusted to below 180° C., preferably below 150° C., but at least to the softening temperature of component (C).

After extrusion of the molten mixture and optional cooling of the extruded strand or extruded strands, the extrudates are preferably singulated. This singulation may preferably be performed by cutting up the extrudates by means of revolving or rotating knives, water jet cutters, wires, blades or with the assistance of laser cutters.

An inert gas atmosphere is not necessary for intermediate or final storage of the optionally singulated extrudate or the final shape of the dosage form according to the invention.

The singulated extrudate may be pelletised with conventional methods or be press-formed into tablets in order to impart the final shape to the dosage form. It is, however, also possible not to singulate the extruded strands and, with the assistance of contrarotating calender rolls comprising opposing recesses in their outer sleeve, to form them into the final shape, preferably a tablet, and to singulate these by conventional methods.

Should the optionally singulated extrudate not immediately be formed into the final shape, but instead cooled for storage, after the period of storage an inert gas atmosphere, preferably a nitrogen atmosphere, should be provided and must be maintained during heating of the stored extrudate up until plasticisation and definitive shaping to yield the dosage form.

The application of force in the extruder onto the at least plasticised mixture is adjusted by controlling the rotational speed of the conveying device in the extruder and the geometry thereof and by dimensioning the outlet orifice in such a manner that the pressure necessary for extruding the plasticised mixture is built up in the extruder, preferably immediately prior to extrusion. The extrusion parameters which, for each particular composition, are necessary to give rise to a dosage form with a resistance to crushing of at least 400 N, preferably of at least 500 N, may be established by simple preliminary testing.

For example, extrusion may be performed by means of a twin-screw-extruder type Micro 27 GL 40 D (Leistritz, Nürnberg, Germany), screw diameter 18 mm. Screws having eccentric ends may be used. A heatable die with a round bore having a diameter of 8 mm may be used. The entire extrusion process should be performed under nitrogen atmosphere. The extrusion parameters may be adjusted e.g. to the following values: rotational speed of the screws: 100 Upm; delivery rate: 4 kg/h; product temperature: 125° C.; and jacket temperature: 120° C.

Process Embodiment 3

In this process variant for the production of the dosage form according to the invention energy is applied to a mixture of the components by means of ultrasonication.

First of all a homogeneous mixture of at least component (A) and component (C) (=binder) is produced. Further auxiliary substances, such as for example fillers, plasticisers, slip agents or dyes, may also be incorporated into this mixture. A low molecular weight polyethylene glycol is preferably used as plasticiser.

Mixing may be performed with the assistance of conventional mixers. Examples of suitable mixers are roll mixers, which are also known as tumbler, drum or rotary mixers, container mixers, barrel mixers (drum hoop mixers or tumbling mixers) or shaking mixers, shear mixers, compulsory mixers, plough bar mixers, planetary kneader-mixers, Z kneaders, sigma kneaders, fluid mixers or high-intensity mixers.

Selection of the suitable mixer is determined inter alia by the flowability and cohesiveness of the material to be mixed.

The mixture is then subjected to shaping. The mixture is preferably shaped during or after ultrasonication, preferably by compaction.

It is particularly preferred during ultrasonication that there is direct contact between the mixture and the sonotrode of the ultrasound device. An ultrasound device as shown in FIG. 1 is preferably used in the process according to the invention.

In this FIG. 1, (1) denotes the press, with which the necessary force is applied, (2) the converter, (3) the booster, (4) the sonotrode, (5) the shaping die, (6) the bottom punch, (7) the base plate, (8) and (9) the ultrasound generator and device controller. The reference numerals used relate solely to FIG. 1.

A frequency of 1 kHz to 2 MHz, preferably of 15 to 40 kHz, should be maintained during ultrasonication. Ultrasonication should be performed until softening of the polymer (C) is achieved. This is preferably achieved within a few seconds, particularly preferably within 0.1 to 5 seconds, preferably 0.5 to 3 seconds.

Ultrasonication and the application of force ensure uniform energy transfer, so bringing about rapid and homogeneous sintering of the mixture. In this manner, dosage forms are obtained which have a resistance to crushing of at least 400 N, preferably of at least 500 N, and thus cannot be pulverised.

Before shaping is performed, the mixture may be granulated after the mixing operation, after which the resultant granules are shaped into the dosage form with ultrasonication and application of force.

Granulation may be performed in machinery and apparatus known to the person skilled in the art.

If granulation is performed as wet granulation, water or aqueous solutions, such as for example ethanol/water or isopropanol/water, may be used as the granulation liquid.

The mixture or the granules produced therefrom may also be subjected to melt extrusion for further shaping, wherein the mixture is converted into a melt by ultrasonication and exposure to force and then extruded through a dies. The strands or strand obtained in this manner may be singulated to the desired length using known apparatus. The formed articles singulated in this manner may optionally furthermore be converted into the final shape with ultrasonication and application of force.

Final shaping to yield the dosage form preferably proceeds with application of force in appropriate moulds.

The above-described formed articles may also be produced with a calendering process by initially plasticising the mixture or the granules produced therefrom by means of ultrasonication and application of force and performing extrusion through an appropriate die. These extrudates are then shaped into the final shape between two contrarotating shaping rolls, preferably with application of force.

As already mentioned, shaping to yield the final shape of the dosage form by using a mixture comprising substance (A) and the polymer (C) with a resistance to crushing of at least 400 N, preferably of at least 500 N, proceeds preferably in powder form by direct compression with application of force, wherein ultrasonication of this mixture is provided before or during the application of force. The force is at most the force which is conventionally used for shaping dosage forms, such as tablets, or for press-forming granules into the corresponding final shape.

The tablets produced according to the invention may also be multilayer tablets.

In multilayer tablets, at least the layer which contains substance (A) should be ultrasonicated and exposed to force.

The corresponding necessary application of force may also be applied to the mixture with the assistance of extruder rolls or calender rolls. Shaping of the dosage forms preferably proceeds by direct press-forming of a pulverulent mixture of the components of the dosage form or corresponding granules formed therefrom, wherein ultrasonication preferably proceeds during or before shaping. Such exposure continues until the polymer (C) has softened, which is conventionally achieved in less than 1 second to at most 5 seconds.

A suitable press is e.g. a Branson WPS, 94-003-A, pneumatical (Branson Ultraschall, Dietzenbach, Germany) having a plain press surface. A suitable generator (2000 W) is e.g. a Branson PG-220A, 94-001-A analogue (Branson Ultraschall) with a sonotrode having a diameter of 12 mm. A die having a diameter of 12 mm may be used, the bottom of the die being formed by a bottom punch having a plain press-surface and a diameter of 12 mm. Suitable parameters for plastification are frequency: 20 kHz; amplitude: 50%; force: 250 N. The effect of ultrasound and force by means of the sonotrode may be maintained for e.g. 0.5 seconds, and preferably both effects take place simultaneously.

Process Embodiment 4

In this process variant for the production of the dosage form according to the invention, components (A), (C), optionally present auxiliary substances (B), such as antioxidants, plasticisers and/or delayed-release auxiliary substances, and optionally component (D), are processed with the assistance of a planetary-gear extruder to yield the dosage form according to the invention.

Planetary-gear extruders are known and described inter alia in detail in Handbuch der Kunststoff-Extrusionstechnik I (1989) "Grundlagen" in Chapter 1.2 "Klassifizierung von Extrudern", pages 4 to 6. The corresponding description is hereby introduced as a reference and is deemed to be part of the disclosure.

Below, the use of a planetary-gear extruder in the process according to the invention is explained with reference to FIGS. 2 and 3. These explanations are given merely by way of example and do not restrict the general concept of the invention.

Figure 2:
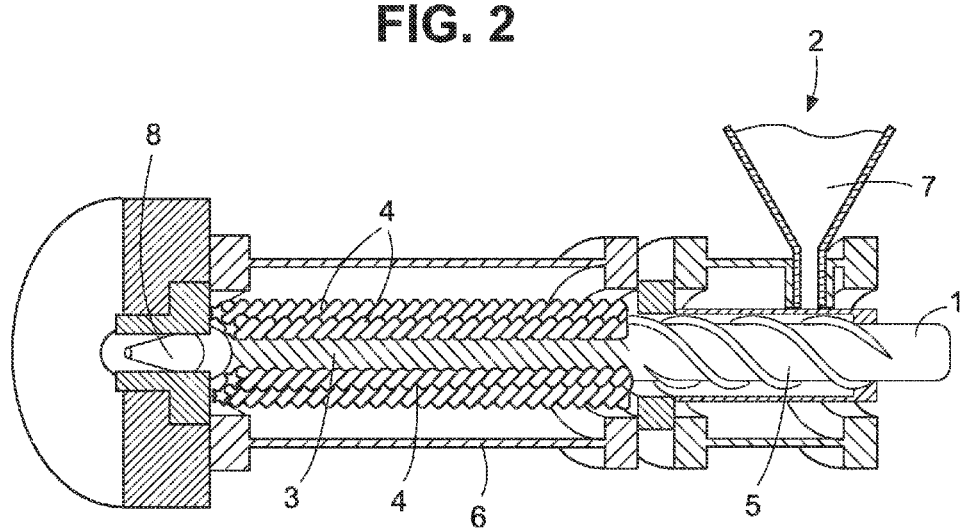
FIG. 2 shows a section through a planetary gear extruder.

FIG. 2 shows a section through a planetary-gear extruder and

Figure 3:
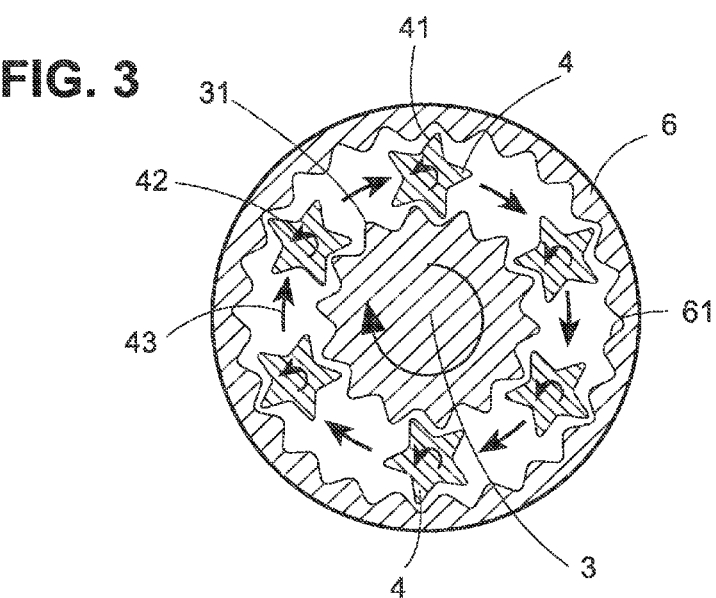
FIG. 3 shows the mode of operation of the planetary gear extruder.

FIG. 3 shows the mode of operation of the planetary-gear extruder.

FIG. 2 shows a planetary-gear extruder which may be used in the process according to the invention. This extruder substantially comprises a shaft 1, which, relative to the transport direction of the mixture of the components listed above to be extruded, is initially constructed as a feed screw 5 and subsequently as the central spindle 3 of the planetary-gear extruder. Around the central spindle 3 there are preferably arranged three to seven planetary spindles 4, which are in turn surrounded by a casing in the form of a housing 6.

In the planetary-gear extruder, extrusion of the composition used in the process according to the invention for the production of a pharmaceutical dosage form preferably proceeds as follows, with reference to FIG. 2. As shown by arrow 2, the components to be extruded are apportioned by the apportioning unit 7 in the area of the feed screw 5 and conveyed by the rotation thereof (drive not shown) in the direction of the central spindle 3. The person skilled in the art will understand that it is possible to mix the starting materials (components) in the area of the feed screw. However, it is also possible to premix the components of the dosage form and to apportion this mixture via the apportioning unit 7 in the area of the feed screw 5. The mixture is conveyed into the feed zone of the planetary-gear extruder. By heating at least to the softening point of component (C), the mixture is melted and the molten mixture is conveyed into the area of the central spindle, i.e. the extrusion zone, by the interaction of the central spindle 3 and the planetary spindles 4, further homogenised, compressed or compacted and extruded through the die 8 as an extruded strand or extruded strands, depending on how many bores the die comprises. The die geometry or the geometry of the bores is freely selectable. Thus, the die or the bores may exhibit a round, oblong or oval cross-section, wherein the round cross-section preferably has a diameter of 0.1 mm to 15 mm and the oblong cross-section preferably has a maximum lengthwise extension of 21 mm and a crosswise extension of 10 mm. The extrusion die may also take the form of a slot die. Preferably, the die or the bores have a round, oval or oblong cross-section. Both the casing 6 of the planetary-gear extruder used according to the invention and the central spindle may be heated or cooled. The corresponding temperature control, i.e. heating or cooling, is so arranged that the mixture to be extruded exhibits an average temperature corresponding to the softening temperature of component (C) and does not rise above a temperature at which the substance (A) to be processed may be damaged. Preferably, the temperature of the mixture to be extruded is adjusted to below 180° C., preferably below 150° C., but at least to the softening temperature of component (C). The reference numerals used relate solely to FIGS. 2 and 3.

After extrusion of the molten mixture and optional cooling of the extruded strand or extruded strands, the extrudates are singulated (not shown in FIG. 2). This singulation may preferably be performed by cutting up the extrudates by means of revolving or rotating knives, water jet cutters, wires, blades or with the assistance of laser cutters.

Optionally after further cooling of the singulated extrudates, which are preferably present in the form of disks, they are optionally re-shaped into the final shape of the dosage form, wherein they may be exposed to heat again if necessary.

This shaping for example into tablets may proceed in that the plastic extrudate is shaped with press-forming with the assistance of two contrarotating rolls preferably with mutually opposing recesses for plastification in the roll sleeve, the construction of which recesses determines the tablet shape.

However, it is also possible to form the tablets from the singulated extrudates in each case with the assistance of an optionally heated die and at least one shaping punch. To this end, the cylindrical granules obtained after singulation of the extruded strand may preferably be used. Apart from being press-formed into tablets, these granules or other multiparticulate shapes obtained, such as pellets or spheroids, may also be packaged into capsules in order to be used as a dosage form produced according to the invention.

In a further preferred embodiment, the extruded strands extruded through a plurality of bores in the extrusion die may, after cooling thereof, optionally be brought together by interlacing or wrapping in the manner of rope production to yield a thicker strand than the individual extruded strands. This strand may optionally be further processed by solvent attack with a suitable solvent or by heating to the softening point of the polymer (C) and optionally removing the solvent in accordance with the above-stated singulation and shaping of an individual strand.

FIG. 3 shows a cross-section through the planetary-gear extruder. Around the rotating central spindle 3 there are arranged at least three, in the case illustrated 6, planetary spindles 4, whose flanks 41 interact on the one hand with the flank 31 of the central spindle 4 and on the other hand with the flanks 61 of the casing 6 of the planetary-gear extruder. Through rotation of the central spindle 3 and rolling of the respective flanks over one another, the planetary spindles 4 each rotate around their own axis, as shown by arrow 42, and around the central spindle 4, as shown by arrow 43. In this way, the compression or compaction sought according to the invention of the component mixture used according to the invention of the dosage forms produced according to the invention is achieved. The reference numerals used relate solely to FIGS. 2 and 3.

If necessary, the planetary-gear extruder used may comprise not only an extrusion zone but also at least one further zone, so that the mixture to be extruded may optionally also be degassed.

The process according to the invention may be performed discontinuously or continuously, preferably continuously.

A suitable extruder, for example, is a planetary gear extruder type BCG 10 (LBB Bohle, Ennigerloh, Germany) having four planetary spindles and an extrusion die with bores having a diameter of 8 mm. A gravimetrical dosing of 3.0 kg/h is suitable. The extrusion may be performed, for example, at a rotational speed of 28.6 rmp and a product temperature of about 88° C.

Process Embodiment 5

This variant for the production of the dosage form according to the invention is performed by processing at least the components (A), (C), optionally present auxiliary substances (B), such as antioxidants, plasticisers and/or delayed-release auxiliary substances, and optionally component (D), with addition of a solvent for component (C), i.e. for the polymer or polymers (C), to yield the dosage form.

To this end, components (A), (C), optionally (B) and the optionally present component (D) are mixed and, after addition of the solvent and optionally after granulation, the resultant formulation mixture is shaped to yield the dosage form.

Components (A), (C), optionally (B) and optionally (D) are mixed in a mixer known to the person skilled in the art. The mixer may, for example, be a roll mixer, shaking mixer, shear mixer or compulsory mixer.

The solvent for the polymer (C) is added at least in such quantities that the formulation mixture is uniformly moistened.

Solvents which are suitable for the polymer (C) are preferably aqueous solvents, such as water, mixtures of water and aliphatic alcohols, preferably C1 to C6 alcohols, esters, ethers, hydrocarbons, particularly preferably distilled water, short-chain alcohols, such as methanol, ethanol, isopropanol, butanol or aqueous alcohol solutions.

The solvent is preferably added with stirring. The uniformly moistened composition is then dried. Drying preferably proceeds with exposure to heat at temperatures at which it is possible to rule out any discoloration of the composition. This temperature may be established by simple preliminary testing.

Before or after drying, the composition may be divided into sub-portions which preferably in each case correspond to the mass of a unit of the dosage form. The corresponding dried portions are then shaped to yield the dosage form.

This is preferably achieved by using tablet presses.

The formulation mixture may also be moistened in such a manner that, before addition of the solvent, the formulation mixture is divided, preferably in moulds, into sub-portions, is dispersed in a liquid dispersant with stirring and then the solvent is added. Component (C) is not soluble in the dispersant, which must be miscible with the solvent.

Suitable dispersants are preferably hydrophilic solvents, such as aliphatic alcohols, ketones, esters. Short-chain alcohols are preferably used.

Alternatively, the formulation mixture may also be moistened in such a manner that the solvent is incorporated into the formulation mixture as a foam. Such a foam of the solvent is preferably produced with the assistance of a high-speed mixer, preferably with the addition of conventional foam stabilisers. Suitable stabilisers are, for example, hydrophilic polymers such as for example hydroxypropylmethylcellulose.

The foam is also preferably incorporated into the formulation mixture with stirring, a granulated composition so preferably being obtained.

Before or after being divided into sub-portions, which preferably correspond to the mass of a unit of the dosage form, the granulated composition is dried and then shaped into the dosage form.

Drying and shaping may preferably proceed as described above. The process according to the invention may also be performed in such a manner that solvent is added to the formulation mixture in such a quantity that a shapeable paste is obtained.

Before or after being dried, which may proceed as explained above, such a paste may be divided into sub-portions and the dried portions, after further division in each case into a portion corresponding to the mass of a unit of the dosage form, are shaped or converted to yield the dosage form.

It is here possible to form the sub-portions in the form of strands, which may be produced with the assistance of a screen or a strand former. The dried strands are preferably singulated and shaped to yield the dosage form. This shaping preferably proceeds with the assistance of a tablet press, using shaping rollers or shaping belts equipped with rollers.

It is also possible to convert the paste into a planar structure and to stamp the dosage form out of it once it has dried.

The paste is advantageously processed with an extruder, wherein, depending on the configuration of the extrusion, strands or planar structures articles are produced, which are singulated by chopping, cutting or stamping. The singulated sub-portions may be shaped, formed or stamped as described above to yield the dosage form. Corresponding apparatuses are known to the person skilled in the art.

The process according to the invention may here be performed continuously or discontinuously.

It is also possible to add solvent to the formulation mixture in such a quantity that at least the polymer component (C) is dissolved. Such a solution or dispersion/suspension is preferably converted into a planar structure, an extruder with a flat die preferably being used or the solution being cast onto a planar support.

As stated above, after drying, the dosage forms may be obtained from the planar structures by stamping or calendering. It is also possible, as stated above, to convert the solution into strands and to singulate these, preferably after they have been dried, and shape them to yield the dosage form.

Alternatively, the solution may also be divided into portions such that, after drying, they each correspond to the mass of a unit of the dosage form, with moulds which already correspond to the shape of the unit of the dosage form preferably being used for this purpose.

If the solution is divided into any desired portions, the portions may, after drying, optionally be combined again and be shaped to form the dosage form, being for example packaged in a capsule or press-formed to form a tablet.

The formulation mixtures combined with solvent are preferably processed at temperatures of 20° C. to 40° C., wherein, apart from during drying to remove the solvent and the optionally present dispersant, no higher temperatures are used. The drying temperature must be selected below the decomposition temperature of the components. After shaping to yield the dosage form, further drying corresponding to the above-described drying may optionally be performed.

Combinations of individual process steps of the above process variants are also possible in order to produce the dosage form according to the invention.

Process variants 2 and 4 as described above involve the extrusion of a composition comprising components (A), (C), optionally (B) and optionally (D). Preferably, extrusion is performed by means of twin-screw-extruders or planetary-gear-extruders, twin-screw extruders being particularly preferred.

Morphology

It has been surprisingly found that extrudates exhibiting an advantageous morphology are obtainable by means of planetary-gear-extruders and twin-screw-extruders. It has been found that under suitable conditions the extrudate is surrounded by a shell which may be denoted as "extrusion skin". Said extrusion skin can be regarded as a collar-like or tubular structure forming a circumferential section of the extrudate about its longitudinal extrusion axis so that the outer surface of said collar-like or tubular structure forms the closed shell of the extrudate. Usually, only the front faces of the extrudate are not covered by said extrusion skin.

The extrusion skin surrounds the core of the extrudate in a collar-like or tubular arrangement and preferably is connected therewith in a seamless manner. The extrusion skin differs from said core in its morphology. Usually, the extrusion skin is visible with the naked eye in the cross-section of the extrudate, optionally by means of a microscope, since due to the different morphology of the material forming the extrusion skin and the material forming the core, the optical properties differ as well. It seems that during extrusion the material forming the extrusion skin is exposed to mechanical and thermal conditions differing from the conditions the core of the extrudate is exposed to. In consequence, a heterogeneous morphology of the extruded strand is obtained, which e.g. assumes radial symmetry when an extrusion die having circular shape is used. The material forming the extrusion skin and the material forming the core are usually distinguished by their morphology, preferably, however, not by their composition, particularly not by the relative content of components (A), (C), optionally (B) and optionally (D).

Usually the extrusion skin covers the entire shell of the extrudate like a one-piece collar, independently of what geometry has been chosen for the extrusion die. Therefore, the extrudate may assume circular, elliptic or other cross-sections.

The extrusion skin is preferably characterized by a unitary thickness. Preferably, the thickness of the extrusion skin is within the range from 0.1 to 4.0 mm, or, in increasing order of preference 0.15 to 3.5 mm, 0.2 to 3.0 mm, 0.2 to 2.5 mm or 0.2 to 2.0 mm. In a preferred embodiment the thickness of the extrusion skin in the sum over both opposing sides amounts to 0.5 to 50%, or in increasing order of preference 1.0 to 40%, 1.5 to 35%, 2.0 to 30% or 2.5 to 25% of the diameter of the extrudate.

Figure 4:
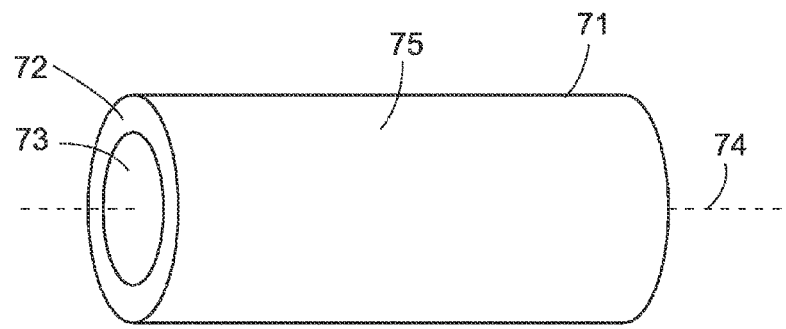
FIG. 4 shows a schematic view of the extrudate of the composition.

FIG. 4 shows a schematic view of extrudate (71) having a collar-like extrusion skin (72) entirely surrounding the core (73) about the longitudinal extrusion axis (74). The outer surface of extrusion skin (72) forms the shell (75) of the extrudate (71).

It has been surprisingly found that extrudates having an extrusion skin exhibit beneficial mechanical properties. They are particularly suitable as intermediates in the production of the dosage forms according to the invention, because they may be advantageously processed, in particular by singulating and/or forming.

When the dosage forms according to the invention are prepared by means of extrusion processes which lead to intermediates having an extrusion skin as described above, the dosage forms obtained therefrom are preferably also characterized by a particular morphology.

In a preferred embodiment those regions, which have formed the extrusion skin in the extruded intermediate, are still visible with the naked eye, optionally by means of a microscope, in the cross-section of the dosage form. This is because usually by further processing the extrudate, particularly by singulating and/or shaping, the different nature and thereby also the different optical properties of the material forming the extrusion skin and the material forming the core are maintained. In the following, that domain of the dosage forms which has emerged from the extrusion skin in the course of further processing the extruded intermediate, will be denoted as "tubular domain".

Preferably, the dosage form according to the invention comprises a tubular domain and a core located therein. Preferably, the tubular domain is connected with the core in a seamless manner. Preferably the tubular domain as well as the core have substantially the same chemical composition, i.e. substantially the same relative content of components (A), (C), optionally (B) and optionally (D). The material forming the tubular domain has a morphology differing from the material forming the core. Usually, this different morphology is also expressed in terms of different optical properties, so that the tubular domain and the core are visible with the naked eye in the cross-section of the dosage form.

In case that the dosage form has been coated, e.g. by a film coating, the tubular domain is located between the film coating and the core.

Since the dosage form according to the invention may be obtained in different ways from the extrudate containing the extrusion skin (intermediate), the tubular domain may take different arrangements and extensions within the dosage form according to the invention. All arrangements have in common, however, that the tubular domain partially covers the surface of the core, but usually not its entire surface. Preferably, two opposing surfaces of the core are not, or at least not fully covered by the tubular domain. In other words, preferably the tubular domain has two openings/blanks on opposing sides.

The thickness of the tubular domain may be uniform. It is also possible, however, that in the course of the processing, i.e. due to the subsequent shaping (e.g. press-forming) of the extrudate, various sections of the extrusion skin are expanded or compressed differently thereby leading to a variation of the thickness of the tubular domain within the dosage form.

Preferably the thickness of the tubular domain is within the range from 0.1 to 4.0 mm, or in increasing order of preference 0.15 to 3.5 mm, 0.2 to 3.0 mm, 0.2 to 2.5 mm or 0.2 to 2.0 mm.

Figure 5A:
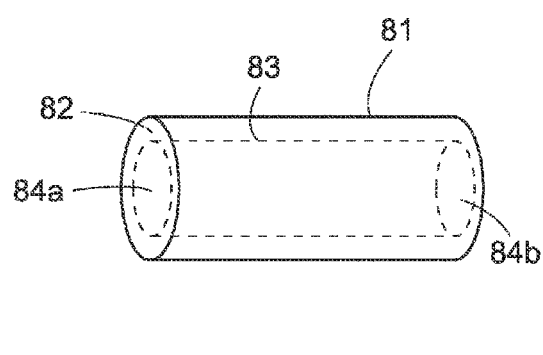
FIGS. 5A and 5B show schematic views of the preferred arrangements of the tubular domain within the dosage form.
Figure 5B:
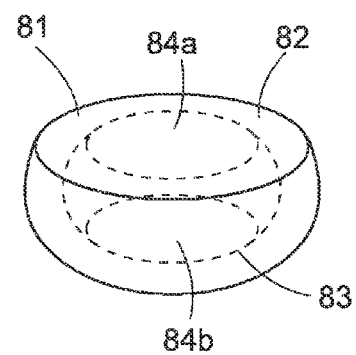

FIGS. 5A and 5B show schematic views of preferred arrangements of the tubular domain within the dosage form according to the invention. The dosage forms (81) contain a tubular domain (82) partially surrounding the core (83). The opposing surfaces (84a) and (84b) of the core (83), however, are not covered by the tubular domain (82).

The process for the preparation of the dosage form according to the invention is preferably performed continuously. Preferably, the process involves the extrusion of a homogeneous mixture of components (A), (C), optionally (B) and optionally (D). It is particularly advantageous if the obtained intermediate, e.g. the strand obtained by extrusion, exhibits uniform properties. Particularly desirable are uniform density, uniform distribution of the active substance, uniform mechanical properties, uniform porosity, uniform appearance of the surface, etc. Only under these circumstances the uniformity of the pharmacological properties, such as the stability of the release profile, may be ensured and the amount of rejects can be kept low.

Preferably, the process according to the present invention may be performed with less than 25% rejects, more preferably less than 20%, most preferably less than 15% and in particular less than 10% rejects, wherein the criteria for rejection are the FDA standards regarding the intervariability of the content of component (A), its release profile and/or the density of the dosage form when comparing two dosage forms, preferably taken from the same batch.

It has been surprisingly found that the above properties may be obtained by means of twin-screw-extruders and planetary-gear-extruders, twin-screw-extruders being particularly preferred.

The process according to the invention preferably involves the extrusion of a mixture of components (A), (C), optionally (B) and optionally (D), preferably by means of a planetary-gear-extruder or a twin-screw-extruder. After extrusion the extrudate is preferably singulated, shaped and optionally coated in order to obtain the final dosage form.

In a preferred embodiment of the process according to the invention, shaping is performed in the plasticized state of the mixture of components (A), (C), optionally (B) and optionally (D). It has been surprisingly found that the extrusion of certain polymers (C), particular of high molecular weight polyethylene oxides, yields intermediates exhibiting some kind of memory effect: when the singulated extrudates are shaped at ambient temperature, e.g. by press-forming, dosage forms are obtained which tend to regain their original outer form upon storage under stressed storage conditions, i.e. they return to the form they had prior to shaping.

The shape of the dosage form upon storage at stressed conditions, e.g. at 40° C. and 75% RH, may also be unstable for other reasons.

The memory effect significantly deteriorates the storage stability of the dosage form, as by regaining its outer form several properties of the dosage form are changed. The same applies to any changes of the outer form due to other reasons.

It has been found that, for example, depending on the extrusion conditions a significant expansion of the strand may occur thereby resulting in an increase of the volume of the extrudate, i.e. a decrease of its density. Such expansion may be compensated by subsequently press-forming the singulated extrudate at a sufficient pressure, since under these conditions the expansion of the material may be reversed.

However, if press-forming has been performed at ambient temperature, the memory effect of the compressed extrudate will cause it to swell and to expand upon storage, thereby significantly increasing the volume of the dosage form.

It has been surprisingly found that such memory effect may be suppressed if shaping of the singulated extrudate is performed at increased temperature, i.e. in the plasticized state of the mixture of components (A), (C), optionally (B) and optionally (D). Preferably, shaping is performed at a pressure of at least 1 kN, more preferably within the range from 2 kN to 50 kN, e.g. by means of a tablet press. Preferably, shaping is performed at a temperature which preferably is about 40° C., more preferably about 30° C. and in particular about 25° C. below the melting range of the mixture of components (A), (C), optionally (B) and optionally (D). The melting range of a given mixture may be determined by conventional methods, preferably by DSC (e.g. with a DSC model 2920 (TA Instruments, New Castle) and ultrahigh pure nitrogen as purge gas at a flow rate of 150 ml/min; approximate sample weight of 10-20 mg, sealed in nonhermetic aluminium pans; temperature ramp speed 10° C./min).

In a preferred embodiment the outer shape of the dosage form according to the invention does not substantially change when being stored for at least 12 h, preferably for at least 24 h, at 40° C. and 75% RH, preferably in an open container.

In a preferred embodiment the volume of the dosage form according to the invention increases by not more than 20% or 17.5%, more preferably not more than 15% or 12.5%, still more preferably not more than 10% or 7.5%, most preferably not more than 6.0%, 5.0% or 4.0% and in particular not more than 3.0%, 2.0% or 1.0% when being stored for at least 12 h, preferably for at least 24 h, at a temperature of 20° C. below the melting range of the mixture of components (A), (C), optionally (B) and optionally (D), optionally at a temperature of 40° C. and 75% RH.

The dosage form according to the invention exhibits controlled release of the active ingredient. It is preferably suitable for twice daily administration to patients.

The dosage form according to the invention may comprise one or more substances (A) at least in part in a further delayed-release form, wherein delayed release may be achieved with the assistance of conventional materials and processes known to the person skilled in the art, for example by embedding the substance in a delayed-release matrix or by applying one or more delayed-release coatings. Substance release must, however, be controlled such that addition of delayed-release materials does not impair the necessary hardness.

Controlled release from the dosage form according to the invention is preferably achieved by embedding the substance in a matrix. The auxiliary substances acting as matrix materials control release. Matrix materials may, for example, be hydrophilic, gel-forming materials, from which release proceeds mainly by diffusion, or hydrophobic materials, from which release proceeds mainly by diffusion from the pores in the matrix.

Physiologically acceptable, hydrophobic materials which are known to the person skilled in the art may be used as matrix materials. Polymers, particularly preferably cellulose ethers, cellulose esters and/or acrylic resins are preferably used as hydrophilic matrix materials. Ethylcellulose, hydroxypropylmethylcellulose, hydroxypropylcellulose, hydroxymethylcellulose, poly(meth)acrylic acid and/or the derivatives thereof, such as the salts, amides or esters thereof are very particularly preferably used as matrix materials.

Matrix materials prepared from hydrophobic materials, such as hydrophobic polymers, waxes, fats, long-chain fatty acids, fatty alcohols or corresponding esters or ethers or mixtures thereof are also preferred. Mono- or diglycerides of C12-C30 fatty acids and/or C12-C30 fatty alcohols and/or waxes or mixtures thereof are particularly preferably used as hydrophobic materials.

It is also possible to use mixtures of the above-stated hydrophilic and hydrophobic materials as matrix materials.

Component (C) and the optionally present component (D), which serve to achieve the resistance to crushing of at least 400 N which is necessary according to the invention, may furthermore themselves serve as additional matrix materials.

If the dosage form according to the invention is intended for oral administration, it may also preferably comprise a coating which is resistant to gastric juices and dissolves as a function of the pH value of the release environment. By means of this coating, it is possible to ensure that the dosage form according to the invention passes through the stomach undissolved and the active ingredient is only released in the intestines. The coating which is resistant to gastric juices preferably dissolves at a pH value of between 5 and 7.5.

Corresponding materials and methods for the delayed release of active ingredients and for the application of coatings which are resistant to gastric juices are known to the person skilled in the art, for example from "Coated Pharmaceutical Dosage Forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers. The corresponding literature description is hereby introduced as a reference and is deemed to be part of the disclosure.

The invention also relates to the use of a physiologically active substance (A) as described above and/or a synthetic or natural polymer (C) as described above for the manufacture of the dosage form according to the invention for the prophylaxis and/or the treatment of a disorder, thereby preventing an overdose of the physiologically active substance (A), particularly due to comminution of the dosage form by mechanical action.

Further, the invention relates to a method for the prophylaxis and/or the treatment of a disorder comprising the administration of the dosage form according to the invention, thereby preventing an overdose of the physiologically active substance (A), particularly due to comminution of the dosage form by mechanical action.

Preferably, the mechanical action is selected from the group consisting of chewing, grinding in a mortar, pounding, and using apparatuses for pulverising conventional dosage forms.

The resistance to crushing of the dosage forms obtained according to the invention is determined by the stated measurement method, with dosage forms other than tablets also being tested.

The resistance to crushing of the dosage form according to the invention may be determined by producing dosage forms, preferably tablets, with a diameter of 10 mm and a height of 5 mm.

Using these dosage forms, preferably tablets, the resistance to crushing of the dosage form is determined in accordance with the method for determining the resistance to crushing of tablets, published in the European Pharmacopoeia 1997, page 143, 144, method no. 2.9.8. using the apparatus stated below. The apparatus used for the measurement is a "Zwick Z 2.5" materials tester, Fmax=2.5 kN with a maximum draw of 1150 mm, which should be set up with 1 column and 1 spindle, a clearance behind of 100 mm and a test speed adjustable between 0.1 and 800 mm/min together with testControl software. Measurement is performed using a pressure piston with screw-in inserts and a cylinder (diam. 10 mm), a force transducer, Fmax. 1 kN, diameter=8 mm, class 0.5 from 10 N, class 1 from 2 N to ISO 7500-1, with manufacturer's test certificate M to DIN 55350-18 (Zwick gross force Fmax=1.45 kN) (all apparatus from Zwick GmbH & Co. KG, Ulm, Germany) with order no. BTC-FR 2.5 TH. D09 for the tester, order no. BTC-LC 0050N. P01 for the force transducer, order no. BO 70000 S06 for the centring device.

Figure 6:
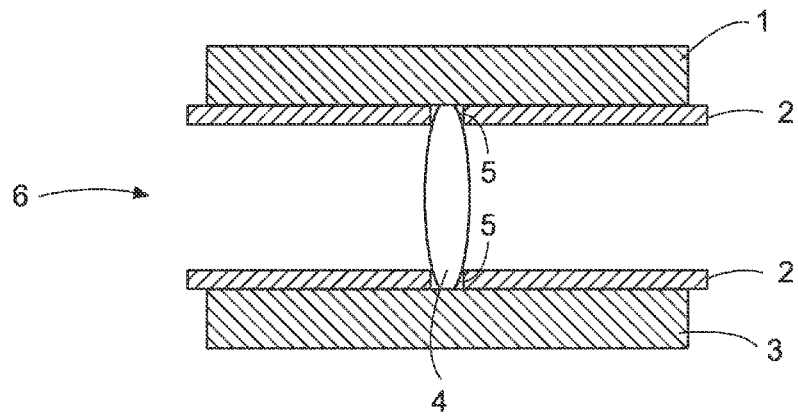
FIG. 6 shows the measurement of the crush resistance of a tablet.

FIG. 6 shows the measurement of the resistance to crushing of a tablet, in particular the tablet (4) adjustment device (6) used for this purpose before and during the measurement. To this end, the tablet (4) is held between the upper pressure plate (1) and the lower pressure plate (3) of the force application apparatus (not shown) with the assistance of two 2-part clamping devices, which are in each case firmly fastened (not shown) with the upper and lower pressure plate once the spacing (5) necessary for accommodating and centering the tablet to be measured has been established. The spacing (5) may be established by moving the 2-part clamping devices horizontally outwards or inwards in each case on the pressure plate on which they are mounted. The reference numerals used relate solely to FIG. 6.

Figure 7:
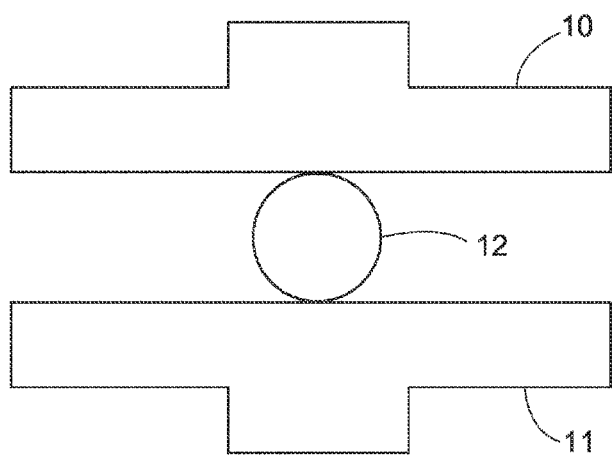
FIG. 7 shows a probe for measurement of the crush resistance.

In case that the dosage form according to the invention is in multiparticulate form, the resistance to crushing may be alternatively be determined by means of two pressure plates, such as depicted e.g. in FIG. 7.

FIG. 7 shows a probe (12), e.g. a pellet, which is placed between a top pressure plate (10) and a bottom pressure plate (11). Force is effected to the probe by means of the two pressure plates. The result of the measurement is analysed analogously to the method that has been described above in connection with FIG. 6.

The tablets deemed to be resistant to crushing under a specific load include not only those which have not broken but also those which may have suffered plastic deformation under the action of the force.

The invention is explained below with reference to Examples. These explanations are given merely by way of example and do not restrict the general concept of the invention.

In a first series of examples diltiazem hydrochloride, verapamil hydrochloride and carbamazepine were used as the active ingredients (substance (A)):

Example 1

| Components | per tablet | Complete batch |
| --- | --- | --- |
| diltiazem HCl | 90.0 mg | 720 mg |
| polyethylene oxide, NF, MW 7 000 000 | 154.2 mg | 1233.6 mg |
| (Polyox WSR 303, Dow Chemicals) total weight | 244.2 mg | 1.9536 g |

All the components were mixed in a free-fall mixer. A tabletting tool with top punch, bottom punch and die for tablets with a diameter of 10 mm and a radius of curvature (concavity) of 8 mm was heated to 80° C. in a heating cabinet. Portions of the powder mixture were pressed with the heated tool, wherein pressure was maintained for at least 15 seconds by clamping the tabletting tool in a vice.

The resistance to crushing of the tablets was determined with the stated apparatus in accordance with the stated method. The tablets did not crush when exposed to a force of 500 N. The tablet could not be comminuted with a hammer. This could not be achieved with the assistance of a pestle and mortar either.

In vitro release of the active ingredient from the preparation was determined in a paddle stirrer apparatus in accordance with Pharm. Eur. (paddle with sinker). The temperature of the release medium was 37° C. and the rotational speed of the stirrer 50 min. At the beginning of the investigation, each tablet was placed in a 900 ml portion of artificial gastric juice, pH 1.2. After 30 minutes, the pH value was increased to 2.3 by addition of alkali solution, after a further 90 minutes to pH 6.5 and after a further 60 minutes to pH 7.2. The quantity of active ingredient released in each case into the dissolution medium at any one time was determined by spectrophotometry at 236 nm in 2 mm measurement cells.

| time | released quantity |
| --- | --- |
| 30 min | 12% |
| 240 min | 43% |
| 480 min | 63% |
| 600 min | 71% |
| 720 min | 77% |

Example 2

In a manner similar to Example 1, oblong tablets having a width of 9 mm and a lengthwise extension of 20 mm were produced with the following composition:

| Components | per tablet | complete batch |
| --- | --- | --- |
| verapamil HCl | 240.0 mg | 1920 mg |
| polyethylene oxide, NF, MW 7 000 000 | 411.4 mg | 3291.2 mg |
| (Polyox WSR 303, Dow Chemicals) total weight | 651.4 mg | 4.2112 g |

The resistance to crushing of the tablets was determined with the stated apparatus in accordance with the stated method. The tablets did not crush when exposed to a force of 500 N.

In vitro release of the active ingredient was determined in a manner similar to Example 1 (UV detector at 279 nm) and was:

| Time | released quantity |
|---|---|
| 30 min | 6% |
| 240 min | 20% |
| 480 min | 30% |
| 600 min | 35% |
| 720 min | 39% |

Example 3

In a similar manner to Example 1, round tablets with a diameter of 20 mm and of the following composition were produced:

| Components | per tablet | complete batch |
|---|---|---|
| Carbamazepine | 600 mg | 4800 mg |
| polyethylene oxide, NF, MW 7 000 000 | 1028.5 mg | 8228.0 mg |
| (Polyox WSR 303, Dow Chemicals) | | |
| total weight | 1628.5 mg | 13.028 g |

The resistance to crushing of the tablets was determined with the stated apparatus in accordance with the stated method. The tablets did not crush when exposed to a force of 500 N.

In vitro release of the active ingredient was determined in a manner similar to Example 1 (UV detector at 285 nm) and was:

| time | released quantity |
|---|---|
| 30 min | 1% |
| 240 min | 5% |
| 480 min | 9% |
| 600 min | 11% |
| 720 min | 13% |

In a further series of examples nifedipine was used as the active ingredient (substance (A)):

Example 4

Tablets having the following composition were produced:

| components | per tablet | complete batch | content [%] |
|---|---|---|---|
| nifedipine | 20 mg | 2 g | 10 |
| polyethylene oxide 900 000 | 180 mg | 18 g | 90 |
| (Polyox WSR 1105 Dow Chemicals) | | | |

Nifedipine and polyethylene oxide were mixed in a free-fall mixer. The mixture was compressed on an excentric tablet press (model EK 0, Korsch) to circular tablets having a weight of 200 mg, a diameter of 8 mm and a radius of curvature of 8 mm. Then, the tabletting tool with top punch, bottom punch and die for tablets with a diameter of 10 mm and a radius of curvature of 8 mm was heated to 100° C. in a heating cabinet. Once again the tablets were compressed by means of the heated tool, wherein pressure was maintained for at least 15 seconds.

The resistance to crushing of the tablets was determined with the stated apparatus in accordance with the stated method. The tablets did not crush when exposed to a force of 500 N. The tablet could not be comminuted with a hammer. This could not be achieved with the assistance of a pestle and mortar either.

Example 5

Tablets having the following composition were produced as described in Example 4:

| Components | per tablet | complete batch | content [%] |
|---|---|---|---|
| Nifedipine | 20 mg | 2 g | 10 |
| polyethylene oxide 600 000 | 180 mg | 18 g | 90 |
| (Polyox WSR 205 Dow Chemicals) | | | |

The resistance to crushing of the tablets was determined with the stated apparatus in accordance with the stated method. The tablets did not crush when exposed to a force of 500 N. The tablet could not be comminuted with a hammer. This could not be achieved with the assistance of a pestle and mortar either.

Example 6

Tablets having the following composition were produced as described in Example 4:

| Components | per tablet | complete batch | content [%] |
|---|---|---|---|
| Nifedipine | 20 mg | 2 g | 10 |
| polyethylene oxide 5 000 000 | 180 mg | 18 g | 90 |
| (Polyox WSR Coagulant Dow Chemicals) | | | |

The resistance to crushing of the tablets was determined with the stated apparatus in accordance with the stated method. The tablets did not crush when exposed to a force of 500 N. The tablet could not be comminuted with a hammer. This could not be achieved with the assistance of a pestle and mortar either.

Example 7

Tablets having the following composition were produced as described in Example 4:

| Components | per tablet | complete batch | content [%] |
|---|---|---|---|
| Nifedipine | 20 mg | 2 g | 10 |
| polyethylene oxide 100 000 | 20 mg | 2 g | 10 |
| (Polyox WSR N 10 Dow Chemicals) | | | |
| polyethylene oxide 5 000 000 | 160 mg | 160 g | 80 |
| (Polyox WSR Coagulant Dow Chemicals) | | | |

The resistance to crushing of the tablets was determined with the stated apparatus in accordance with the stated method. The tablets did not crush when exposed to a force of 500 N. The tablet could not be comminuted with a hammer. This could not be achieved with the assistance of a pestle and mortar either.

In a further series of examples tramadol hydrochloride and oxycodone hydrochloride were used as active ingredients (substance (A)).

Example 8

| Components | per tablet | complete batch |
|---|---|---|
| tramadol HCl | 100 mg | 100 g |
| polyethylene oxide, NF, MFI (190° C. at 21.6 kg/10 min) <0.5 g MW 7 000 000 (Polyox WSR 303, Dow Chemicals) | 200 mg | 200 g |
| total weight | 300 mg | 300 g |

Tramadol hydrochloride and polyethylene oxide powder were mixed in a free-fall mixer. A tabletting tool with top punch, bottom punch and die for tablets with a diameter of 10 mm and a radius of curvature of 8 mm was heated to 80° C. in a heating cabinet. 300 mg portions of the powder mixture were pressed with the heated tool, wherein pressure was maintained for at least 15 seconds by clamping the tabletting tool in a vice.

The resistance to crushing of the tablets was determined with the stated apparatus in accordance with the stated method. The tablets did not break when exposed to a force of 500 N.

The tablet could not be comminuted using a hammer, nor with the assistance of a mortar and pestle.

In vitro release of the active ingredient from the preparation was determined in a paddle stirrer apparatus in accordance with Pharm. Eur. The temperature of the release medium was 37° C. and the rotational speed of the stirrer 75 min$^{-1}$. At the beginning of the investigation, each tablet was placed in a 600 ml portion of artificial gastric juice, pH 1.2. After 30 minutes, the pH value was increased to 2.3 by addition of alkali solution, after a further 90 minutes to pH 6.5 and after a further 60 minutes to pH 7.2. The released quantity of active ingredient present in the dissolution medium at each point in time was determined by spectrophotometry.

| time | released quantity |
|---|---|
| 30 min | 15% |
| 240 min | 52% |
| 480 min | 80% |
| 720 min | 99% |

Example 9

300 mg portions of the powder mixture from Example 8 were heated to 80° C. and in placed in the die of the tabletting tool. Pressing was then performed. The tablet exhibits the same properties such as the tablet in Example 8.

Example 10

| Components | per tablet | complete batch |
|---|---|---|
| tramadol HCl | 50 mg | 100 g |
| polyethylene oxide, NF, MW 7 000 000 (Polyox WSR 303, Dow Chemicals) | 100 mg | 200 g |
| total weight | 150 mg | 300 g |

Tramadol hydrochloride and the above-stated components were mixed in a free-fall mixer. A tabletting tool with top punch, bottom punch and die for tablets with a diameter of 7 mm was heated to 80° C. in a heating cabinet. 150 mg portions of the powder mixture were pressed with the heated tool, wherein pressure was maintained for at least 15 seconds by clamping the tabletting tool in a vice.

The resistance to crushing of the tablets was determined with the stated apparatus in accordance with the stated method. The tablets did not break when exposed to a force of 500 N.

In vitro release of the active ingredient was determined as in Example 8 and was:

| time | released quantity |
|---|---|
| 30 min | 15% |
| 240 min | 62% |
| 480 min | 88% |
| 720 min | 99% |

Example 11

| Components | per tablet | complete batch |
|---|---|---|
| tramadol HCl | 100 mg | 100 g |
| polyethylene oxide, NF, MW 7 000 000 (Polyox WSR 303, Dow Chemicals) | 180 mg | 180 g |
| Xanthan, NF | 20 mg | 20 g |
| total weight | 300 mg | 300 g |

Tramadol hydrochloride, xanthan and polyethylene oxide were mixed in a free-fall mixer. A tabletting tool with top punch, bottom punch and die for tablets with a diameter of 10 mm and a radius of curvature (concavity) of 8 mm was heated to 80° C. in a heating cabinet. 300 mg portions of the powder mixture were pressed with the heated tool, wherein pressure was maintained for at least 15 seconds by clamping the tabletting tool in a vice.

The resistance to crushing of the tablets was determined with the stated apparatus in accordance with the stated method. The tablets did not break when exposed to a force of 500 N. The tablets did suffer a little plastic deformation.

In vitro release of the active ingredient was determined as in Example 8 and was:

| time | released quantity |
|---|---|
| 30 min | 14% |
| 240 min | 54% |
| 480 min | 81% |
| 720 min | 99% |

Example 12

| Components | per tablet | complete batch |
| --- | --- | --- |
| tramadol HCl | 50 mg | 100 g |
| polyethylene oxide, NF, MW 7 000 000 (Polyox WSR 303, Dow Chemicals) | 90 mg | 180 g |
| Xanthan, NF | 10 mg | 20 g |
| total weight | 150 mg | 300 g |

Tramadol hydrochloride, xanthan and polyethylene oxide were mixed in a free-fall mixer. A tabletting tool with a top punch, bottom punch and die for oblong tablets 10 mm in length and 5 mm in width was heated to 90° C. in a heating cabinet. 150 mg portions of the powder mixture were pressed with the heated tool, wherein pressure was maintained for at least 15 seconds by clamping the tabletting tool in a vice.

The resistance to crushing of the tablets was determined with the stated apparatus in accordance with the stated method. The tablets did not break when exposed to a force of 500 N. The tablets did suffer a little plastic deformation.

In vitro release of the active ingredient was determined as in Example 8 and was:

| time | released quantity |
| --- | --- |
| 30 min | 22% |
| 120 min | 50% |
| 240 min | 80% |
| 360 min | 90% |
| 480 min | 99% |

Example 13

A tablet with the following composition was produced as described in Example 8:

| Components | per tablet | per batch |
| --- | --- | --- |
| oxycodone HCl | 20.0 mg | 0.240 g |
| Xanthan, NF | 20.0 mg | 0.240 g |
| polyethylene oxide, NF, MFI (190° C. at 21.6 kg/10 min) <0.5 g MW 7 000 000 (Polyox WSR 303, Dow Chemicals) | 110.0 mg | 1.320 g |
| total weight | 150.0 mg | 1.800 g |

Release of the active ingredient was determined as follows:

In vitro release of the active ingredient from the preparation was determined in a paddle stirrer apparatus in accordance with Pharm. Eur. The temperature of the release medium was 37° C. and the rotational speed 75 rpm. The phosphate buffer, pH 6.8, described in DSP served as the release medium. The quantity of active ingredient present in the solvent at the particular time of testing was determined by spectrophotometry.

| Time | mean |
| --- | --- |
| 0 min | 0% |
| 30 min | 17% |
| 240 min | 61% |
| 480 min | 90% |
| 720 min | 101.1% |

The resistance to crushing of the tablets was determined with the stated apparatus in accordance with the stated method. The tablets did not break when exposed to a force of 500 N.

Example 14

Tablets having the following composition were produced:

| components | per tablet | complete batch | content [%] |
| --- | --- | --- | --- |
| tramadol HCl | 100 mg | 10 g | 20 |
| polyethylene oxide 7 000 000 (Polyox WSR 303, Dow Chemicals) | 375 mg | 37.5 g | 75 |
| Carnauba wax | 25 mg | 2.5 g | 5.0 |

Tramadol hydrochlorid, polyethylene oxide and Carnauba wax were mixed in a free-fall mixer. The mixture was compressed on an excentric tablet press (model EK 0, Korsch) to circular tablets having a weight of 500 mg, a diameter of 10 mm and a radius of curvature of 8 mm. Then, the tabletting tool with top punch, bottom punch and die for tablets with a diameter of 10 mm and a radius of curvature of 8 mm was heated to 130° C. in a heating cabinet. Once again the tablets were compressed by means of the heated tool, wherein pressure was maintained for at least 15 seconds.

The resistance to crushing of the tablets was determined with the stated apparatus in accordance with the stated method. The tablets did not crush when exposed to a force of 500 N. The tablet could not be comminuted with a hammer. This could not be achieved with the assistance of a pestle and mortar either.

Example 15

Tablets having the following composition were produced as described in Example 14:

| Components | per tablet | complete batch | content [%] |
| --- | --- | --- | --- |
| tramadol HCl | 100 mg | 10 g | 20 |
| polyethylene oxide 5 000 000 (Polyox WSR Coagulant Dow Chemicals) | 375 mg | 37.5 g | 75 |
| Carnauba wax | 25 mg | 2.5 g | 5.0 |

The resistance to crushing of the tablets was determined with the stated apparatus in accordance with the stated method. The tablets did not crush when exposed to a force of 500 N. The tablet could not be comminuted with a hammer. This could not be achieved with the assistance of a pestle and mortar either.

Example 16

Tablets having the following composition were produced:

| Components | per tablet | complete batch | content [%] |
|---|---|---|---|
| tramadol HCl | 100.0 mg | 1490 g | 29.8 |
| polyethylene oxide 7 000 000 (Polyox WSR 303, Dow Chemicals) | 151.0 mg | 2250 g | 45.0 |
| Hypromellose (Metholose 90 SH 100 000 cP, ShinEtsu) | 33.6 mg | 500 g | 10.0 |
| Eudragit E Granulate (Rohm) | 16.8 mg | 250 g | 5.0 |
| PEG 6000 | 33.6 mg | 500 g | 10.0 |
| □-tocopherol | 0.1 mg | 5 g | 0.1 |
| Aerosil (highly disperse SiO$_2$) | 0.1 mg | 5 g | 0.1 |

A homogeneous mixture of 50 g of the polyethylene oxide, 5 g of □-tocopherol and Aerosil was prepared in a mortar. Said homogeneous mixture was mixed with the further components in a free-fall mixer for 15 minutes. Subsequently, the mixtures was extruded by means of a planetary-gear extruder, type BCG 10, LBB Bohle (Ennigerloh). 4 spindles were used. The die diameter was 8 mm. The dosing of the powder was performed gravimetrically, 10 kg per hour. The following parameters were adjusted for extrusion: rotation speed: 50 UpM; cover temperature: 100° C.; temperature of the central spindle: 100° C.; temperature of the jet heating: 120° C. After preparation the extrudates were allowed to cool down to room temperature. Thereafter, they were cut into slides having the desired tablet weight. Moulding of the tablets was performed by means of an excenter press, type EKO, Korsch. Circular punches having a diameter of 10 mm and a radius of curvature of 8 mm were used as tabletting tool.

The resistance to crushing of the tablets was determined with the stated apparatus in accordance with the stated method. The tablets did not crush when exposed to a force of 500 N. The tablet could not be comminuted with a hammer. This could not be achieved with the assistance of a pestle and mortar either.

In vitro release of the active ingredient from the preparation was determined in a paddle stirrer apparatus in accordance with Pharm. Eur. The temperature of the release medium (600 ml) was 37° C. and the rotational speed 75 rpm. The phosphate buffer, pH 6.8, described in DSP served as the release medium. The quantity of active ingredient present in the solvent at the particular time of testing was determined by spectrophotometry.

| Time | amount released |
|---|---|
| 30 min | 17% |
| 240 min | 65% |
| 480 min | 93% |
| 720 min | 99% |

Example 17

Tablets having the following composition were produced as described in Example 16:

| components | per tablet | complete batch | content [%] |
|---|---|---|---|
| tramadol HCl | 100.0 mg | 1490 g | 29.8 |
| polyethylene oxide 7 000 000 (Polyox WSR 303, Dow Chemicals) | 151.0 mg | 2250 g | 45.0 |
| Hypromellose (Metholose 90 SH 100 000 cP, ShinEtsu) | 33.6 mg | 500 g | 10.0 |
| Stamylan LD 1965 (SABIC ® LDPE 1965T) (Sabic Europetrochemicals) | 16.8 mg | 250 g | 5.0 |
| PEG 6000 | 33.6 mg | 500 g | 10.0 |
| □-tocopherol | 0.1 mg | 5 g | 0.1 |
| Aerosil (highly disperse SiO$_2$) | 0.1 mg | 5 g | 0.1 |

The resistance to crushing of the tablets was determined with the stated apparatus in accordance with the stated method. The tablets did not crush when exposed to a force of 500 N. The tablet could not be comminuted with a hammer. Nor could this be achieved with the assistance of a pestle and mortar.

In vitro release of the active ingredient from the preparation was determined in a paddle stirrer apparatus in accordance with Pharm. Eur. (paddle with sinker). The temperature of the release medium was 37° C. and the rotational speed of the stirrer 75 min$^{-1}$. 600 ml of artificial intestinal fluid pH 6.8 were used as release medium. The quantity of active ingredient released in each case into the dissolution medium at any one time was determined by spectrophotometry.

| time | amount released |
|---|---|
| 30 min | 17% |
| 240 min | 62% |
| 480 min | 85% |
| 720 min | 94% |

The invention claimed is:

1. A dosage form comprising a physiologically effective amount of a physiologically active substance (A), a polymer (C), optionally one or more physiologically acceptable auxiliary substances (B) and optionally a synthetic, semi-synthetic, or natural wax (D), wherein the dosage form exhibits a resistance to crushing of at least 400 N, wherein under physiological conditions the release of the physiologically active substance (A) from the dosage form is at least partially delayed, wherein the physiologically active substance (A) is the only physiologically active substance within the dosage form, wherein the physiologically active substance (A) consists of oxycodone, a physiologically acceptable salt of oxycodone, or a physiologically acceptable derivative of oxycodone, and wherein the polymer (C) is polyethylene oxide (PEO) having a molecular weight of 500,000 g/mol to 7 million g/mol determined according to rheological measurements.

2. The dosage form according to claim 1, wherein the dosage form exhibits a resistance to crushing of at least 500 N.

3. The dosage form according to claim 1, wherein the dosage form is in the form of a tablet.

4. The dosage form according to claim 1, wherein the dosage form is in multiparticulate form and the individual particles comprising the multiparticulate form exhibit a resistance to crushing of at least 400 N.

5. The dosage form according to claim 4, wherein the individual particles are pressed into tablets or packaged into capsules.

6. The dosage form according to claim 1, wherein the dosage form comprises a tubular domain and a core disposed therein, wherein the tubular domain is connected with the core in a seamless manner, and wherein the material forming the tubular domain and the material forming the core have substantially the same chemical composition but have different morphologies.

7. The dosage form according to claim 6, wherein the material forming the tubular domain and the material forming the core have different optical properties.

8. The dosage form according to claim 6, wherein the thickness of the tubular domain is within the range of 0.1 to 4 mm.

9. The dosage form according to claim 1, wherein the physiologically active substance (A), the polymer (C), the optional one or more physiologically acceptable auxiliary substances (B), and the optional synthetic, semi-synthetic, or natural wax (D) form a mixture and the volume of the dosage form increases by not more than 20% upon storage of the dosage form for at least 12 hours at a temperature of 20° C. below the melting range of the mixture.

10. The dosage form according to claim 1, wherein the dosage form comprises the synthetic, semi-synthetic, or natural wax (D) and wherein the synthetic, semi-synthetic, or natural wax (D) is at least one synthetic, semi-synthetic or natural wax with a softening point of at least 50° C.

11. The dosage form according to claim 10, wherein the synthetic, semi-synthetic, or natural wax (D) is carnauba wax or beeswax.

12. The dosage form according to claim 1, wherein the physiologically active substance (A) is present in a delayed-release matrix.

13. The dosage form according to claim 12, wherein the delayed-release matrix comprises at least one of the polymer (C) and the optional synthetic, semi-synthetic, or natural wax (D).

14. The dosage form according to claim 1, wherein the dosage form has released not more than 99% of the physiologically active substance (A) after 5 hours under physiological conditions.

15. A process for the production of a dosage form according to claim 1, said process comprising the following steps:
(a) mixing of the physiologically active substance (A), the polymer (C), the optional one or more physiologically acceptable auxiliary substances (B) and the optional synthetic, semi-synthetic, or natural wax (D);
(b) optionally preforming the mixture obtained from step (a);
(c) hardening the mixture or the optionally preformed mixture by applying heat and force, wherein the heat is supplied during and/or before the application of force and wherein the quantity of heat supplied is sufficient to heat the polymer (C) to at least up the softening point of the polymer (C) to form the dosage form;
(d) optionally singulating the hardened mixture before forming the dosage form;
(e) optionally shaping the dosage form; and
optionally providing a film coating to the dosage form.

16. The process according to claim 15, wherein step (c) is performed with a twin-screw-extruder or a planetary-gear extruder.

17. The process according to claim 15, wherein step (c) is performed with ultrasound and force.

18. The process according to claim 17, wherein step (e) is performed when the hardened mixture is in a plasticized state.

19. The product of the process of claim 15.
20. The product of the process of claim 16.
21. The product of the process of claim 18.
22. The product of the process of claim 17.

23. The dosage form according to claim 1, wherein the dosage form comprises the one or more physiologically acceptable auxiliary substances (B).

24. The dosage form according to claim 23, wherein the one or more physiologically acceptable auxiliary substances (B) comprises an at least one cellulose ether.

25. The dosage form according to claim 24, wherein said at least one cellulose ether is selected from the group consisting of ethyl cellulose, hydroxypropylmethylcellulose, hydroxypropylcellulose, and hydroxymethylcellulose.

26. The dosage form according to claim 25, wherein said at least one cellulose ether is hydroxypropylmethylcellulose.

27. The dosage form according to claim 1, wherein the polyethylene oxide (PEO) has a molecular weight of 1 million g/mol to 7 million g/mol.

28. The dosage form according to claim 2, wherein the dosage form is in the form of a tablet.

29. The dosage form according to claim 28, wherein the physiologically active substance (A) consists of a physiologically acceptable salt of oxycodone, and wherein the physiologically acceptable salt of oxycodone is oxycodone hydrochloride.

30. The dosage form according to claim 28, wherein the physiologically active substance (A) consists of a physiologically acceptable derivative of oxycodone, and wherein the physiologically acceptable derivative of oxycodone is selected from the group consisting of an ester of oxycodone, an ether of oxycodone, and an amides of oxycodone.

31. The dosage form according to claim 29, wherein the dosage form comprises the one or more physiologically acceptable auxiliary substances (B), and the one or more physiologically acceptable auxiliary substances (B) comprises at least one cellulose ether.

32. The dosage form according to claim 31, wherein said at least one cellulose ether is selected from the group consisting of ethyl cellulose, hydroxypropylmethylcellulose, hydroxypropylcellulose, and hydroxymethylcellulose.

33. The dosage form according to claim 32, wherein said at least one cellulose ether is hydroxypropylmethylcellulose.

34. The dosage form according to claim 3, wherein the physiologically active substance (A) consists of a physiologically acceptable salt of oxycodone, and wherein the physiologically acceptable salt of oxycodone is oxycodone hydrochloride.

35. The dosage form according to claim 3, wherein the physiologically active substance (A) consists of a physiologically acceptable derivative of oxycodone, and the physiologically acceptable derivative of oxycodone is selected from the group consisting of an ester of oxycodone, an ether of oxycodone, and an amide of oxycodone.

36. The dosage form according to claim 34, wherein the dosage form comprises the one or more physiologically acceptable auxiliary substances (B), wherein the one or more physiologically acceptable auxiliary substances (B) comprises an at least one cellulose ether.

37. The dosage form according to claim 36, wherein said at least one cellulose ether is selected from the group consisting of ethyl cellulose, hydroxypropylmethylcellulose, hydroxypropylcellulose, and hydroxymethylcellulose.

38. The dosage form according to claim 37, wherein said at least one cellulose ether is hydroxypropylmethylcellulose.

39. The process according to claim 15, further comprising forming the hardened mixture into a tablet.

40. The process according to claim 16, wherein the process produces an extruded strand, and the process further comprises singulating the extruded strand into an at least one singulated extrudates, and packaging the at least one singulated extrudate into a capsule.

* * * * *